US012616365B2

(12) United States Patent
Lee et al.

(10) Patent No.: US 12,616,365 B2
(45) Date of Patent: May 5, 2026

(54) METHODS AND SYSTEMS FOR IMPLEMENTING VIRTUAL VISION TEST FOR NIGHT VISION AND GLARE SENSITIVITY

(71) Applicant: Zenni Optical, Inc., Novato, CA (US)

(72) Inventors: Steven Lee, Barrington, IL (US); Julia Zhen, Novato, CA (US); ChyrSong Ting, Novato, CA (US); Matthew James Golino, Brookhaven, GA (US); Justin Paul Dempsey, Ottawa (CA); Jeffrey Joseph Fillingham, Dartmouth (CA)

(73) Assignee: Zenni Optical, Inc., Novato, CA (US)

( * ) Notice: Subject to any disclaimer, the term of this patent is extended or adjusted under 35 U.S.C. 154(b) by 0 days.

(21) Appl. No.: 18/820,121

(22) Filed: Aug. 29, 2024

(65) Prior Publication Data

US 2026/0060521 A1    Mar. 5, 2026

(51) Int. Cl.
*A61B 3/06*        (2006.01)
*A61B 3/00*        (2006.01)

(52) U.S. Cl.
CPC .............. *A61B 3/005* (2013.01); *A61B 3/063* (2013.01)

(58) Field of Classification Search
CPC ................................ A61B 3/005; A61B 3/063
See application file for complete search history.

(56) References Cited

U.S. PATENT DOCUMENTS

| | | | |
|---|---|---|---|
| 2,352,500 | A | 6/1944 | Shepard |
| 4,861,156 | A | 8/1989 | Terry |
| 5,737,060 | A | 4/1998 | Kasha, Jr. |
| 5,767,940 | A | 6/1998 | Hayashi et al. |
| 6,592,222 | B2 | 7/2003 | Massengill et al. |
| 7,784,948 | B2 | 8/2010 | Nozawa et al. |
| 10,238,280 | B2 | 3/2019 | Maeda et al. |
| 10,610,093 | B2 | 4/2020 | Green |
| 11,178,389 | B2 | 11/2021 | Sinha et al. |
| 11,426,107 | B2 | 8/2022 | Gibbons et al. |
| 11,633,097 | B1 | 4/2023 | Ziff et al. |
| 11,768,594 | B2 | 9/2023 | Cameron |
| 12,210,149 | B2 | 1/2025 | Jin et al. |

(Continued)

FOREIGN PATENT DOCUMENTS

| | | |
|---|---|---|
| CN | 2904944 Y | 5/2007 |
| CN | 109431445 A | 3/2019 |

(Continued)

*Primary Examiner* — Adam R. Giesy
(74) *Attorney, Agent, or Firm* — Morgan, Lewis & Bockius LLP

(57) ABSTRACT

A virtual eye test can be conducted to evaluate night vision and glare sensitivity in a virtual reality (VR) environment. The test can be conducted using an electronic device that includes a head-mounted display (HMD) and a camera. The electronic device can generate a VR user interface corresponding to a photorealistic virtual environment and render the VR user interface on the HMD. The electronic device can simulate one or more dynamic lighting scenarios and while simulating these scenarios, in real time, continuously track eye movements and response times to visual stimuli using the camera. The device can then evaluate user response based on the eye movements and response times for testing night vision and glare sensitivity.

20 Claims, 49 Drawing Sheets

(56)                References Cited

U.S. PATENT DOCUMENTS

| | | | | |
|---|---|---|---|---|
| 2012/0240261 A1* | 9/2012 | Carden | ................. | A01H 6/542 |
| | | | | 800/278 |
| 2017/0017083 A1* | 1/2017 | Samec | ............... | G02B 27/0172 |
| 2019/0008441 A1 | 1/2019 | Guzik | | |
| 2019/0298166 A1 | 10/2019 | Smith et al. | | |
| 2019/0328305 A1 | 10/2019 | Wood et al. | | |
| 2019/0350452 A1 | 11/2019 | Lewis | | |
| 2022/0354413 A1 | 11/2022 | Rah | | |
| 2023/0404388 A1* | 12/2023 | Tavakkoli | ............. | A61B 3/063 |

FOREIGN PATENT DOCUMENTS

| | | | |
|---|---|---|---|
| GR | 1005651 | B | 9/2007 |
| HU | 185600 | B | 2/1985 |
| JP | 2721892 | B2 | 3/1998 |
| JP | 2000079095 | A | 3/2000 |
| JP | 2001275968 | A | 10/2001 |
| JP | 2001286442 | A | 10/2001 |
| JP | 3259920 | B2 | 2/2002 |
| JP | 2002051981 | A | 2/2002 |
| JP | 2003038440 | A | 2/2003 |
| JP | 2003079574 | A | 3/2003 |
| JP | 3655129 | B2 | 6/2005 |
| JP | 2012100758 | A | 5/2012 |
| JP | 5007435 | B2 | 8/2012 |
| WO | 1994013192 | A1 | 6/1994 |
| WO | 2011022428 | A2 | 2/2011 |
| WO | 2016165272 | A1 | 10/2016 |
| WO | 2017070704 | A2 | 4/2017 |
| WO | 2021018224 | A1 | 2/2021 |
| WO | 2022111663 | A1 | 6/2022 |

* cited by examiner

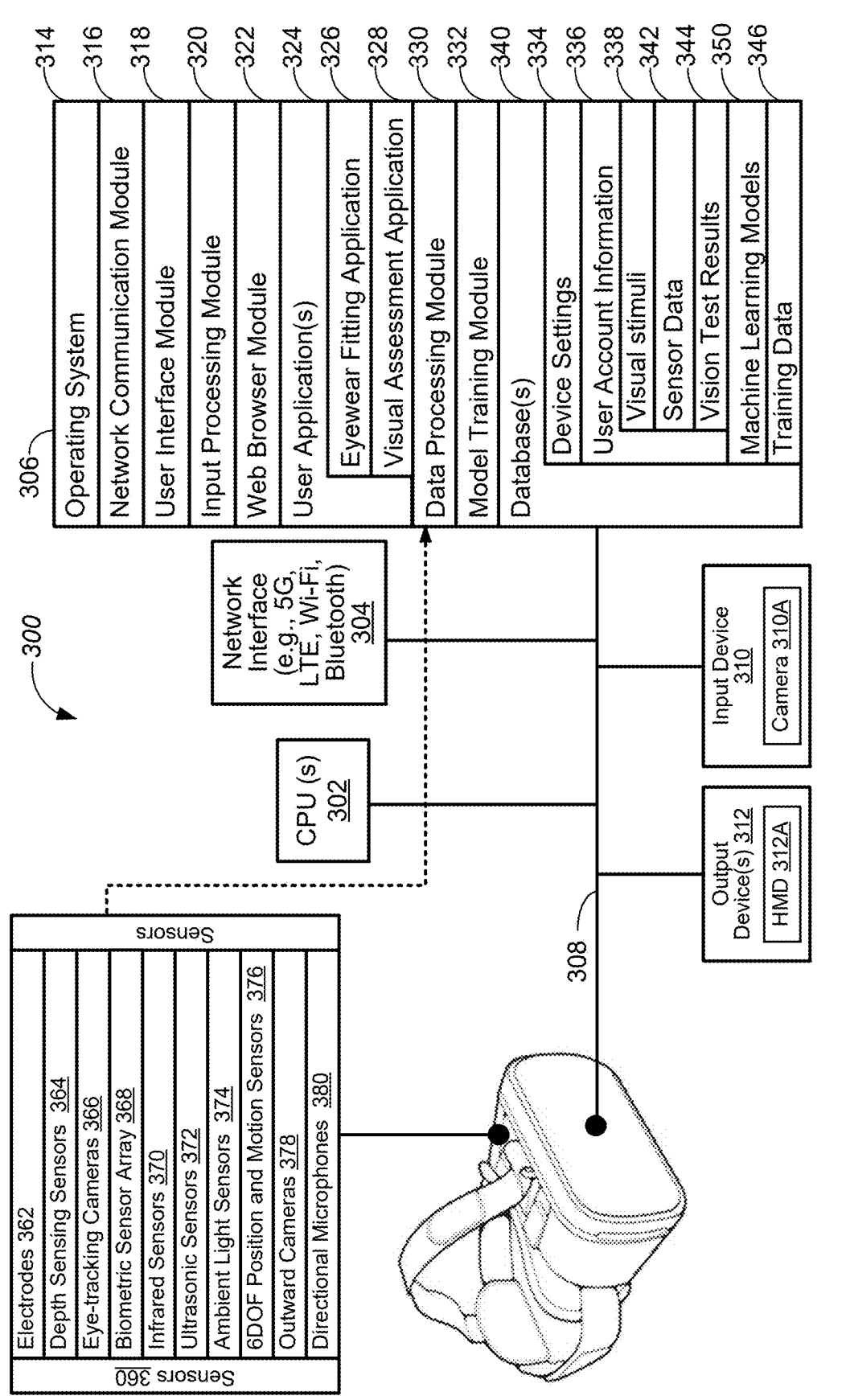

FIG. 3

314 Operating System
316 Network Communication Module
318 User Interface Module
320 Input Processing Module
322 Web Browser Module
324 User Application(s)
326 Eyewear Fitting Application
328 Visual Assessment Application
330 Data Processing Module
332 Model Training Module
340 Database(s)
334 Device Settings
336 User Account Information
338 Visual stimuli
342 Sensor Data
344 Vision Test Results
350 Machine Learning Models
346 Training Data

306

300

Network Interface (e.g., 5G, LTE, Wi-Fi, Bluetooth) 304

CPU (s) 302

Input Device 310
Camera 310A

Output Device(s) 312
HMD 312A

308

Sensors

Sensors 360

Electrodes 362
Depth Sensing Sensors 364
Eye-tracking Cameras 366
Biometric Sensor Array 368
Infrared Sensors 370
Ultrasonic Sensors 372
Ambient Light Sensors 374
6DOF Position and Motion Sensors 376
Outward Cameras 378
Directional Microphones 380

810

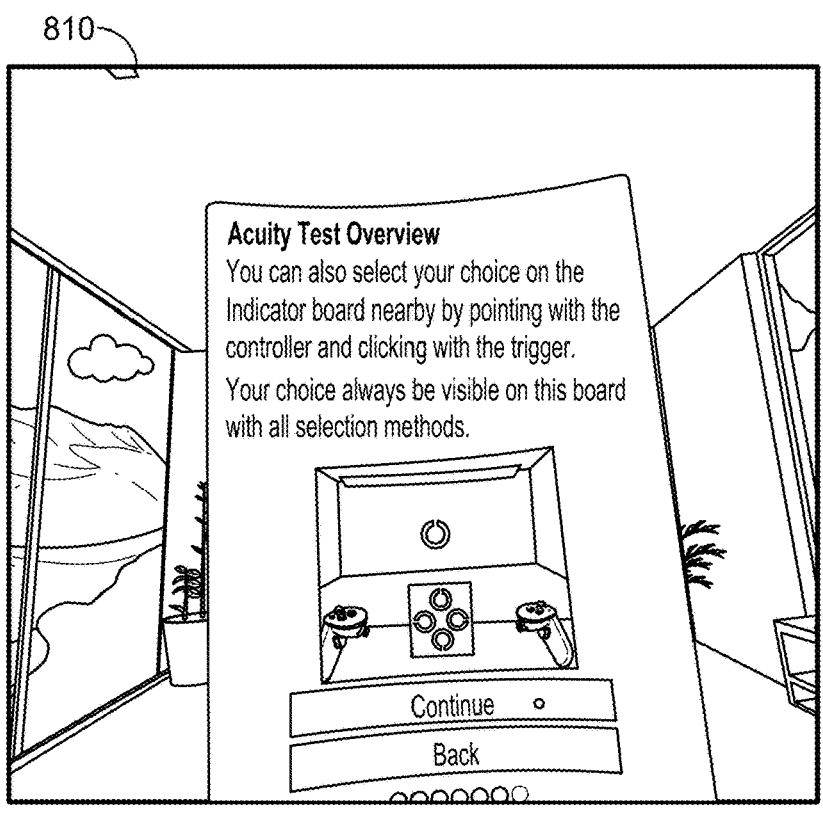

Acuity Test Overview
You can also select your choice on the Indicator board nearby by pointing with the controller and clicking with the trigger.
Your choice always be visible on this board with all selection methods.

Continue ∘
Back

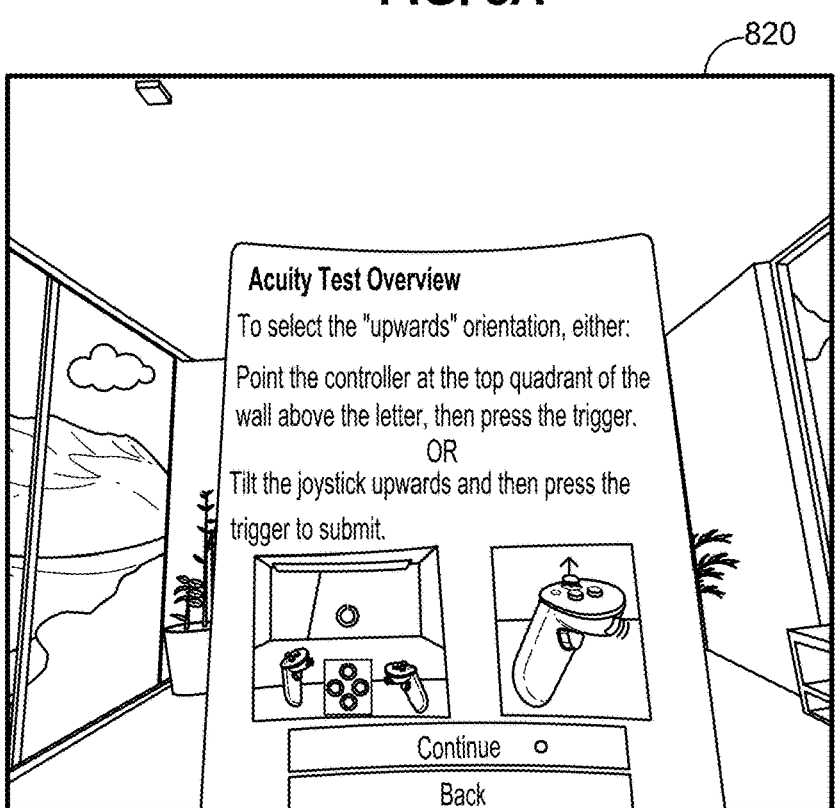

Acuity Test Overview
To select the "upwards" orientation, either:

Point the controller at the top quadrant of the wall above the letter, then press the trigger.
OR
Tilt the joystick upwards and then press the trigger to submit.

Continue ∘
Back

Vision Test
System 1100

1102 ── Processor(s)

1128 ── Camera(s) and/
or Sensor(s)

1126

1104 ── HMD

Display ── 1106

Lenses ── 1108

Physical
structure ── 1110

Camera,
Sensors ── 1112

Audio ── 1114

Processor(s) ── 1116

1124 ── Memory

1122 ── Input Device(s)

1120 ── Battery

1118 ── Communication
interface(s)

1124

Memory
1124

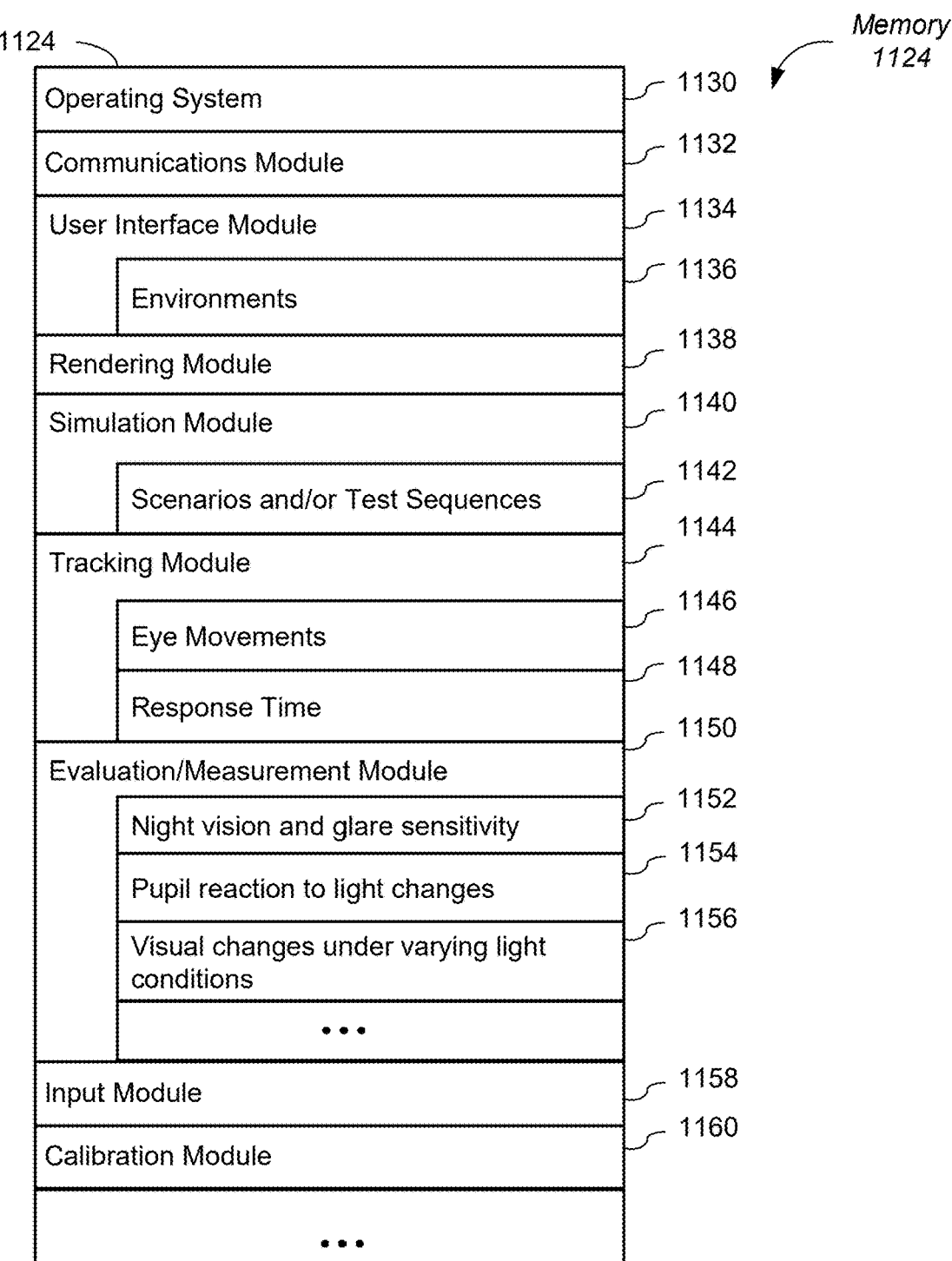

Operating System ⟶ 1130

Communications Module ⟶ 1132

User Interface Module ⟶ 1134

Environments ⟶ 1136

Rendering Module ⟶ 1138

Simulation Module ⟶ 1140

Scenarios and/or Test Sequences ⟶ 1142

Tracking Module ⟶ 1144

Eye Movements ⟶ 1146

Response Time ⟶ 1148

Evaluation/Measurement Module ⟶ 1150

Night vision and glare sensitivity ⟶ 1152

Pupil reaction to light changes ⟶ 1154

Visual changes under varying light conditions ⟶ 1156

● ● ●

Input Module ⟶ 1158

Calibration Module ⟶ 1160

Generate a virtual reality user interface corresponding to photorealistic environment
1202

( A )        ( B )

Render the VR user interface on the HMD
1204

Simulate one or more dynamic lighing scenarios in the VR user interface
1206

( C )  ( D )  ( E )  ( F )  ( G )

While simulating the one or more dynamic lighting scenarios, in real time:
1208

Continuously track, using the camera, eye movements and response times in response to visual stimuli presented in the one or more dynamic lighting scenarios 1210        ( H )

Evaluate user response based on the eye movements and the response times for testing night vision and glare sensitivity
1212

( I )        ( J )

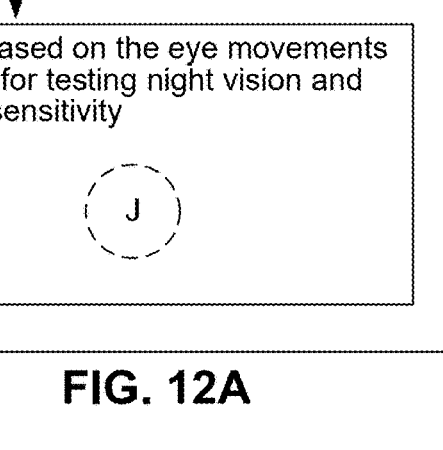

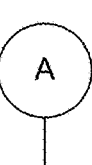

The photorealistic virtual environment includes a high-fidelity virtual environment that can dynamically adjust light levels, colors, and/or sources
1214

The high-fidelity virtual environment includes dynamic light sources that incorporate movable light sources that can change intensity and position
1216

The movable light sources includes one or more light sources selected from the group consisting of: headlights, streetlights and reflections
1218

FIG. 12B

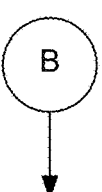

The photorealistic virtual environment includes one or more configurable parameters to alter environment settings, while simulating the one or more dynamic lighting scenarios
1220

The environment settings include one or more settings selected from the group consisting of: weather conditions, time of day, and urban or rural settings
1222

The environment settings are alterable via user input
1224

The environment settings are alterable automatically depending on a test parameter for testing night vision and glare sensitivity
1226

FIG. 12C

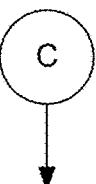

The one or more dynamic lighting scenarios includes randomized lighting scenarios that randomly change intensity from high intensity to low intensity and vice versa, without following real-world lighting scenarios
1228

The one or more dynamic lighting scenarios includes using one or more light mapping techniques to simulate realistic light behavior, including scattering, shadowing, and reflections
1230

The one or more dynamic lighting scenarios includes one or more night time scenes in urban streets, country roads, or indoor settings, simulated with varying degrees of ambient light
1232

The one or more dynamic lighting scenarios includes one or more low-light environments selected from the group consisting of: dimly lit parking garages, moonlit landscapes and twilight settings
1234

FIG. 12D

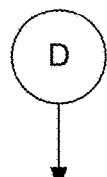

The one or more dynamic lighting scenarios includes one or more nighttime scenes including an urban street with variable lighting from cars, streetlights and shop windows
1236

The one or more dynamic lighting scenarios includes one or more low-light level scenarios including a twilight park, dimly lit alley, or an interior of a room with dim lighting
1238

The one or more dynamic lighting scenarios includes one or more glare levels for simulating driving towards oncoming traffic, navigating through a brightly lit street with reflective surfaces, or encountering a sudden flash of bright light
1240

FIG. 12E

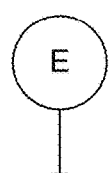

Simulating the one or more dynamic lighting scenarios includes simulating one or more scenarios that cause glare, the one or more scenarios selected from the group consisting of: oncoming headlights, street lights, neon signs, and reflective surfaces that cause glare
1242

Simulating the one or more dynamic lighting scenarios includes varying direction and intensity of light from one or more light sources hitting an eye
1244

Simulating the one or more dynamic lighting scenarios includes simulating one or more scenarios for assessing the ability to distinguish between different shades of gray including changing optotype direction, whereby after solid black light, solid black is changed to a level of gray having a different gray level closer to white, including smoothing to lessen pixelation
1246

FIG. 12F

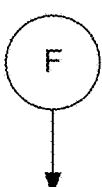

Simulating the one or more dynamic lighting scenarios includes exposing an eye to the bright light to bleach the eye, by shining the bright light
1248

Simulating the one or more dynamic lighting scenarios includes starting with one or more simpler tasks for identifying stationary objects, progressing to more complex tasks including reading moving signs or navigating through a virtual maze, wherein each task lasts between 30 seconds to 2 minutes, with controlled lighting transitions
1250

Simulating the one or more dynamic lighting scenarios includes controlling one or more lighting conditions to change predictably and repeatably for each user to maintain consistency in testing across users
1252-0

Simulating the one or more dynamic lighting scenarios comprises using a library of lighting conditions that categorizes simulations by ambient light levels, dynamic glare sources, and specific environments
1252-2

Simulating the one or more dynamic lighting scenarios comprises using a library of lighting conditions that allows selection of specific scenarios or includes a preset sequence designed to test various aspects of night vision and glare sensitivity
1252-4

FIG. 12G

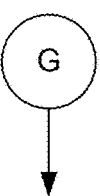

Prior to simulating the one or more dynamic lighting scenarios in the VR user interface:
1254

Provide a visual stimuli in the VR user interface to measure a user's susceptibility level to motion sickness
1256

In accordance with a determination that the user's susceptibility to motion sickness is above a predetermined threshold, reduce a refresh rate of the VR user interface
1258

FIG. 12H

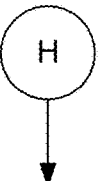

Tracking the eye movements and response times includes tracking eye ball position in relation to light sensitivity while using a light source to cause glare
1260

FIG. 12I

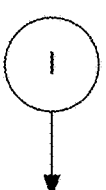

Evaluating user response based on the eye movements and the response times for testing night vision and glare sensitivity includes tracking a response time to adapt to changes in lighting conditions as light is decreased
1262

Evaluating user response based on the eye movements and the response times for testing night vision and glare sensitivity includes tracking a focus on a glare as light is decreased
1264

Evaluating the user response based on the eye movements and the response times for testing night vision and glare sensitivity includes measuring visual acuity under varying light conditions using tests including dynamic Snellen charts
1266

Evaluating the user response based on the eye movements and the response times for testing night vision and glare sensitivity includes assessing an ability to distinguish between different shades of gray in low-light scenarios
1268

Evaluating the user response based on the eye movements and the response times for testing night vision and glare sensitivity includes measuring a time taken for a vision to return to baseline or normal vision after exposure to a bright light
1270

FIG. 12J

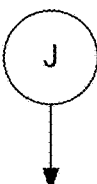

Evaluating the user response based on the eye movements and the response times for testing night vision and glare sensitivity includes (i) one or more objective tests based on a response that indicates when a user starts seeing again, and (ii) one or more subjective tests including one or more vision acuity tests

1272

Evaluating the user response based on the eye movements and the response times for testing night vision and glare sensitivity includes collecting data on reaction times, accuracy of task completion, eye movement patterns, and recovery times from glare

1274

Evaluating the user response based on the eye movements and the response times for testing night vision and glare sensitivity includes using one or more metrics for identification accuracy, time to task completion, and time to visual recovery from glare, to assess night vision and glare sensitivity

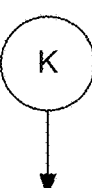

Generate one or more reports for summarizing a performance across different lighting conditions
1278

Generate one or more charts for showing visual clarity in low-light scenarios
1280

Generate one or more graphs indicating recovery times from different levels of glare exposure
1282

Display results from various contrast levels tested
1284

Display one or more suggestions for further evaluation or corrective measures if deficiencies are identified
1286

FIG. 12L

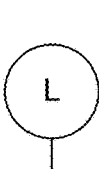
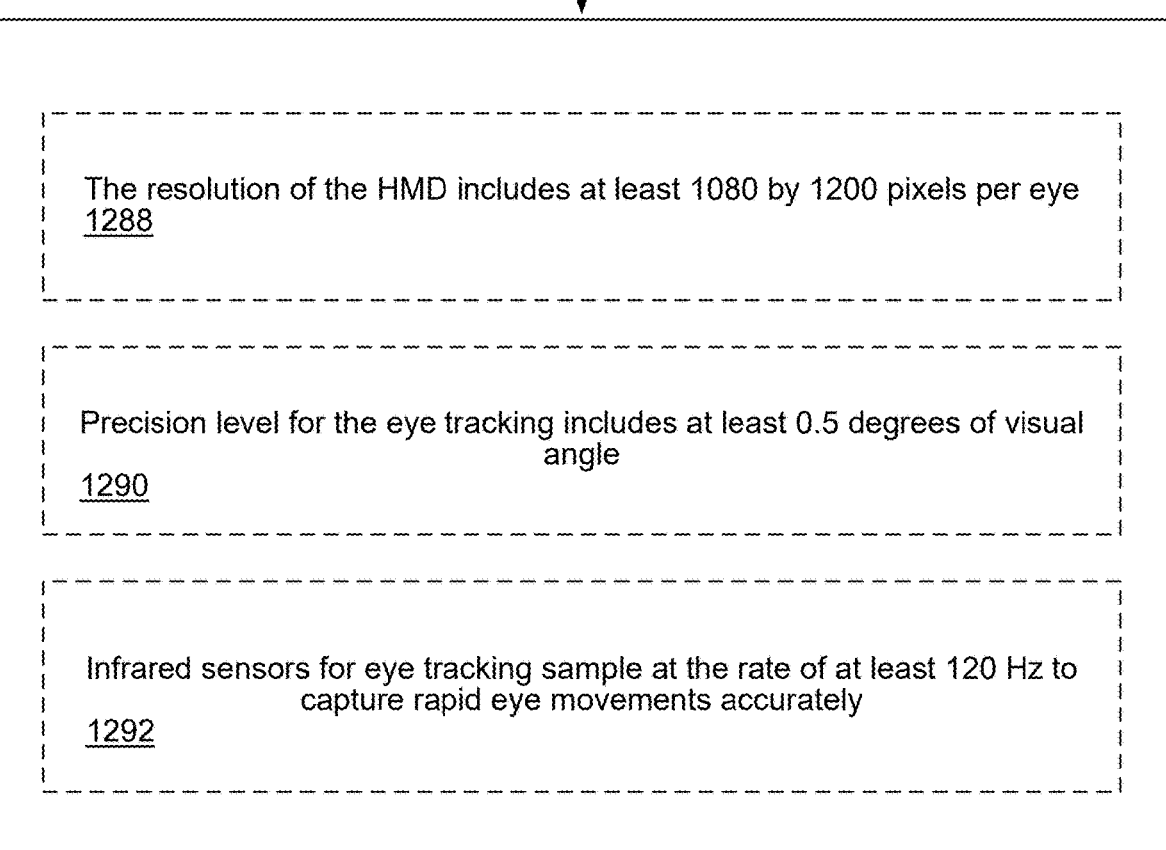
The resolution of the HMD includes at least 1080 by 1200 pixels per eye
1288
Precision level for the eye tracking includes at least 0.5 degrees of visual angle
1290
Infrared sensors for eye tracking sample at the rate of at least 120 Hz to capture rapid eye movements accurately
1292
FIG. 12M

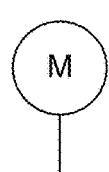

Calibrate the one or more dynamic lighting scenarios using a control group including individuals with known conditions including retinitis pigmentosa (night blindness), normal vision, and those with a history of glare sensitivity 1294

Calibrate the one or more dynamic lighting scenarios using baseline metrics including average reaction times, standard recovery times from glare, and typical contrast sensitivity scores for each profile 1296

Validate results of testing by comparing results from the VR tests with conventional clinical tests to ensure accuracy 1298-0

Use statistical methods to validate consistency and reliability of the VR-based assessments 1298-2

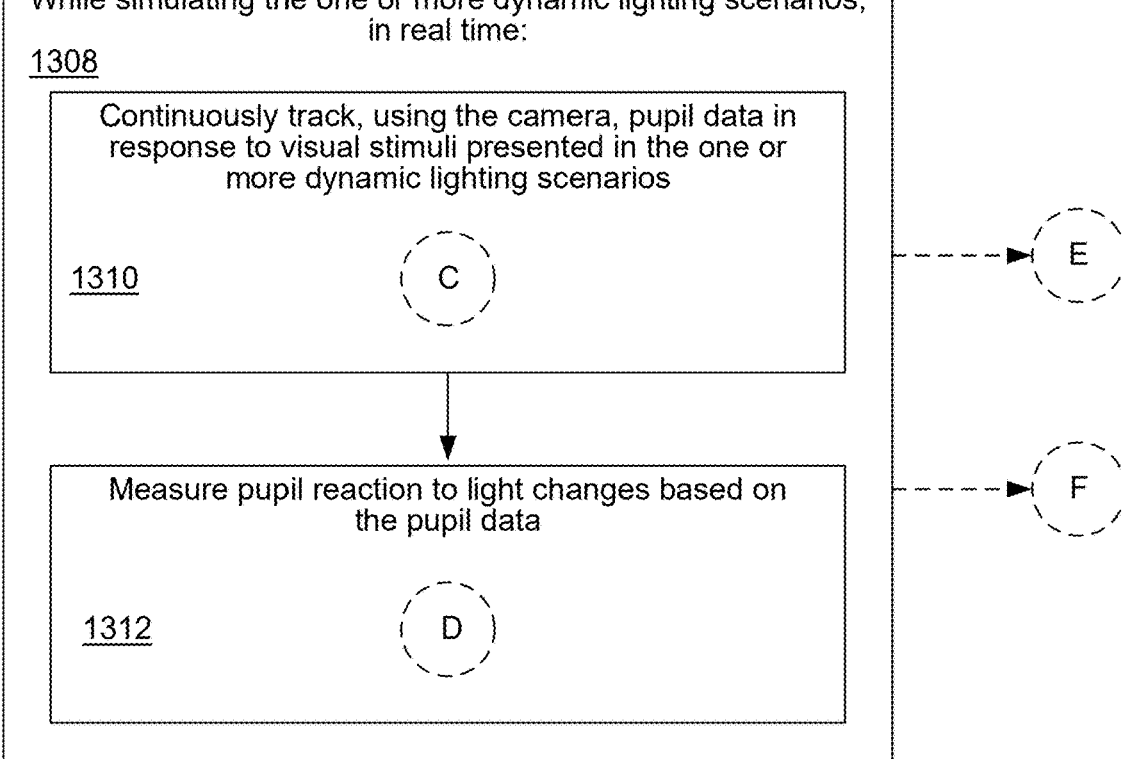

Generate a virtual reality user interface corresponding
to photorealistic environment
1302

Render the VR user interface on the HMD
1304

Simulate one or more dynamic lighting scenarios in the
VR user interface
1306

A        B

While simulating the one or more dynamic lighting scenarios,
in real time:
1308

Continuously track, using the camera, pupil data in
response to visual stimuli presented in the one or
more dynamic lighting scenarios

1310          C          E

Measure pupil reaction to light changes based on
the pupil data

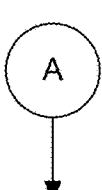

The one or more dynamic lighting scenarios includes sudden flashes of light that last between 100 to 500 milliseconds
1314

Time between the sudden flashes of light range from 1 to 5 seconds
1316

The one or more dynamic lighting scenarios includes flashes with varying light intensities, from dim (10 cd/m2) to very bright (1000 cd/m2)
1318

The one or more dynamic lighting scenarios includes scenarios with gradual changes in brightness with transitions over periods of 5 to 30 seconds
1320

The one or more dynamic lighting scenarios includes one or more scenarios selected from the group consisting of: sunrise, sunset and moving from a dimly lit room to a brightly lit outdoor environment
1322

The one or more dynamic lighting scenarios includes a series of 10 flashes, each 100 milliseconds long, with 2-second intervals
1324

FIG. 13B

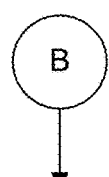

The one or more dynamic lighting scenarios includes a plurality of flashes with a 3.5 second interval between a first flash and a second flash and a 4.5 second interval between the second flash and a third flash
1326

The one or more dynamic lighting scenarios includes a plurality of flashes with at least a 3 second interval and lesser than a 10 second interval between two flashes
1328

Simulating the one or more dynamic lighting scenarios includes driving lighting scenarios using a lighting scenarios library that categorizes abrupt changes for sudden flashes having subcategories for low, medium and high intensities, and gradual changes to brightness having subcategories for slow, medium and fast transitions
1330

The sudden flashes include 100 ms flashes at 100 cd/m2 and 500 ms flashes at 500 cd/m2
1332

The gradual brightness adjustment includes 10-second transition from 100 cd/m2 to 500 cd/m2, and 30-second transition from 10 cd/m2 to 1,000 cd/m2
1334

FIG. 13C

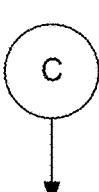

Tracking the pupil data includes using infrared light to monitor pupil size and movements without visible light interference, and tracking and recording pupil responses
1336

Tracking the pupil data includes using one or more pupilometers of the electronic device to measure pupil response to light changes accurately
1338

Tracking the pupil data includes using high-resolution infrared eye-tracking cameras capable of capturing detailed pupil size and movement that sample at least at 120 Hz
1340

Tracking pupil data includes using at least 0.1 mm precision for measuring pupil size
1342

Tracking pupil data is performed at the rate of 5 milliseconds to ensure real-time tracking
1344

Tracking pupil data includes using high-resolution sensors for capturing detailed images of the pupil
1346

FIG. 13D

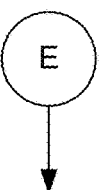

Map abnormalities including anisocoria, optic neuropathy, and visual pathway disorder, based on measuring the pupil reaction to light changes
1356

Map abnormalities to anisocoria includes comparing responses of both eyes to identify differences in pupil size, based on the pupil data
1358

Map abnormalities to optic neuropathy includes analyzing consistency and speed of pupil responses to thereby detect potential nerve damage
1360

Map abnormalities to visual pathway disorder includes using one or more machine learning algorithms to compare responses to baseline data from individuals with known conditions
1362

FIG. 13F

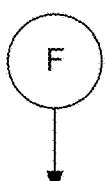

Calibrate the one or more dynamic lighting scenarios based on a control group including individuals with normal vision, individuals with anisocoria, and individuals with optic neuropathy
1364

Calibrate the one or more dynamic lighting scenarios using baseline responses for individuals with no known visual impairments, baseline for individuals with unequal pupil sizes, and baseline for individuals with optic nerve damage
1366

Calibrate the one or more dynamic lighting scenarios using baseline pupillary responses including average latency of 150 ms, average constriction of 2.5 mm, and average constriction speed of 0.5 mm/s
1368

Validate the measured pupil reaction to light changes by comparing a test group's responses to a control group's baseline metrics
1370

Validate the measured pupil reaction to light changes using statistical methods including t-tests to validate the accuracy and consistency of measurement algorithms
1372

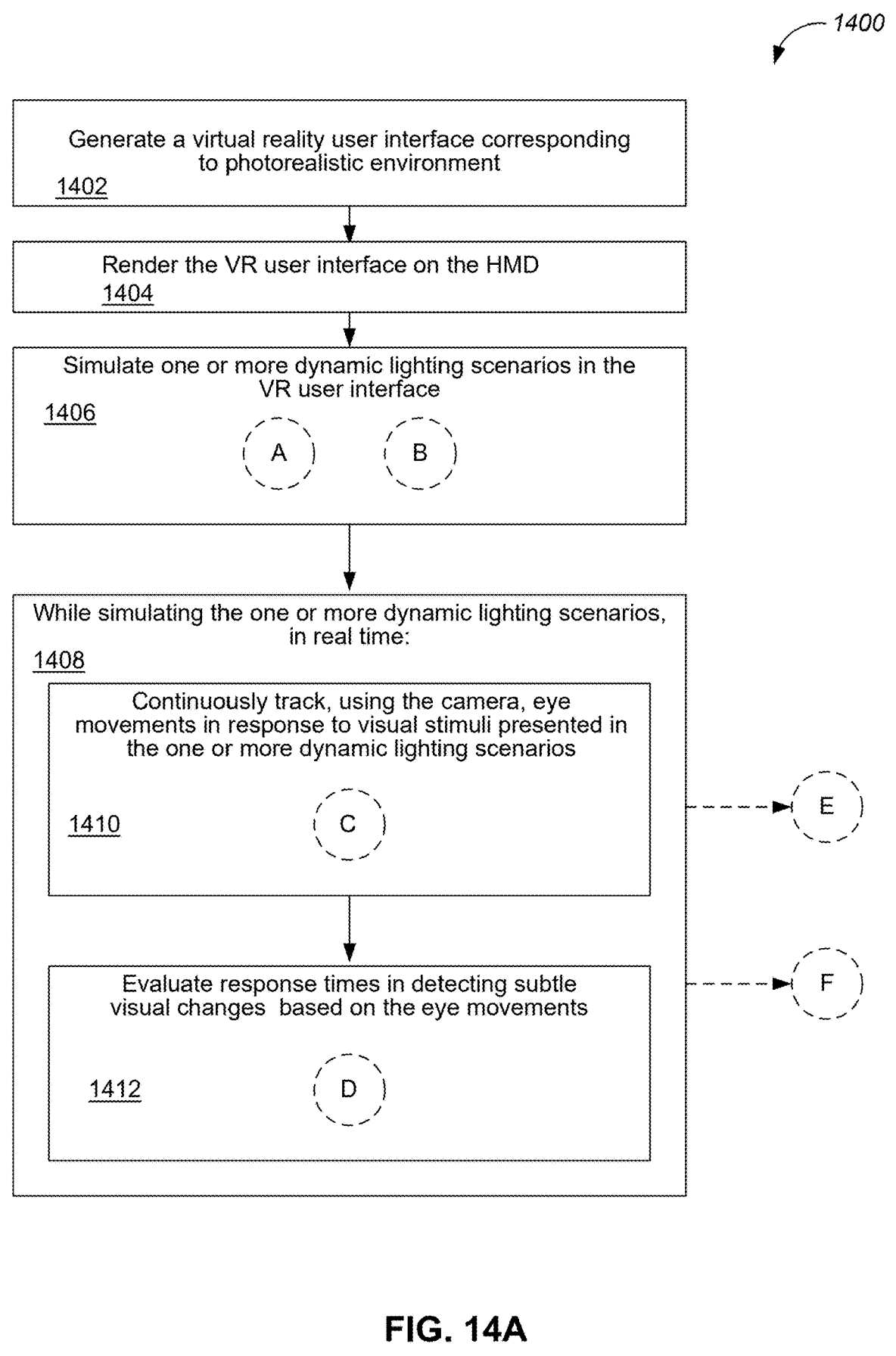

Generate a virtual reality user interface corresponding to photorealistic environment
1402

Render the VR user interface on the HMD
1404

Simulate one or more dynamic lighting scenarios in the VR user interface
1406

( A )    ( B )

While simulating the one or more dynamic lighting scenarios, in real time:
1408

Continuously track, using the camera, eye movements in response to visual stimuli presented in the one or more dynamic lighting scenarios 1410    ( C )    - - - ►( E )

Evaluate response times in detecting subtle visual changes based on the eye movements 1412    ( D )    - - - ►( F )

FIG. 14A

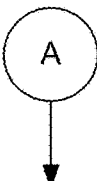

Simulate the one or more dynamic visual scenarios includes generating and controlling subtle changes in visual field, including slight alterations in color, shape or movement
1414

The one or more dynamic visual scenarios includes one or more scenarios for identifying slight changes in color hue or brightness in a specific part of a visual field, including using color gradients that change slowly and subtly, requiring a user to respond when they detect the change
1416

The one or more dynamic visual scenarios includes one or more scenarios for detecting minor alterations in the shape of objects including slight deformation of a geometric figure, including displaying objects that gradually morph in shape, prompting users to identify the change
1418

The one or more dynamic visual scenarios includes one or more scenarios for identifying subtle movements within a stationary visual scene, including a slight shift in the position of an object, including implementing background scenes where certain elements move minimally, requiring users to pinpoint these movements
1420

FIG. 14B

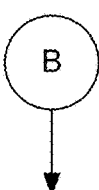

The one or more dynamic visual scenarios include lighting environments with (i) dim lighting that simulate low-light environments with brightness levels around 10 cd/m2
1422

The one or more dynamic visual scenarios include lighting environments with bright lighting that simulate environments with high brightness around 1000 cd/m2
1424

The one or more dynamic visual scenarios include lighting environments with fluctuating light levels including dynamic changes in lighting, transitioning between dim and bright environments over 5 to 30 seconds
1426

The one or more dynamic lighting scenarios include subtle visual changes including color changes for gradual shifts in hue or saturation, requiring quick detection, shape changes for minor alterations in geometric chapes or object outlines, and slight, almost imperceptible movements within a scene
1428

Simulating the one or more dynamic lighting scenarios includes using a library of lighting conditions that categorizes scenarios by (i) a type of visual change including color, shape and movement, and (ii) lighting environment including dim, bright and fluctuating
1430

The library of lighting conditions further categorizes each scenario by a level of difficulty based on subtlety of changes and speed required for detecting subtle changes in color gradients for color detection, minor deformations of geometric figures for shape alterations, and slight shifts in object positions for movement detection
1432

FIG. 14C

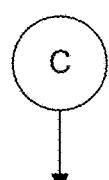

Tracking the eye movements includes using eye-tracking sensors with accuracy of 0.5 degrees of visual angle or better, at a sampling rate of at least 120 Hz to accurately capture quick eye movements and response times
1434

Tracking the eye movements includes using infrared eye-tracking sensors to capture detailed eye movements, including fixations, saccades, and blinks
1436

Tracking eye movements includes using at least 0.1 mm precision for measuring eye movements
1438

Tracking eye movements is performed with a latency below 5 milliseconds to ensure real-time tracking
1440

Tracking eye movements includes using high-resolution sensors for capturing detailed images of the pupil and eye movement data
1442

FIG. 14D

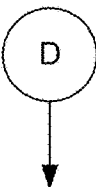

Evaluating response times includes mapping the response times to specific visual stimuli presented in the photorealistic virtual environment, correlating eye movement data with the appearance of visual changes
1444

Evaluating response times includes mapping the eye movements to visual perception and cognitive processing speed
1446

Evaluating response times includes measuring latency including calculating time taken from the presentation of a visual change to the user's detection as indicated by an eye movement or a press of a button
1448

Evaluating the eye movements includes collecting baseline data from a control group with known visual and cognitive health status, and comparing response times and accuracy against the baseline data to identify deviations indicative of potential impairments
1450

FIG. 14E

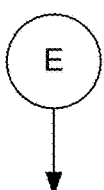

The electronic device includes a high-resolution headset offering at least 1080 times 1200 pixels per eye, at least 90 Hz refresh rate to ensure smooth visual presentation and reduce motion sickness, and a wide field of view (FOV) of at least 110 degrees to provide an immersive experience 1452

Providing insights into visual and cognitive processing abilities based on analysis of speed and accuracy of responses based on the eye movements 1454

Providing an analysis of performance under each lighting condition, including reaction times and detection accuracy 1456

Providing a diagnostic including highlighting areas of concern that suggest conditions including macular degeneration, glaucoma, or cognitive decline 1458

FIG. 14F

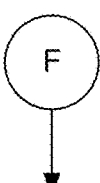

Calibrate the one or more dynamic lighting scenarios using known visual and cognitive health profiles of a control group including individuals with normal vision, age-related macular degeneration, glaucoma, early cognitive decline, and other relevant conditions
1460

Calibrate the one or more dynamic lighting scenarios using baseline metrics including average reaction times, detection accuracy, and other relevant metrics
1462

Use statistical methods including t-tests and ANOVA to validate consistency and reliability of the VR-based assessments by comparing test results against baseline metrics
1464

Validate results of testing by comparing results from the VR tests across different users and sessions
1466

Figure 16D:
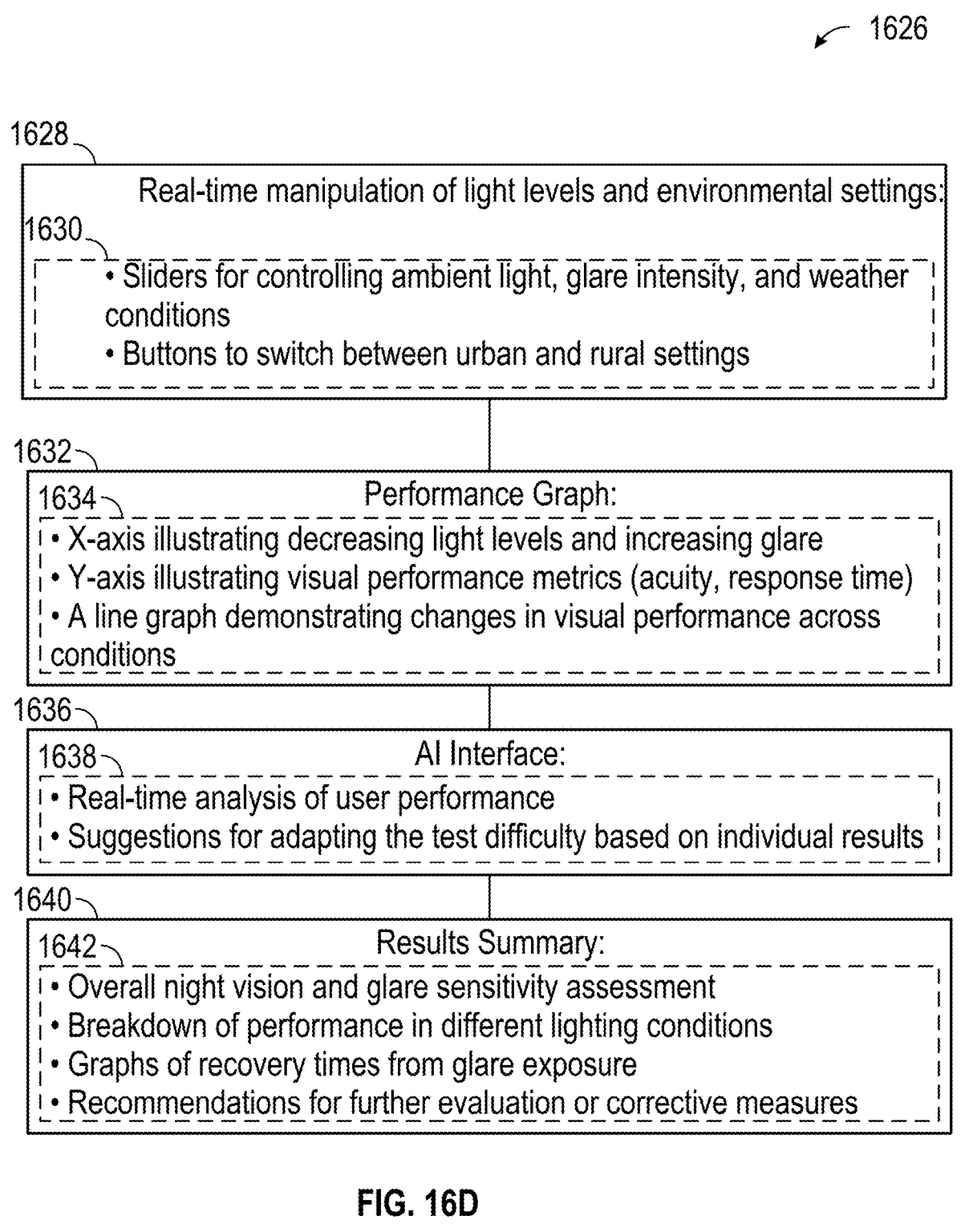

Real-time manipulation of light levels and environmental settings:

1630

• Sliders for controlling ambient light, glare intensity, and weather conditions
• Buttons to switch between urban and rural settings

1632

Performance Graph:

1634

• X-axis illustrating decreasing light levels and increasing glare
• Y-axis illustrating visual performance metrics (acuity, response time)
• A line graph demonstrating changes in visual performance across conditions

1636

AI Interface:

1638

• Real-time analysis of user performance
• Suggestions for adapting the test difficulty based on individual results

1640

Results Summary:

1642

• Overall night vision and glare sensitivity assessment
• Breakdown of performance in different lighting conditions
• Graphs of recovery times from glare exposure
• Recommendations for further evaluation or corrective measures

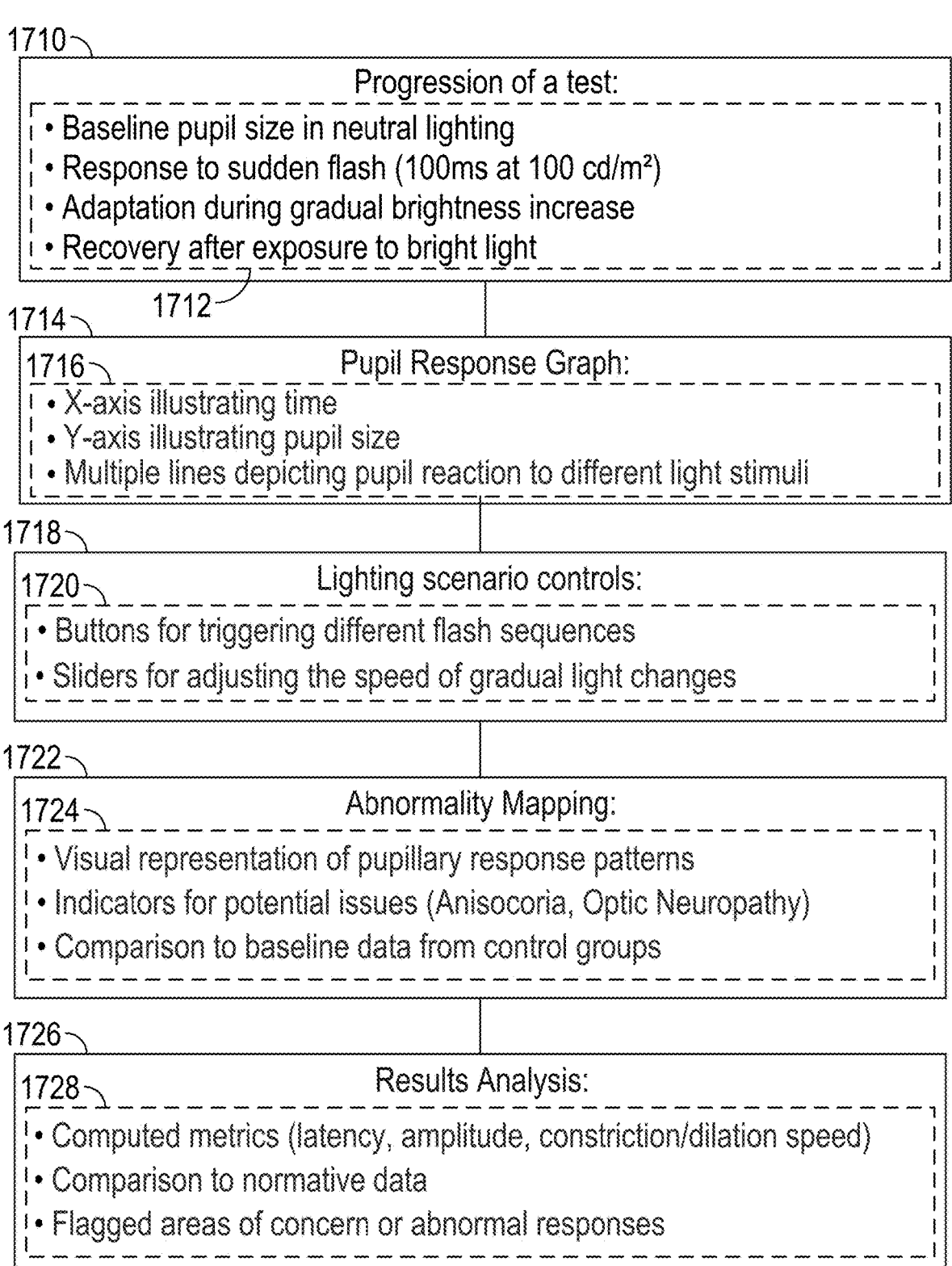

1710

Progression of a test:
- Baseline pupil size in neutral lighting
- Response to sudden flash (100ms at 100 cd/m²)
- Adaptation during gradual brightness increase
- Recovery after exposure to bright light

1712

1714

1716     Pupil Response Graph:
- X-axis illustrating time
- Y-axis illustrating pupil size
- Multiple lines depicting pupil reaction to different light stimuli

1718

1720     Lighting scenario controls:
- Buttons for triggering different flash sequences
- Sliders for adjusting the speed of gradual light changes

1722

1724     Abnormality Mapping:
- Visual representation of pupillary response patterns
- Indicators for potential issues (Anisocoria, Optic Neuropathy)
- Comparison to baseline data from control groups

1726

1728     Results Analysis:
- Computed metrics (latency, amplitude, constriction/dilation speed)
- Comparison to normative data
- Flagged areas of concern or abnormal responses

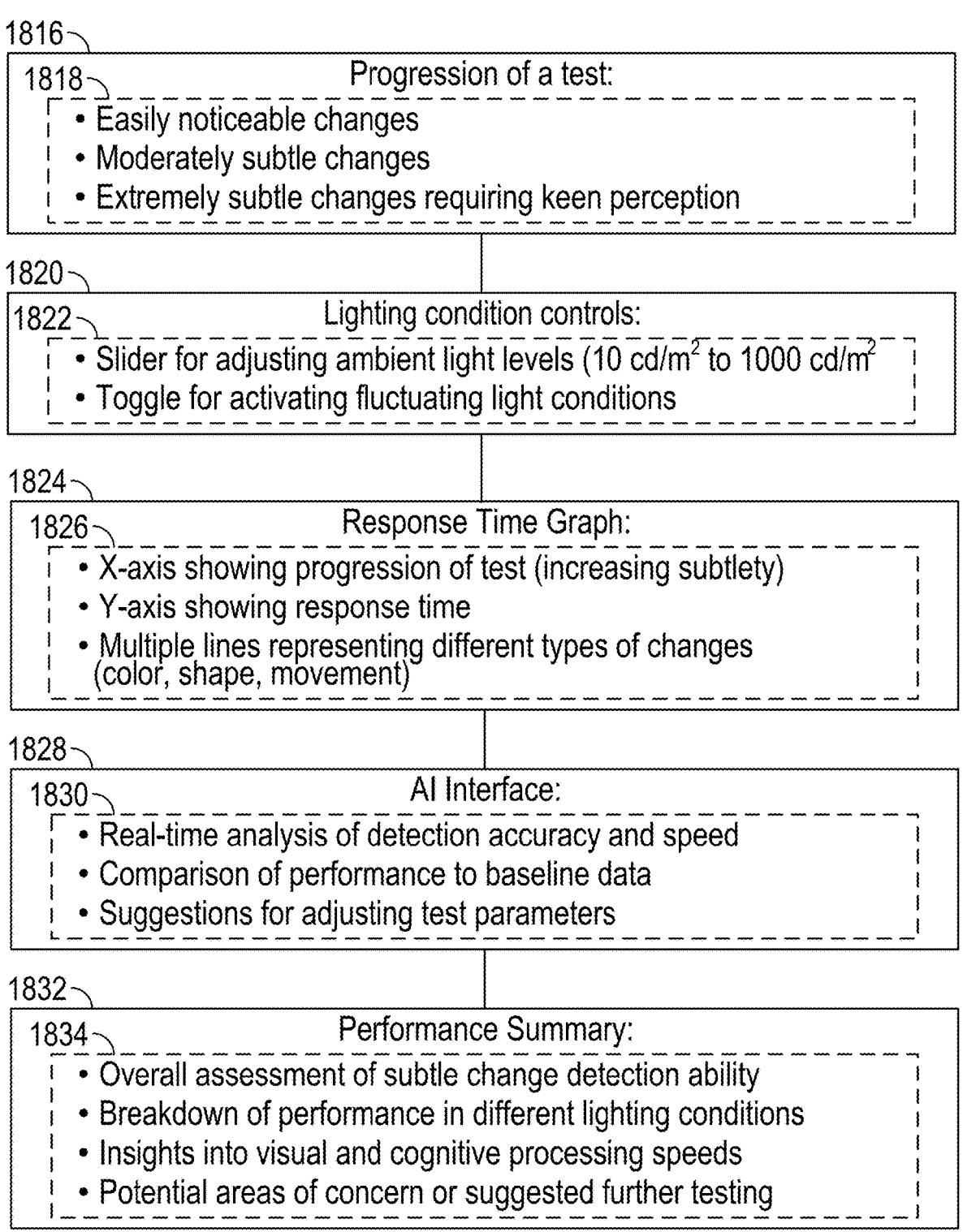

1816

1818                Progression of a test:
- Easily noticeable changes
- Moderately subtle changes
- Extremely subtle changes requiring keen perception

1820

1822                Lighting condition controls:
- Slider for adjusting ambient light levels (10 cd/m$^2$ to 1000 cd/m$^2$
- Toggle for activating fluctuating light conditions

1824

1826                Response Time Graph:
- X-axis showing progression of test (increasing subtlety)
- Y-axis showing response time
- Multiple lines representing different types of changes (color, shape, movement)

1828

1830                AI Interface:
- Real-time analysis of detection accuracy and speed
- Comparison of performance to baseline data
- Suggestions for adjusting test parameters

1832

1834                Performance Summary:
- Overall assessment of subtle change detection ability
- Breakdown of performance in different lighting conditions
- Insights into visual and cognitive processing speeds
- Potential areas of concern or suggested further testing

FIG. 18D

METHODS AND SYSTEMS FOR IMPLEMENTING VIRTUAL VISION TEST FOR NIGHT VISION AND GLARE SENSITIVITY

TECHNICAL FIELD

The present inventions relate to vision test technology. More specifically, methods, systems, devices, and non-statutory computer-readable storage media are applied to implement vision testing in an extended reality environment.

BACKGROUND

Traditional visual assessment methods have been the cornerstone of evaluating eye health and vision for many years. These methods are typically conducted in clinical environments, where specialized equipment and standardized procedures are used to ensure accurate and reliable results. The parameters for these assessments are generally fixed, reflecting the controlled nature of the clinical setting.

Over time, these techniques have become the accepted standard for diagnosing and monitoring visual conditions, forming the basis of routine eye care practices in medical offices, hospitals, and specialized eye care facilities. Despite their widespread use, these methods have traditionally been limited to professional settings, where they can be conducted under the supervision of trained healthcare providers using dedicated equipment.

SUMMARY

The present disclosure relates to innovative methods and systems that can revolutionize vision care, making vision testing and other exams more accessible and affordable for patients. Additionally, it is contemplated that the principles and features of the present disclosure can be implemented in numerous other applications of display technology, including headsets, heads-up displays, and other micro-displays (e.g., microLED and microOLED) to address challenges and limitations inherent in such products and their uses.

In accordance with at least some embodiments disclosed herein is the realization that traditional methods for visual assessment do not allow for dynamic adjustment of test parameters, leading to less accurate assessments, nor can they be implemented to test eyes and vision at home using household devices in a consistent and environment-locked manner.

Some embodiments are directed to a method of implementing a virtual vision test at an electronic device including a head-mounted display (HMD) and a camera. The method includes executing a user application configured to enable the virtual vision test; generating a virtual reality (VR) user interface corresponding to a three-dimensional (3D) virtual environment; focusing the camera on an eye area of a user wearing the electronic device; displaying, on the user interface, a visual stimulus corresponding to the virtual vision test; while displaying the visual stimulus, in real time, capturing a sequence of eye images using the camera of the electronic device; determining eye movement information including a temporal sequence of eyeball positions based on the sequence of eye images; and comparing the visual stimulus and the eye movement information to determine an eye health condition.

In some embodiments, a user application can be implemented by a head-mounted display device (HDD) configured to create a customized extended reality (XR) environment for a user engaged on an XR information platform. Products may be rendered for the user in a three-dimension format in the XR environment, thereby facilitating eyewear selection and fitting. The XR can be an umbrella term encapsulating Augmented Reality (AR), Virtual Reality (VR), Mixed Reality (MR), and everything in between. In this application, any embodiments that apply a VR system can be implemented using an AR or MR system as well.

Some embodiments are directed to a method of implementing a virtual vision test for evaluating night vision and glare sensitivity. The method is performed at an electronic device including a HMD and a camera. The method includes generating a virtual reality (VR) user interface corresponding to a photorealistic virtual environment. The method also includes rendering the VR user interface on the HMD. The method also includes simulating one or more dynamic lighting scenarios in the VR user interface. The method also includes, while simulating the one or more dynamic lighting scenarios, in real time: continuously tracking, using the camera, eye movements and response times in response to visual stimuli presented in the one or more dynamic lighting scenarios; and evaluating user response based on the eye movements and the response times for testing night vision and glare sensitivity.

Some embodiments are directed to a method of implementing a virtual vision test for measuring pupil reaction to light changes and visual imperfections in virtual environments. The method is performed at an electronic device including a head-mounted display and a camera. The method includes generating a virtual reality (VR) user interface corresponding to a photorealistic virtual environment. The method also includes rendering the VR user interface on the HMD. The method also includes simulating one or more dynamic lighting scenarios in the VR user interface. The method also includes, while simulating the one or more dynamic lighting scenarios, in real time: continuously tracking, using the camera, pupil data in response to visual stimuli presented in the one or more dynamic lighting scenarios; and measuring pupil reaction to light changes based on the pupil data.

Some embodiments are directed to a method of implementing a virtual vision test for evaluating response time in detecting subtle visual changes under varying light conditions. The method is performed at an electronic device including a head-mounted display and a camera. The method includes generating a virtual reality (VR) user interface corresponding to a photorealistic virtual environment. The method also includes rendering the VR user interface on the HMD. The method also includes simulating one or more dynamic lighting scenarios in the VR user interface. The method also includes, while simulating the one or more dynamic lighting scenarios, in real time: continuously tracking, using the camera, eye movements in response to visual stimuli presented in the one or more dynamic lighting scenarios; and evaluating response times in detecting subtle visual changes based on the eye movements.

Some embodiments are directed to a system for implementing a virtual vision test. The system includes a head-mounted display including a display, and one or more cameras. The system also includes one or more processors. The system also includes memory storing one or more programs configured to be executed by the one or more processors. The one or more programs includes instructions for a user interface module configured to generate a virtual reality (VR) user interface corresponding to a three-dimensional virtual environment. The one or more programs also includes instructions for a rendering module configured to render the VR user interface on the HMD, integrating VR user interface elements with the three-dimensional virtual environment. The one or more programs also includes instructions for a simulation module configured to simulate one or more dynamic lighting scenarios in the VR user interface, including generating and managing various real-world lighting conditions and their changes over time. The one or more programs includes instructions for a tracking module configured to, continuously track, using at least one of the one or more cameras, eye movements and response times in response to visual stimuli presented in the one or more dynamic lighting scenarios, and/or continuously moni-tor and record pupil data, including pupil dilation and constriction, in response to visual stimuli presented in the one or more dynamic lighting scenarios. The one or more programs includes instructions for an evaluation module configured to: evaluate user response based on the eye movements and the response times for testing night vision and glare sensitivity, measure pupil reaction to light changes based on the pupil data, and/or evaluate detection of subtle visual changes based on the eye movements.

In another aspect, a non-transitory computer readable storage medium is provided, according to some embodi-ments. The medium stores one or more programs for execu-tion by one or more processors of a computer system, the one or more programs including instructions for performing any of the methods described herein.

In another aspect, an electronic device is provided, according to some embodiments. The electronic device includes an HMD, a camera, one or more processors, and memory for storing one or more programs for execution by the one or more processors, the one or more programs including instructions for performing any of the methods described herein.

Additional features and advantages of the subject tech-nology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exem-plary and explanatory and are intended to provide further explanation of the subject technology.

BRIEF DESCRIPTION OF THE FIGURES

Various features of illustrative embodiments of the inven-tions are described below with reference to the drawings. The illustrated embodiments are intended to illustrate, but not to limit, the inventions.

FIG. 3 is a block diagram of a computer system (e.g., including a headset device) configured to implement vision assessment or eyewear fitting, in accordance with some embodiments.

FIGS. 8A-8D include four diagrams of example graphical user interfaces rendered to determine a visual acuity score in a virtual environment created by a headset device, in accor-dance with some embodiments.

FIGS. 11A and 11B are diagrams showing an example vision test system, in accordance with some embodiments.

FIGS. 12A-12N show a flow diagram of an example process for implementing a virtual eye test for evaluating visual acuity and perception, according to some embodi-ments.

FIGS. 13A-13G show a flow diagram of an example process for implementing a virtual vision test for measuring pupil reaction to light changes and visual imperfections, according to some embodiments.

FIGS. 14A-14G show a flow diagram of an example process for implementing a virtual eye test for evaluating dynamic visual acuity, according to some embodiments.

FIG. 16D is a block diagram of example components for VR night vision and glare sensitivity test, according to some embodiments.

FIG. 17B is a block diagram of example components for VR pupil reaction to light changes test, according to some embodiments.

FIG. 18D shows a block diagram of example components for VR subtle visual changes detection test, according to some embodiments.

DETAILED DESCRIPTION

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for case of understanding.

Figure 1:
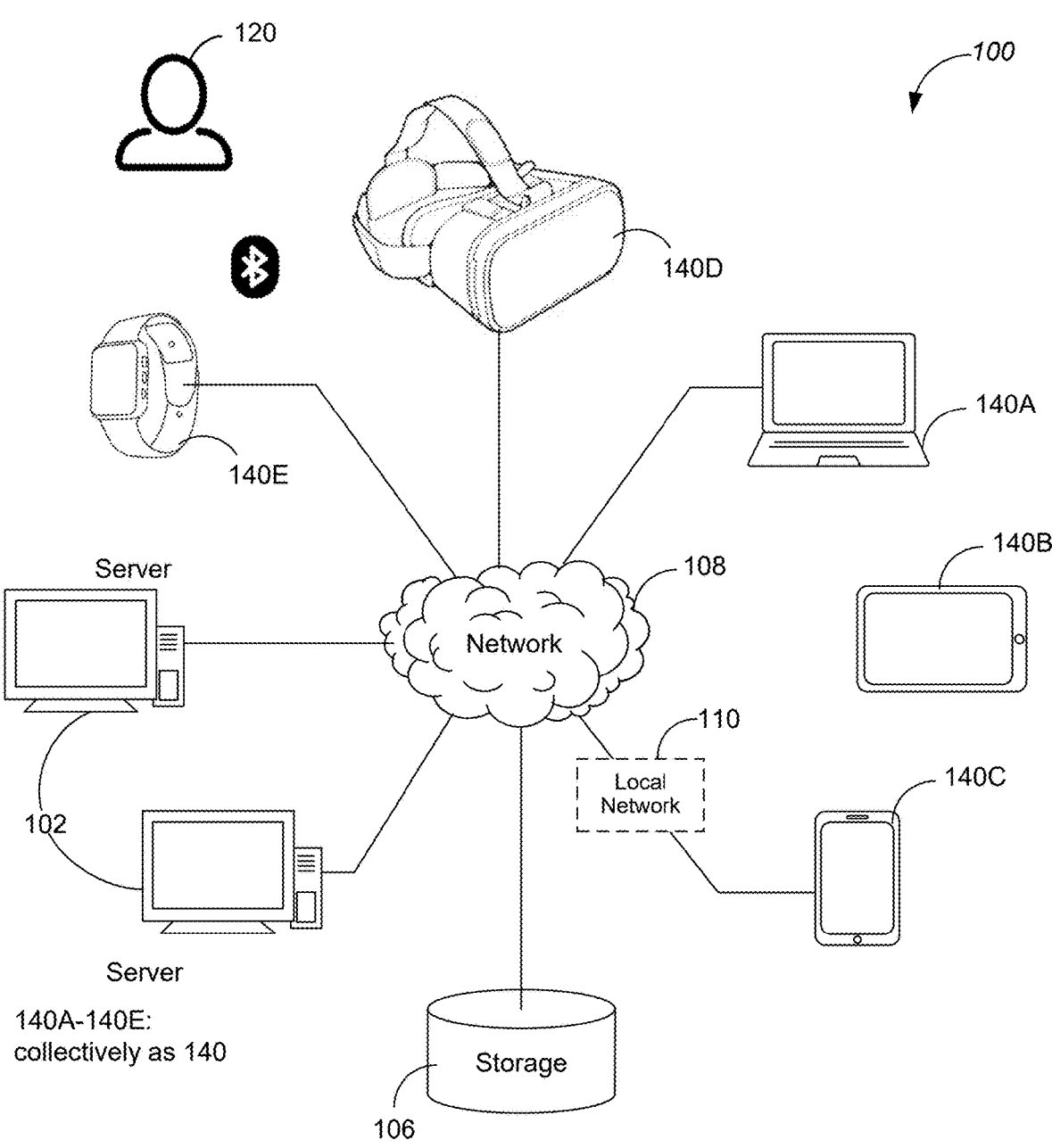
FIG. 1 is an example data processing environment having one or more servers communicatively coupled to one or more computer devices (e.g. includes an headset device), in accordance with some embodiments.

FIG. 1 is an example data processing environment 100 having one or more servers 102 communicatively coupled to one or more computer devices 140 (e.g., includes an headset device 140D), in accordance with some embodiments. The one or more computer devices 140 are electronic devices having computational capabilities, and may be, for example, desktop computers 140A, tablet computers 140B, mobile phones 140C, or intelligent, multi-sensing, network-connected home devices (e.g., a depth camera, a visible light camera). In some embodiments, the one or more computer devices 140 include a headset device 140D (also called a head-mounted display device 140D) configured to render extended reality content. In some embodiments, the one or more computer devices 140 include a wireless wearable device 140E (e.g., a smart watch, a fitness band) configured to track health data (e.g., heart rate, quality of sleep) and activity data (e.g., steps walked, stairs climbed) of a user wearing the device 140E. Each computer device 140 can collect data or user inputs, executes user applications, and present outputs on its user interface. The collected data or user inputs can be processed locally at the computer device 140 and/or remotely by the server(s) 102. The one or more servers 102 provides system data (e.g., boot files, operating system images, and user applications) to the computer devices 140, and in some embodiments, processes the data and user inputs received from the computer device(s) 140 when the user applications are executed on the computer devices 140. In some embodiments, the data processing environment 100 further includes a storage 106 for storing data related to the servers 102, computer devices 140, and applications executed on the computer devices 140. For example, storage 106 may store video content, static visual content, and/or audio data.

The one or more servers 102 can enable real-time data communication with the computer devices 140 that can be remote from each other or from the one or more servers 102. Further, in some embodiments, the one or more servers 102 can implement data processing tasks that are not completed locally by the computer devices 140. For example, the computer devices 140 include a game console (e.g., the headset device 140D) that executes an interactive online gaming application. The game console receives a user instruction and sends it to a game server 102 with user data. The game server 102 generates a stream of video data based on the user instruction and user data, and provides the stream of video data for display on the game console and other computer devices that can be engaged in the same game session with the game console.

The one or more servers 102, one or more computer devices 140, and storage 106 can be communicatively coupled to each other via one or more communication networks 108, which are the medium used to provide communications links between these devices and computers connected together within the data processing environment 100. The one or more communication networks 108 may include connections, such as wire, wireless communication links, or fiber optic cables. Examples of the one or more communication networks 108 include local area networks (LAN), wide area networks (WAN) such as the Internet, or a combination thereof. The one or more communication networks 108 are, optionally, implemented using any known network protocol includes various wired or wireless protocols, such as Ethernet, Universal Serial Bus (USB), FIRE-WIRE, Long Term Evolution (LTE), Global System for Mobile Communications (GSM), Enhanced Data GSM Environment (EDGE), code division multiple access (CDMA), time division multiple access (TDMA), Bluetooth, Wi-Fi, voice over Internet Protocol (VOIP), Wi-MAX, or any other suitable communication protocol. A connection to the one or more communication networks 108 may be established either directly (e.g., using 1G/4G connectivity to a wireless carrier), or through a network interface 110 (e.g., a router, switch, gateway, hub, or an intelligent, dedicated whole-home control node), or through any combination thereof. As such, the one or more communication networks 108 can represent the Internet of a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other electronic systems that route data and messages.

In some embodiments, the headset device 140D can be communicatively coupled to a data processing environment 100. The headset device 140D includes one or more cameras (e.g., a visible light camera, a depth camera), a microphone, a speaker, one or more inertial sensors (e.g., gyroscope, accelerometer), and a display. In some situations, the camera captures hand gestures of a user wearing the headset device 140D. In some situations, the microphone records ambient sound includes user's voice commands.

In some embodiments, the headset device 140D is communicatively coupled to one or more servers 102, and enables a centralized vision test management platform with the one or more servers 102. This vision test management platform may aggregate data (e.g., visual stimuli 338, sensor data 342, vision test results 344) from a plurality of user accounts associated with a plurality of users, analyze the aggregated data, and track vision health trends for individual users or user groups. In some embodiments, data are communicated between a headset device 140D and a server 102 in an encrypted format. In some embodiments, the vision test management platform is coupled to a global health database storing epidemiological data, and configured to cross-reference the data collected from its user accounts with the epidemiological data to identify an emerging pattern and a public health concern. For example, a teenager's vision data was collected and analyzed during an extended duration of time (e.g., 10 years) to identify an individual vision development trend, and cross-referenced with an average vision development trend extracted from the global health database. A doctor can rely on a cross-referencing result to determine whether the individual vision development trend is normal or whether the teenager's eyesight drops faster than average teenagers. As such, various embodiments of the vision test management platform integrates biometric data and global health analytics and provides a secure, personalized, and interactive environment for vision testing, which improves precision and user experience of vision assessments and contributes to broader public health monitoring and research initiatives.

Figure 2:
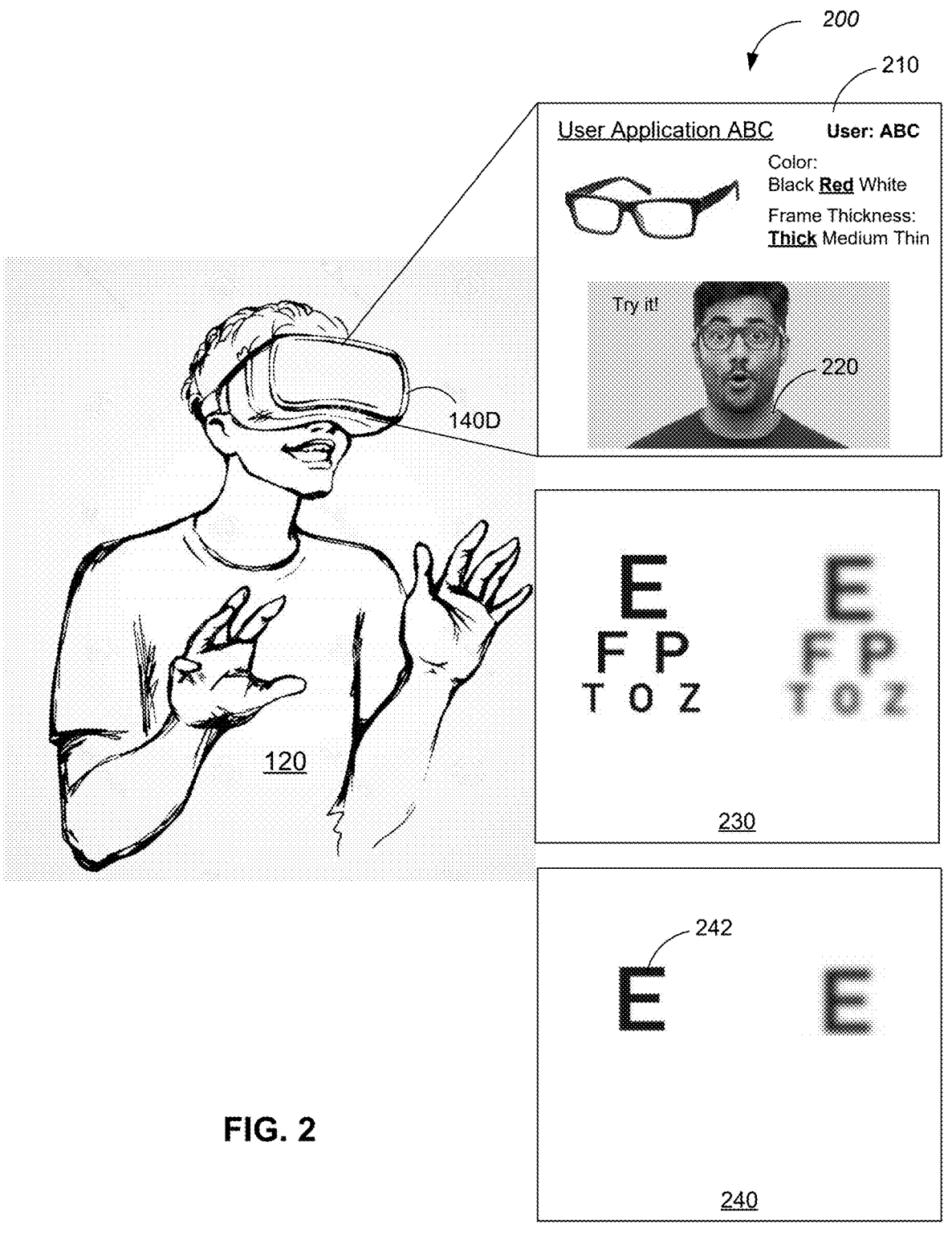
FIG. 2 is an environment in which a computer device (e.g., a headset device) is applied to facilitate visual assess-ment or eyewear fitting, in accordance with some embodi-ments.

FIG. 2 is an environment 200 in which a computer device 140 (e.g., a headset device 140D) is applied to facilitate visual assessment or eyewear fitting, in accordance with some embodiments. The XR headset device 140D may be communicatively coupled within the data processing environment 100. The XR headset device 140D may include one or more cameras (e.g., a visible light camera, a depth camera), a microphone, a speaker, one or more inertial sensors (e.g., gyroscope, accelerometer), and a display. In some situations, the camera captures hand gestures of a user wearing the XR headset device 140D. In some situations, the microphone records ambient sound includes user's voice commands. The XR headset device 140D may execute a client-side eyewear fitting application 326 or a client-side visual assessment application 328 (FIG. 3) via a user account associated with a user 120 (e.g., an optometrist user, an optician user, a patient user). In some embodiments, a computer device 140 (e.g., a mobile phone 140C) distinct from the XR headset device 140D can be used to implement the client-side eyewear fitting application 326 or visual assessment application 328 (FIG. 3).

In some embodiments, a first user interface 210 can be displayed on a computer device 140 (e.g., the headset device 140D) associated with the user 120. In some embodiments, an eyewear can be tried on or displayed as being worn by a 2D or 3D image 220 of the user 120. The server 102 or computer device 140 receives, from the first user interface 210, a user feedback message indicating an issue, requesting further improvement, or confirming a fit. In some embodiments, a second user interface 230 can be displayed on a computer device 140 associated with the user 120. The second user interface 230 includes a plurality of optotypes (e.g., six optotypes E, F, P, T, O, and Z) having different sizes. In some embodiments, a third user interface 240 can be displayed on a computer device 140 associated with the user 120. The second user interface 230 can display a temporal sequence of optotypes having respective sizes. Each optotype of a corresponding size can be displayed at one time.

FIG. 3 is a block diagram of a computer system 300 (e.g., including a headset device 140D, a server, or a combination thereof) configured to implement vision assessment or eyewear fitting, in accordance with some embodiments. The computer system 300 typically, includes one or more processing units (CPUs) 302, one or more network interfaces 304, memory 306, and one or more communication buses 308 for interconnecting these components (sometimes called a chipset). The computer system 300 includes one or more input devices 310 that facilitate user input, such as a keyboard, a mouse, a voice-command input unit or microphone, a touch screen display, a touch-sensitive input pad, a gesture capturing camera, or other input buttons or controls. Furthermore, in some embodiments, the computer device 140 of the computer system 300 uses a microphone for voice recognition or an eye tracking camera 366 for tracking eyeball movement. In some embodiments, the computer device 140 includes one or more optical cameras (e.g., an RGB camera), scanners, or photo sensor units for capturing images. The computer system 300 also includes one or more output devices 312 that enable presentation of user interfaces 210 and display content includes one or more speakers and/or one or more visual displays.

The computer system 300 includes one or more sensors 360, which further includes one or more of: a plurality of electrodes 362, one or more depth sensing sensors 364, one or more eye tracking cameras 366, a biometric sensor array 368, one or more infrared sensors 370, one or more ultrasonic sensors 372, one or more ambient sensors 374, one or more motion sensors (e.g., six degree of freedom (6DOF) position and motion sensors 376, one or more outward camera 378, and one or more directional microphones 380. It is noted that the one or more sensors 360 are also included in the input device 310 and used to collect data to the computer system 300.

Memory 306 includes high-speed random-access memory, such as DRAM, SRAM, DDR RAM, or other random-access solid state memory devices; and, optionally, includes non-volatile memory, such as one or more magnetic disk storage devices, one or more optical disk storage devices, one or more flash memory devices, or one or more other non-volatile solid state storage devices. Memory 306, optionally, includes one or more storage devices remotely located from one or more processing units 302. Memory 306, or alternatively the non-volatile memory within memory 306, includes a non-transitory computer readable storage medium. In some embodiments, memory 306, or the non-transitory computer readable storage medium of memory 306, stores the following programs, modules, and data structures, or a subset or superset thereof:

Operating system 314 including procedures for handling various basic system services and for performing hardware dependent tasks;

Network communication module 316 for connecting each server 102 or computer device 140 to other devices (e.g., server 102, computer device 140, or storage 106) via one or more network interfaces 304 (wired or wireless) and one or more communication networks 108, such as the Internet, other wide area networks, local area networks, metropolitan area networks, and so on;

User interface module 318 for enabling presentation of information (e.g., a graphical user interface for application(s) 324, widgets, websites and web pages thereof, and/or games, audio and/or video content, text, etc.) at each computer device 140 via one or more output devices 312 (e.g., displays, speakers, etc.);

Input processing module 320 for detecting one or more user inputs or interactions from one of the one or more input devices 310 and interpreting the detected input or interaction;

Web browser module 322 for navigating, requesting (e.g., via HTTP), and displaying websites and web pages thereof includes a web interface for logging into a user account associated with a computer device 140 or another electronic device, controlling the computer device if associated with the user account, and editing and reviewing settings and data that are associated with the user account;

One or more user applications 324 for execution by the computer system 300 (e.g., games, social network applications, smart home applications, extended reality application, and/or other web or non-web-based applications for controlling another electronic device and reviewing data captured by such devices), where in some embodiments, an eyewear fitting application 326 can be executed to implement eyewear fitting, and has a plurality of user accounts associated with a plurality of users 120 (e.g., technician users and eyewear users), and in some embodiments, a visual assessment application 328 can be executed to evaluate eyesight of a patient user, and has a plurality of user accounts associated with a plurality of users 120 (e.g., an optometrist user, a patient user);

Data processing module 330 for processing data associated with the user applications 324, e.g., using machine learning models 350;

Model training Module 332 for obtaining training data 346 and training machine learning models 350; and One or more databases 340 for storing at least data including one or more of:

Device settings 334 including common device settings (e.g., service tier, device model, storage capacity, processing capabilities, communication capabilities, etc.) of the computer system 300;

User account information 336 for the one or more user applications 324, e.g., user names, security questions, account history data, user preferences, and predefined account settings, where in some embodiments, the user account information 336 includes facial measurements and one or more virtual fitting parameters associated with associated with a user account of an eye fitting application 326, and in some embodiments, the user account information 336 includes visual stimuli 338, sensor data 342, and vision test results 344 associated with a user account of a visual assessment application 328; and Machine learning models 350 including parameters (e.g., weights, biases) used to implement vision test or select eyewear for eyewear users.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, modules or data structures, and thus various subsets of these modules may be combined or otherwise re-arranged in various embodiments. In some embodiments, memory 306, optionally, stores a subset of the modules and data structures identified above. Furthermore, memory 306, optionally, stores additional modules and data structures not described above.

Figure 4:
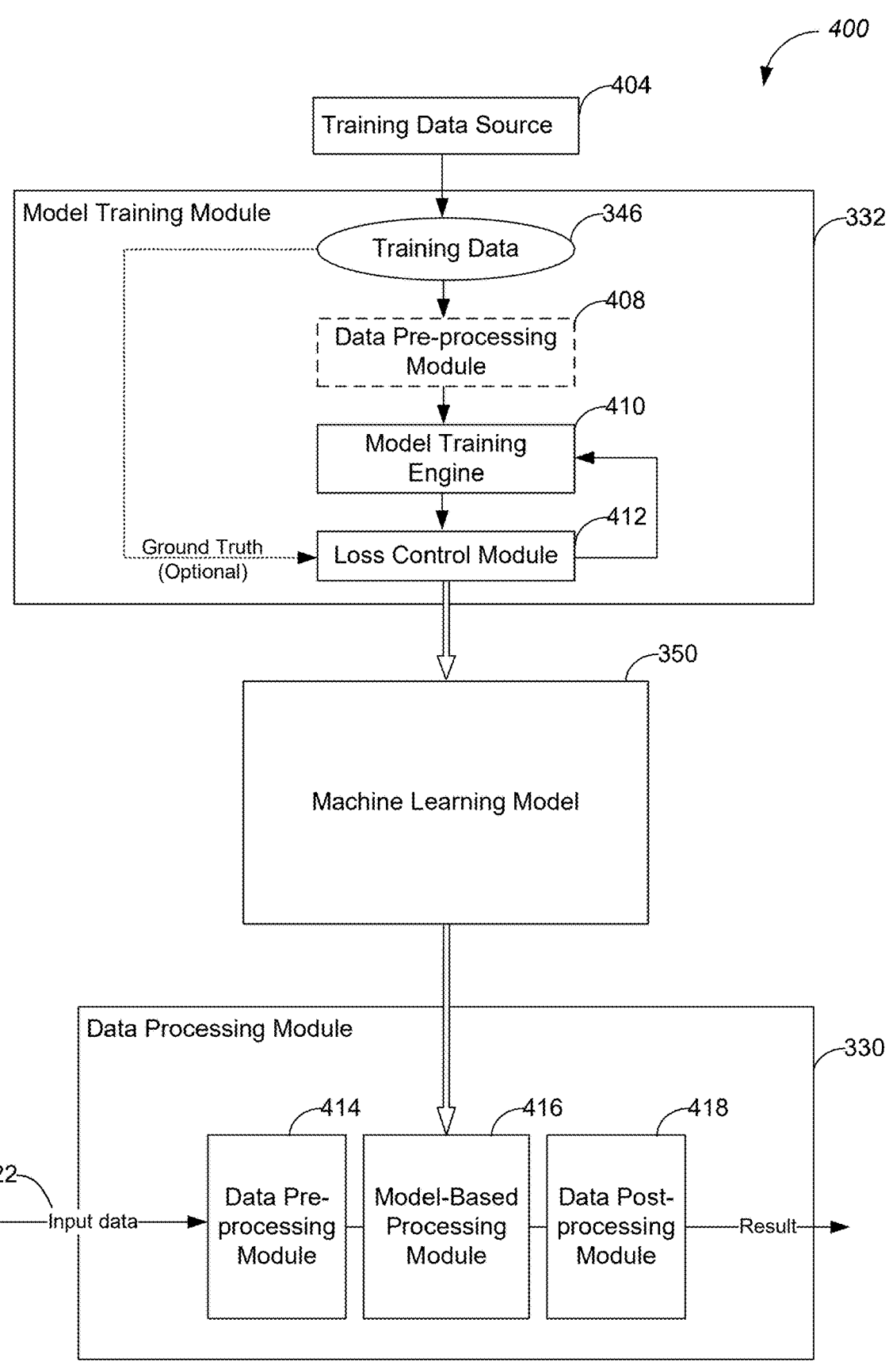
FIG. 4 is a block diagram of a machine learning system for training and applying machine learning models (e.g., for glass making), in accordance with some embodiments.

FIG. 4 is a block diagram of a machine learning system 400 for training and applying machine learning models 350 (e.g., for glass making), in accordance with some embodiments. The machine learning system 400 includes a model training module 332 establishing one or more machine learning models 350 and a data processing module 330 for processing input data 422 using the machine learning model 350. In some embodiments, both the model training module 332 and the data processing module 330 are located within a computer device 140 (e.g., a VR headset), while a training data source 404 provides training data 346 to the computer device 140. In some embodiments, the training data source 404 is the data obtained from the computer device 140 itself, from a server 102, from storage 106, or from another electronic device or computer device 140. Alternatively, in some embodiments, the model training module 332 is located at a server 102, and the data processing module 330 is located in a computer device 140. The server 102 trains the machine learning model 350 and provides the trained models 350 to the computer device 140 to process real-time input data 422 detected by the computer device 140. In some embodiments, the training data 346 provided by the training data source 404 include a standard dataset widely used to train machine learning models 350. The input data 422 further includes sensor data. Further, in some embodiments, a subset of the training data 346 is modified to augment the training data 346. The subset of modified training data is used in place of or jointly with the subset of training data 346 to train the machine learning models 350.

In some embodiments, the model training module 332 includes a model training engine 410, and a loss control module 412. Each machine learning model 350 is trained by the model training engine 410 to process corresponding input data 422 to implement a respective task. Specifically, the model training engine 410 receives the training data 346 corresponding to a machine learning model 350 to be trained, and processes the training data to build the machine learning model 350. In some embodiments, during this process, the loss control module 412 monitors a loss function comparing the output associated with the respective training data item to a ground truth of the respective training data item. In these embodiments, the model training engine 410 modifies the machine learning models 350 to reduce the loss, until the loss function satisfies a loss criteria (e.g., a comparison result of the loss function is minimized or reduced below a loss threshold). The machine learning models 350 are thereby trained and provided to the data processing module 330 of a computer device 140 to process real-time input data 422 from the computer device 140.

In some embodiments, the model training module 402 further includes a data pre-processing module 408 configured to pre-process the training data 346 before the training data 346 is used by the model training engine 410 to train a machine learning model 350. For example, an image pre-processing module 408 is configured to format patients' eye images in the training data 346 into a predefined image format. For example, the preprocessing module 408 may normalize the images to a fixed size, resolution, or contrast level. In another example, an image pre-processing module 408 extracts a region of interest (ROI) corresponding to an eye area.

In some embodiments, the model training module 332 uses supervised learning in which the training data 346 is labelled and includes a desired output for each training data item (also called the ground truth in some situations). In some embodiments, the desirable output is labelled manually by people or labelled automatically by the model training model 332 before training. In some embodiments, the model training module 332 uses unsupervised learning in which the training data 346 is not labelled. The model training module 332 is configured to identify previously undetected patterns in the training data 346 without pre-existing labels and with little or no human supervision. Additionally, in some embodiments, the model training module 332 uses partially supervised learning in which the training data is partially labelled.

In some embodiments, the data processing module 330 includes a data pre-processing module 414, a model-based processing module 416, and a data post-processing module 418. The data pre-processing modules 414 pre-processes input data 422 based on the type of the input data 422. In some embodiments, functions of the data pre-processing modules 414 are consistent with those of the pre-processing module 408, and convert the input data 422 into a predefined data format that is suitable for the inputs of the model-based processing module 416. The model-based processing module 416 applies the trained machine learning model 350 provided by the model training module 332 to process the pre-processed input data 422. In some embodiments, the model-based processing module 416 also monitors an error indicator to determine whether the input data 422 has been properly processed in the machine learning model 350. In some embodiments, the processed input data is further processed by the data post-processing module 418 to create a preferred format or to provide additional information that can be derived from the processed input data. The data processing module 330 uses the processed input data to make eyewear glasses for a patient user.

Examples of the machine learning model 350 include, but are not limited to, an eye trajectory model, an eye position model, an ocular microtremor model, a response analysis model, a response analysis model, a biomedical data model, and medical information models.

Figures 5A, 5B:
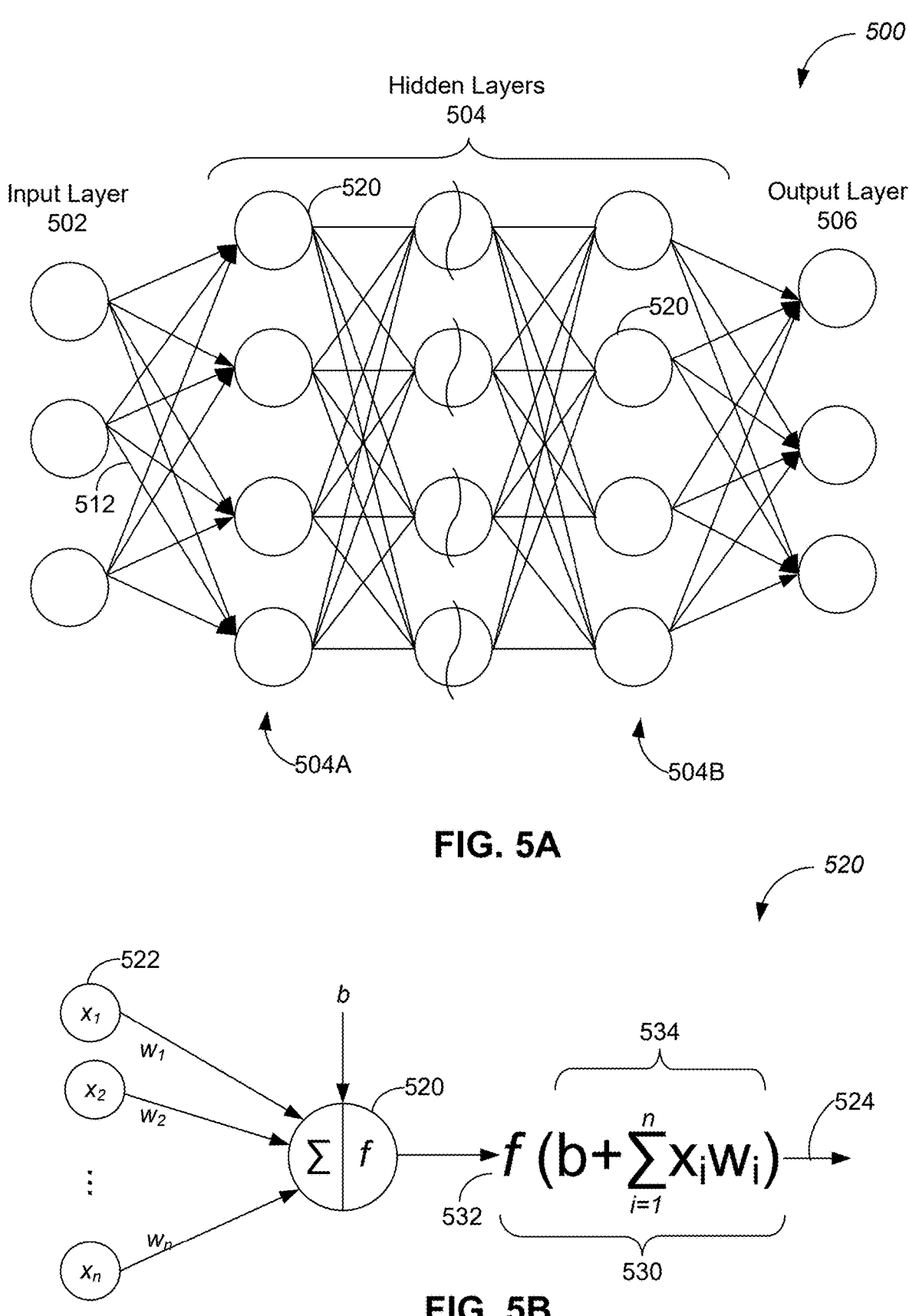
FIG. 5A is a structural diagram of an example neural network applied to process input data in a machine learning model, in accordance with some embodiments.
FIG. 5B is an example node in the neural network, in accordance with some embodiments.

FIG. 5A is a structural diagram of an example neural network 500 applied to process input data in a machine learning model 350, in accordance with some embodiments, and FIG. 5B is an example node 520 in the neural network 500, in accordance with some embodiments. It should be noted that this description is used as an example only, and other types or configurations may be used to implement the embodiments described herein. The machine learning model 350 is established based on the neural network 500. A corresponding model-based processing module 416 applies the machine learning model 350 including the neural network 500 to process input data 422 that has been converted to a predefined data format. The neural network 500 includes a collection of nodes 520 that are connected by links 512. Each node 520 receives one or more node inputs 522 and applies a propagation function 530 to generate a node output 524 from the one or more node inputs. As the node output 524 is provided via one or more links 512 to one or more other nodes 520, a weight w associated with each link 512 is applied to the node output 524. Likewise, the one or more node inputs 522 are combined based on corresponding weights $w_1$, $w_2$, $w_3$, and $w_4$ according to the propagation function 530. In an example, the propagation function 530 is computed by applying a non-linear activation function 532 to a linear weighted combination 534 of the one or more node inputs 522.

The collection of nodes 520 is organized into layers in the neural network 500. In general, the layers include an input layer 502 for receiving inputs, an output layer 506 for providing outputs, and one or more hidden layers 504 (e.g., layers 504A and 504B) between the input layer 502 and the output layer 506. A deep neural network has more than one hidden layer 504 between the input layer 502 and the output layer 506. In the neural network 500, each layer is only connected with its immediately preceding and/or immediately following layer. In some embodiments, a layer is a "fully connected" layer because each node in the layer is connected to every node in its immediately following layer. In some embodiments, a hidden layer 504 includes two or more nodes that are connected to the same node in its immediately following layer for down sampling or pooling the two or more nodes. In particular, max pooling uses a maximum value of the two or more nodes in the layer for generating the node of the immediately following layer.

In some embodiments, a convolutional neural network (CNN) is applied in a machine learning model 350 to process input data. The CNN employs convolution operations and belongs to a class of deep neural networks. The hidden layers 504 of the CNN include convolutional layers. Each node in a convolutional layer receives inputs from a receptive area associated with a previous layer (e.g., nine nodes). Each convolution layer uses a kernel to combine pixels in a respective area to generate outputs. For example, the kernel may be to a 3×3 matrix including weights applied to combine the pixels in the respective area surrounding each pixel. Video or image data is pre-processed to a predefined video/image format corresponding to the inputs of the CNN. In some embodiments, the pre-processed video or image data is abstracted by the CNN layers to form a respective feature map. In this way, video and image data can be processed by the CNN for video and image recognition or object detection.

In some embodiments, a recurrent neural network (RNN) is applied in the machine learning model 350 to process input data 422. Nodes in successive layers of the RNN follow a temporal sequence, such that the RNN exhibits a temporal dynamic behavior. In an example, each node 520 of the RNN has a time-varying real-valued activation. It is noted that in some embodiments, two or more types of input data are processed by the data processing module 330, and two or more types of neural networks (e.g., both a CNN and an RNN) are applied in the same machine learning model 350 to process the input data jointly.

The training process is a process for calibrating all of the weights wi for each layer of the neural network 500 using training data 346 that is provided in the input layer 502. The training process typically includes two steps, forward propagation and backward propagation, which are repeated multiple times until a predefined convergence condition is satisfied. In the forward propagation, the set of weights for different layers are applied to the input data and intermediate results from the previous layers. In the backward propagation, a margin of error of the output (e.g., a loss function) is measured (e.g., by a loss control module 412), and the weights are adjusted accordingly to decrease the error. The activation function 532 can be linear, rectified linear, sigmoidal, hyperbolic tangent, or other types. In some embodiments, a network bias term b is added to the sum of the weighted outputs 534 from the previous layer before the activation function 532 is applied. The network bias b provides a perturbation that helps the neural network 500 avoid over fitting the training data. In some embodiments, the result of the training includes a network bias parameter b for each layer.

Figure 6A:
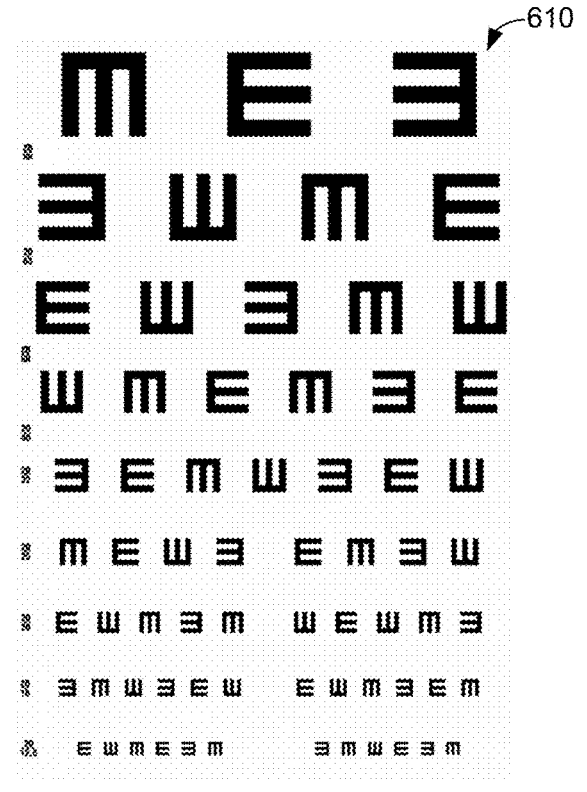
FIG. 6A is an example "tumbling E" chart applied in a visual acuity test.
Figure 6B:
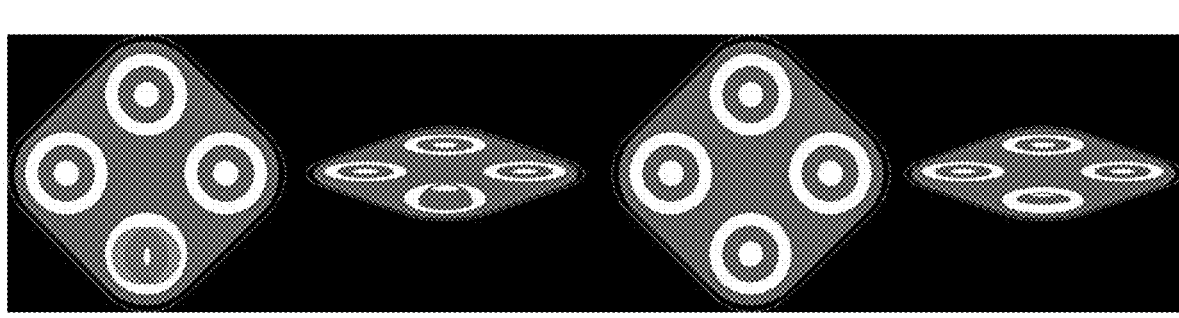
FIGS. 6B-6E are example patterns applied in an astigmatism test, a stereopsis test, a visual field test, and a color blindness test, in accordance with some embodiments.
Figure 6C:
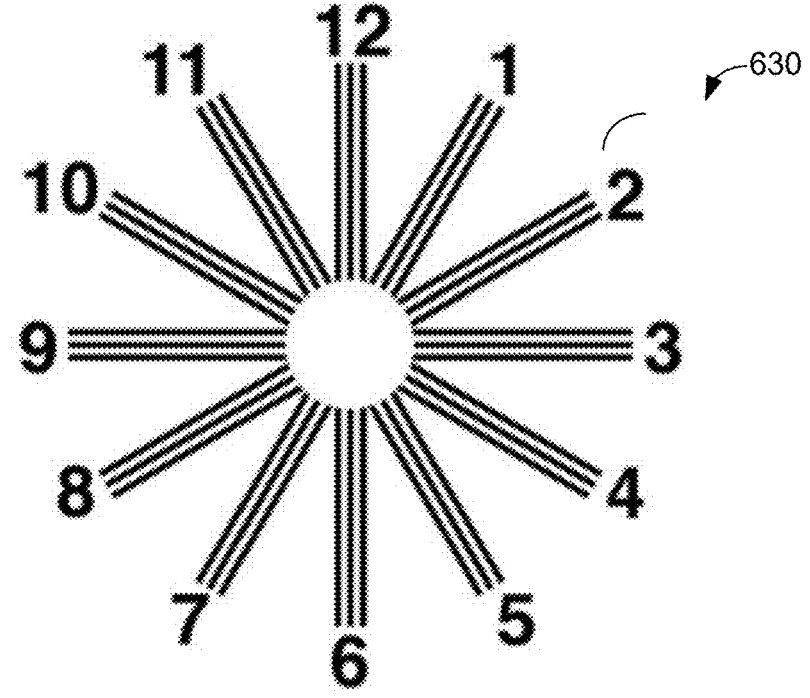
Figure 6D:
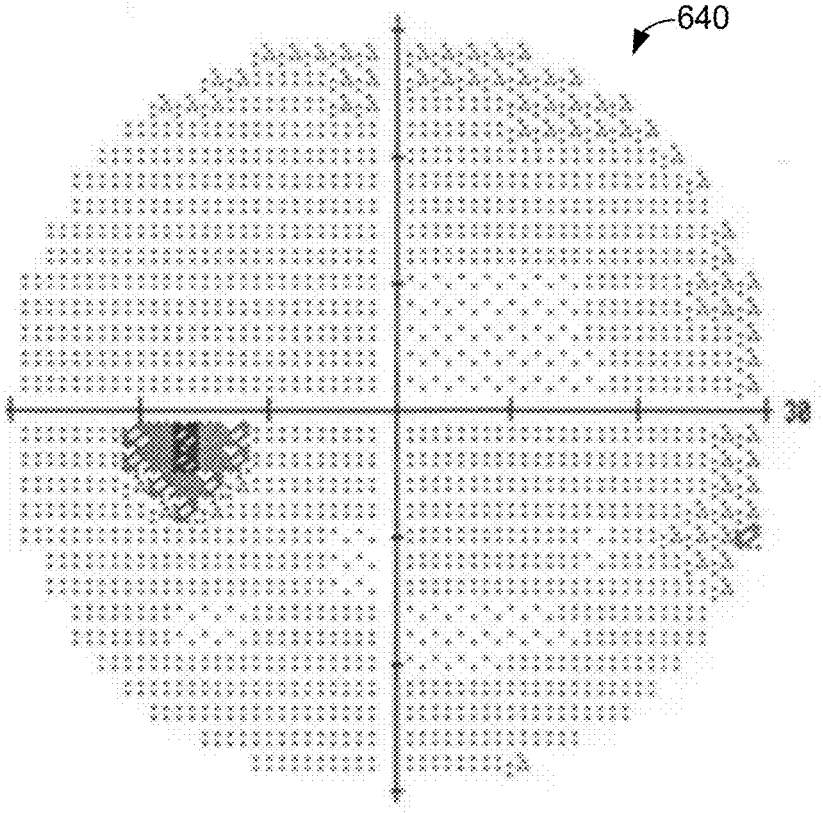
Figure 6E:
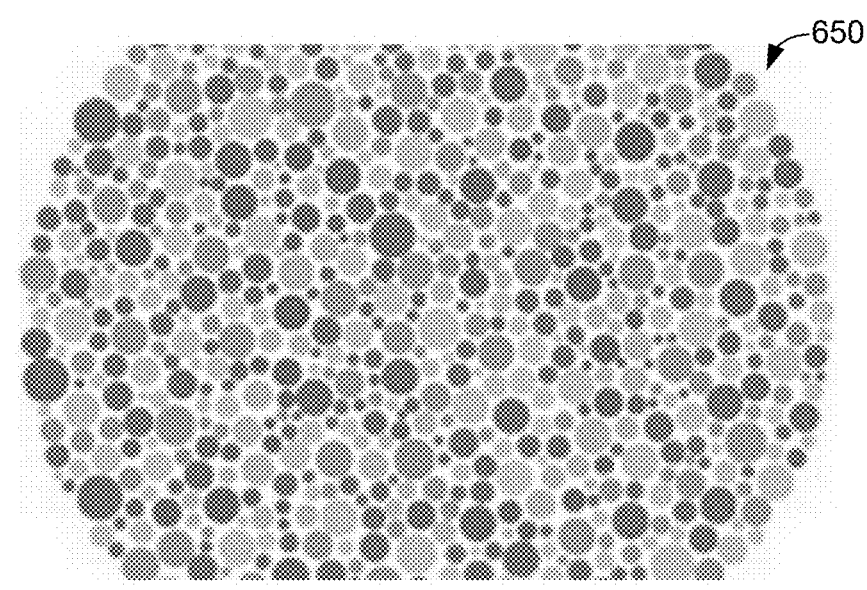

In some embodiments of the present disclosure, a vision test is implemented in a headset device 140D configured to display a user interface creating a three-dimensional (3D) virtual environment. Examples of a vision test implemented in the 3D virtual environment include, but are not limited to a visual acuity test, a visual field test, a visual depth test, a color blindness test, a retinoscopy, a test for stereopsis, a refraction test, an astigmatism test, and a contact lens exam. FIG. 6A is an example "tumbling E" chart 610 applied in a visual acuity test, in accordance with some embodiments. FIGS. 6B, 6C, 6D, and 6E are example patterns 620, 630, 640, and 650 applied in an astigmatism test, a stereopsis test, a visual field test, and a color blindness test, in accordance with some embodiments.

Figure 7:
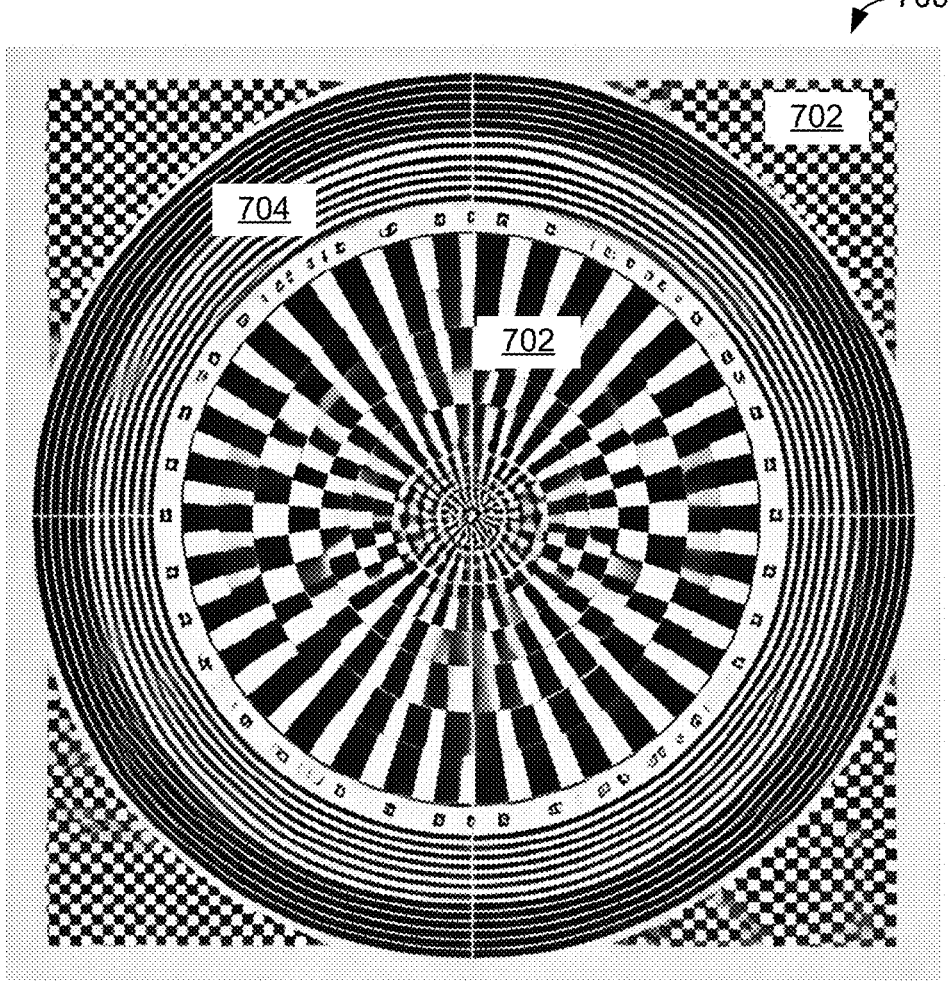
FIG. 7 is another example visual pattern applied to test visual acuity and astigmatism, in accordance with some embodiments.
Figure 8C:
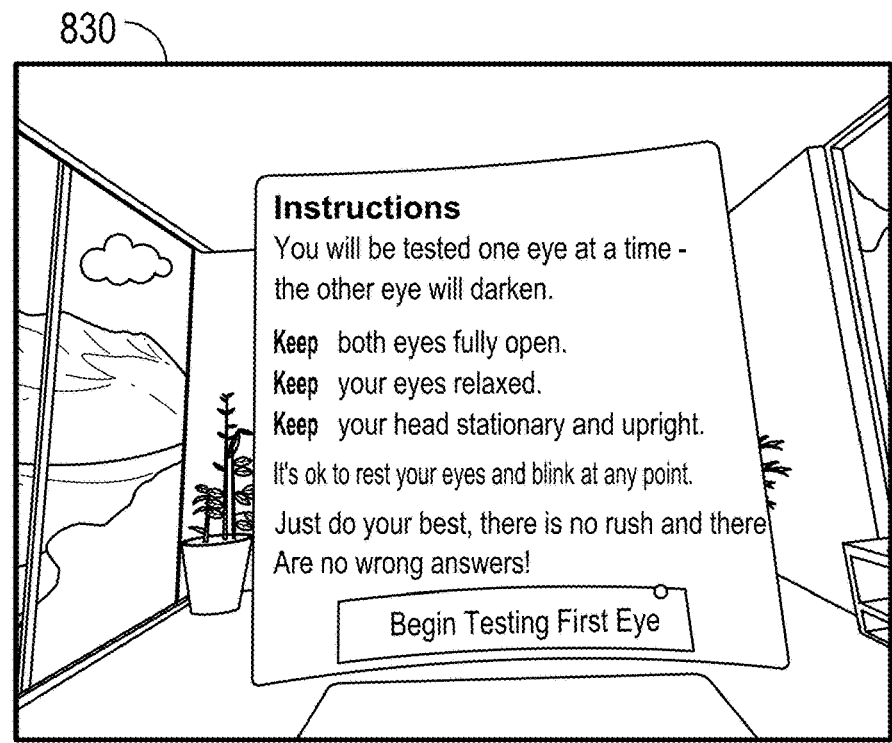
Figure 8D:
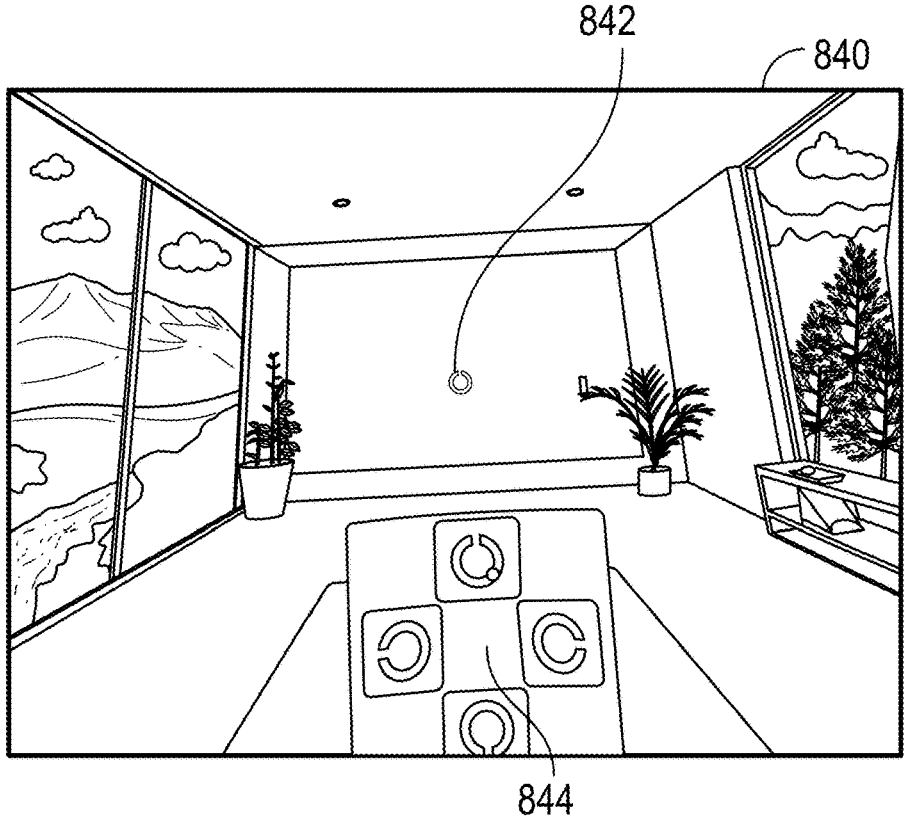

FIG. 7 is another example visual pattern 700 applied to test visual acuity and astigmatism, in accordance with some embodiments. The visual pattern 700 integrates a grid pattern 702 and concentric rings 704. The grid pattern 702 may include evenly spaced horizontal and vertical lines, creating a checkerboard pattern. The grid pattern 702 may be configured to identify distortions in straight lines, which can indicate issues with visual acuity and astigmatism. The concentric rings 704 may expand outward from a center of the visual pattern 700 and can assist in detecting radial distortions, which are common indicators of astigmatism.

The visual pattern 700 may be depicted in high-contrast black and white, which ensures maximum clarity and reduces the potential for color-related distortions, making it easier to detect any visual impairment or defect.

FIGS. 8A-8D include four diagrams of example graphical user interfaces 810, 820, 830, and 840 rendered to determine a visual acuity score in a virtual environment created by a headset device 140D, in accordance with some embodiments. The user interface 810 displays an information page including instructions on controlling a headset device 140D to select one of a plurality of optotype candidates to match a target optotype displayed in the virtual environment. The user interface 820 displays an information page including two optional ways of using the controller to select the one of the plurality of optotype candidates. The user interface 830 displays an information page including general guidelines on a visual acuity assessment process. The user interface 840 displays an optotype 842 that is projected on a screen that has a first distance L1 from a user's position in the virtual environment. In a second distance L2 near the user, a selection panel 844 including a plurality of optotype candidates is displayed, prompting the user to select one of the optotype candidates that matches the optotype 842. In some embodiments, in response to a user selection of the one of the optotype candidates, the optotype 842 displayed in the first distance L1 is updated with a new optotype 842. Further, in some embodiments, the new optotype 842 spins at a fast rate for a shortened duration of time (e.g., 2 seconds), before it settles in place of the original optotype 842. In an example, the optotype 842 spins and gradually shrinks in size during the shortened duration of time.

Figure 9A:
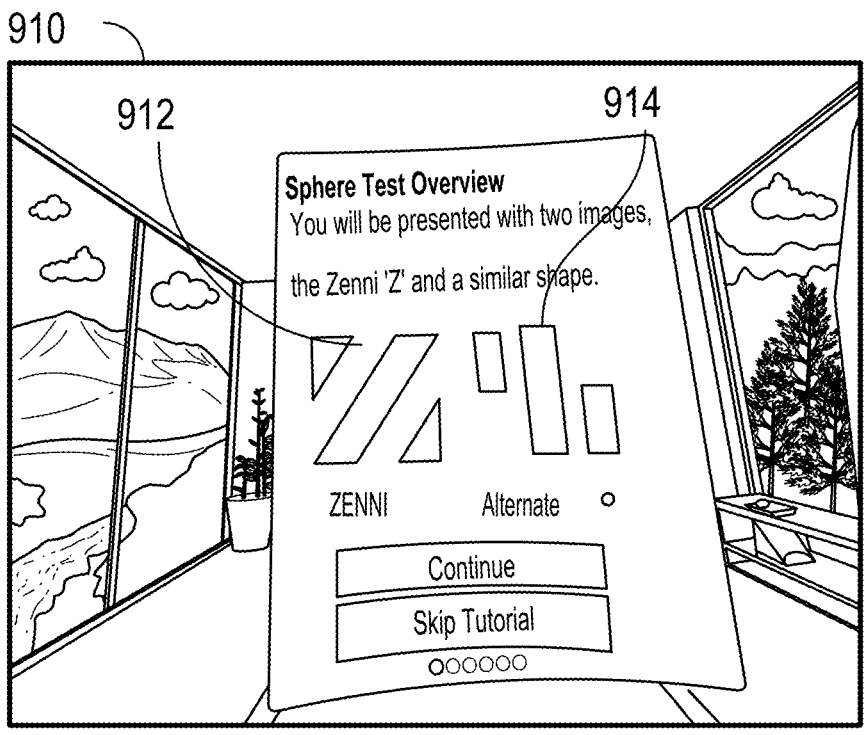
FIGS. 9A-9C include three diagrams of example graphi-cal user interfaces rendered to determine a nearsighted or farsighted power in a virtual environment created by a headset device, in accordance with some embodiments.
Figure 9B:
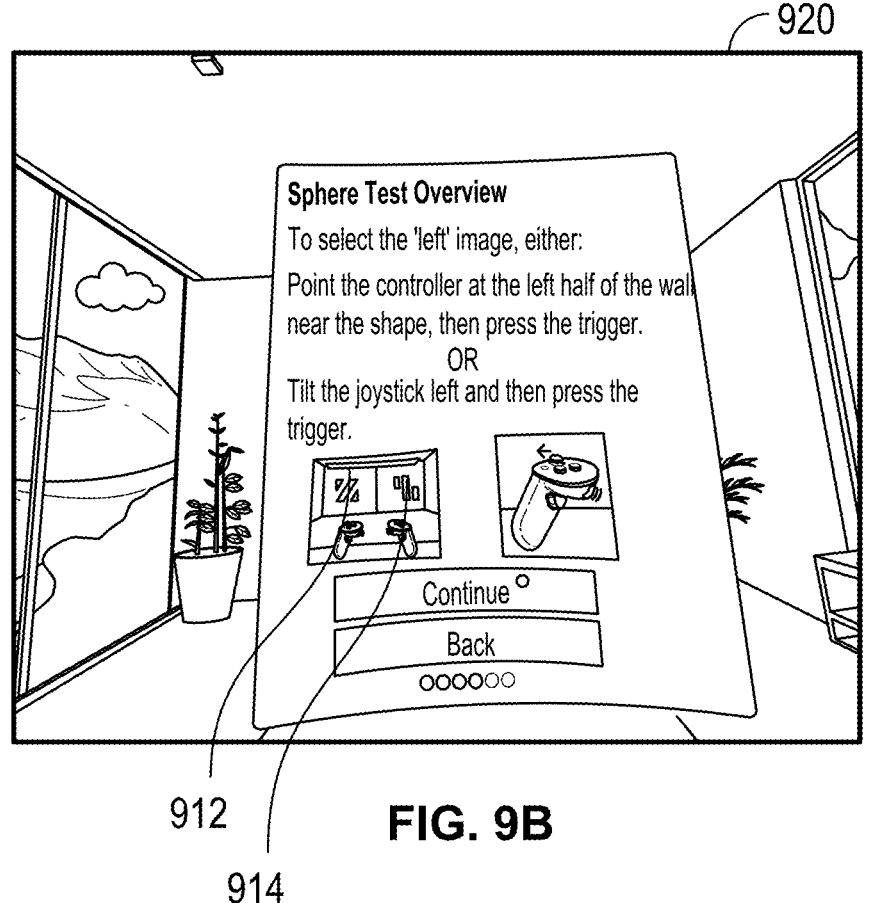
Figure 9C:
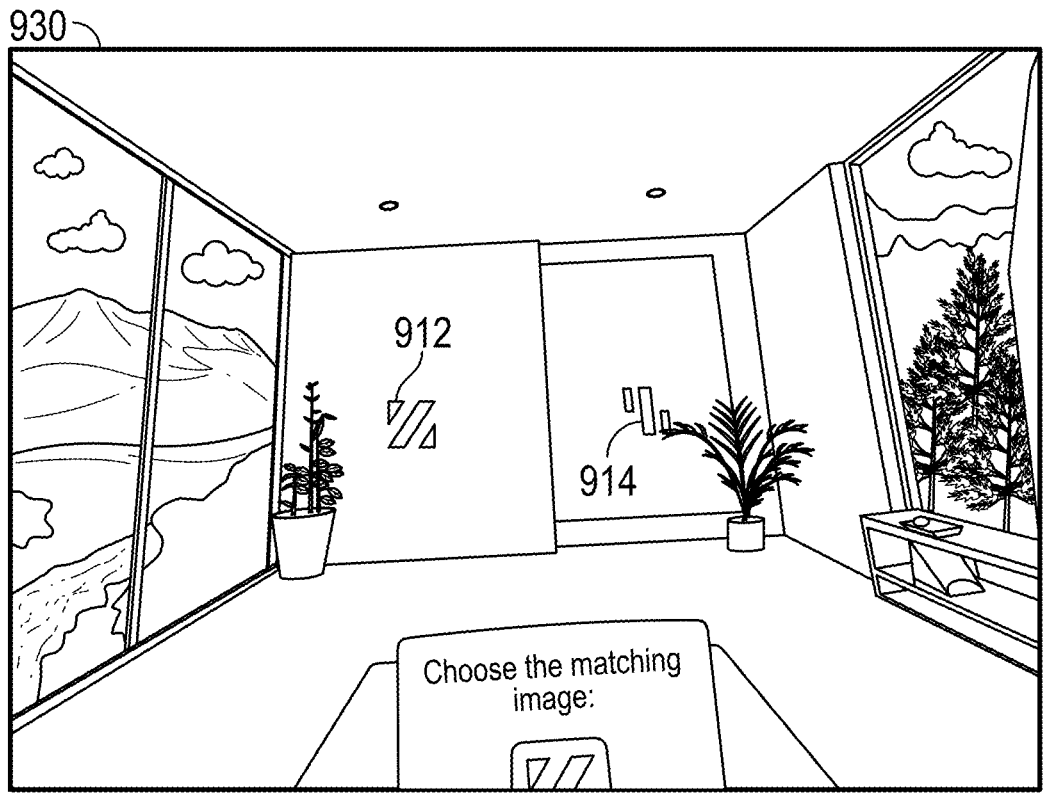
Figure 10A:
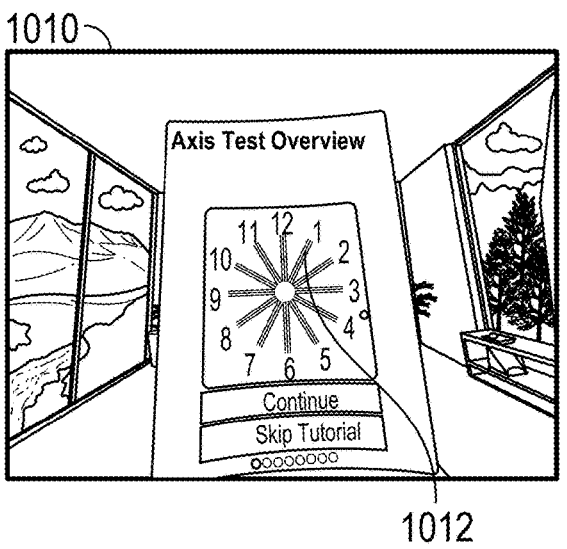
FIGS. 10A-10F include six diagrams of example graphi-cal user interfaces rendered to determine eye stigmatism in a virtual environment created by a headset device, in accor-dance with some embodiments.
Figure 10B:
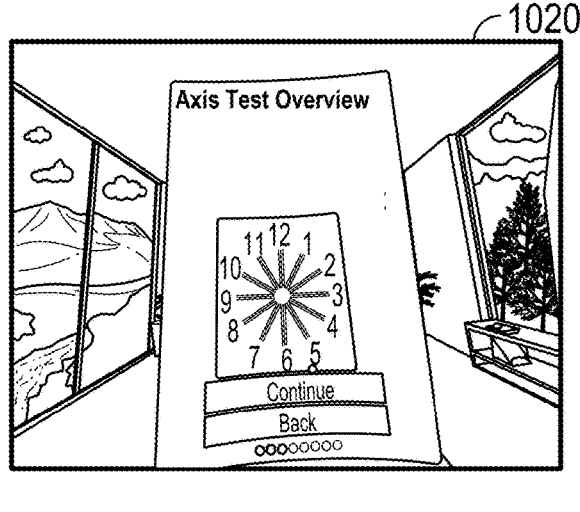
Figure 10C:
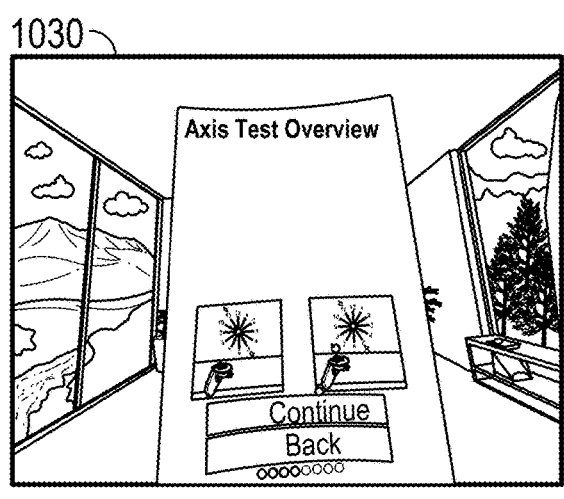
Figure 10D:
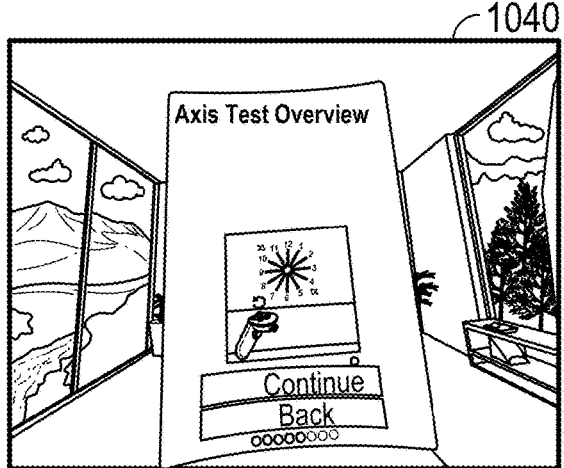
Figure 10E:
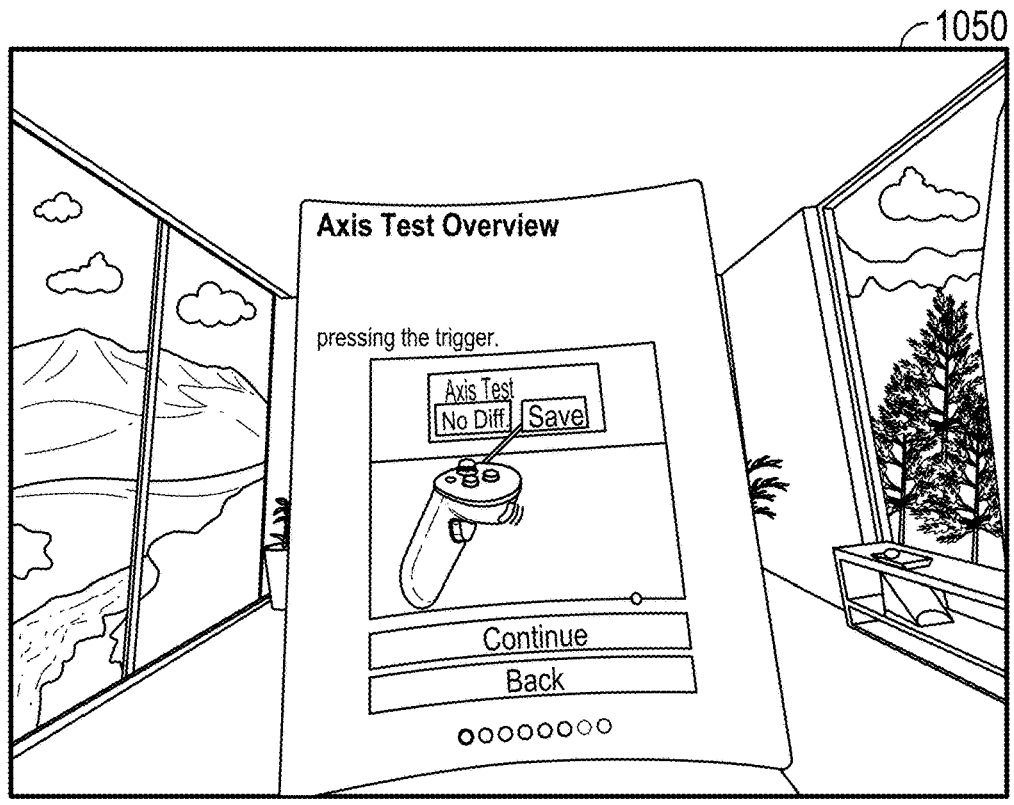
Figure 10F:
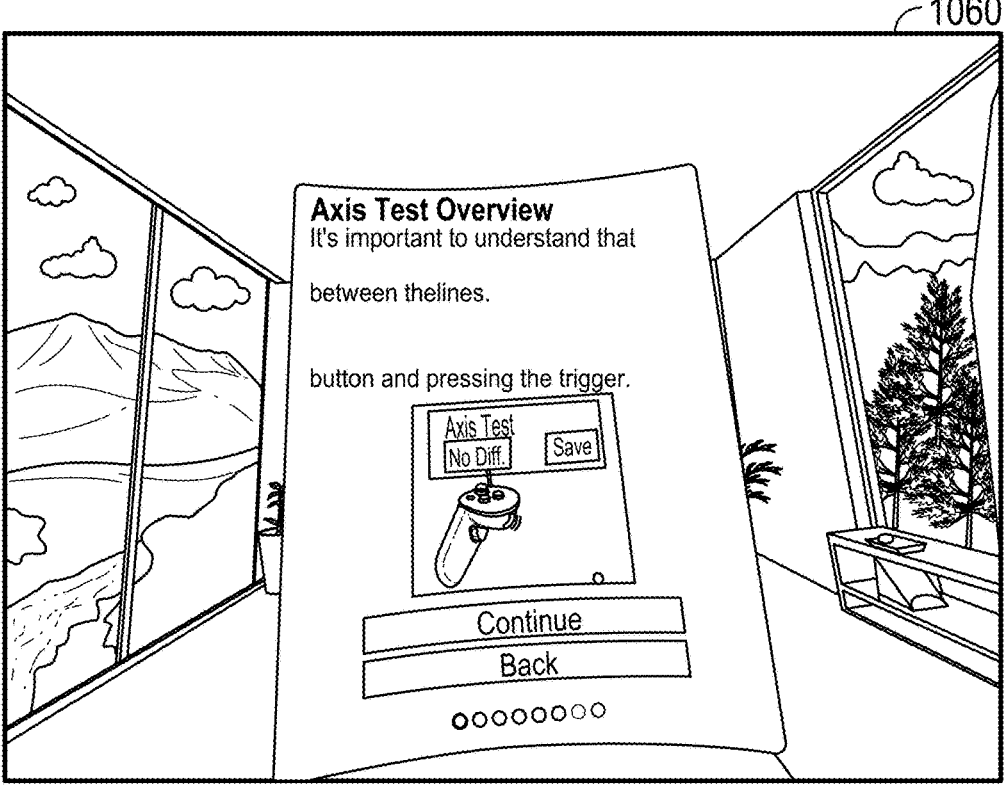

FIGS. 9A-9C include three diagrams of example graphical user interfaces 910, 920, and 930 rendered to determine a nearsighted or farsighted power in a virtual environment created by a headset device 140D, in accordance with some embodiments. The user interface 910 displays an information page explaining that two target optotypes 912 and 914 are displayed in the virtual environment. The user interface 920 displays an information page including two optional ways of using the controller to select one of the two target optotypes 912 and 914. The user interface 930 displays two target optotypes 912 and 914 that are projected on a screen that has a first distance L1 from a user's position in the virtual environment. In this example, the target optotype 912 located on the left is highlighted (e.g., by being displayed in a colored background). In a second distance L2 near the user, a confirmation panel 932 is displayed, prompting the user to select one of the two target optotypes 912 and 914. In some embodiments, in response to a user selection of the one of the two target optotypes 912 and 914, the two target optotypes 912 and 914 displayed in the first distance L1 is updated with a new pair of two target optotypes 912 and 914. Further, in some embodiments, each optotype 912 or 914 spins at a fast rate for a shortened duration of time (e.g., 2 seconds), before it settles in place of the original optotype 912 or 914. In an example, the optotype 912 or 914 spins and gradually shrinks in size during the shortened duration of time.

FIGS. 10A-10F include six diagrams of example graphical user interfaces 1010, 1020, 1030, 1040, 1050, and 1060 rendered to determine eye stigmatism in a virtual environment created by a headset device 140D, in accordance with some embodiments. The user interface 1010 displays an information page explaining that a clock diagram of converging numbered lines 1012 (which is a type of optotype) is displayed in the virtual environment. The user interface 1020 displays an information page explaining what is selected on the clock diagram of converging numbered lines 1012 displayed in the virtual environment. The user interface 1030 displays an information page including two optional ways of using the controller to select lines on the clock diagram of converging numbered lines 1012. The user interface 1040 displays an information page explaining a situation having equally clear lines on the clock diagram of converging numbered lines 1012. The user interface 1050 displays an information page including an instruction using the controller to submit a selection. The user interface 1060 displays an information page including an instruction using the controller to indicate that no difference is observed on the clock diagram of converging numbered lines 1012.

Some embodiments of a VR system are configured to enhance administration and experience of vision tests. The VR system includes a headset device 140D equipped with a display (sometimes referred to as a head-mounted display (HMD)). In some embodiments, the headset device 140D includes and one or more sensors for tracking one or more of eye movement, head orientation, and/or hand gestures of a user wearing the headset device 140D. In some embodiments, the headset device 140D is configured to execute a vision assessment application 328 configured to adaptively manage a sequence of vision tests based on the user's condition. In some embodiments, the headset device 140D is communicatively coupled to a server 102 configured to execute a server-side module for the vision assessment application 328, thereby managing the sequence of vision tests jointly with a device-side module of the vision assessment application 328 executed on the headset device. The vision assessment application 328 is configured to generate a virtual reality (VR) user interface corresponding to a three-dimensional (3D) virtual environment and render visual stimuli 338 in this 3D virtual environment. A range of different vision tests are conducted based on the visual stimuli within an immersive VR space.

In some embodiments, a headset device 140D includes one or more processors 302 and memory 306 storing instructions to execute the vision assessment application 328 for rendering visual stimuli 338 in an output device 312 (e.g., a display) and processing sensor data 342 collected from the sensors 360 in response to the visual stimuli 338. The sensor data 342 may be processed to determine vision test results 344 (e.g., eye movement patterns, response times, and visual perception accuracy) for the user. Further, in some embodiments, VR technology facilitates a personalized control scheme for navigating the vision tests. The personalized control scheme enables the user to interact with the test environment through intuitive hand gestures and eye movements, thereby providing a natural and engaging testing experience. The vision tests may be customized based on individual users' requirements and accommodate a wide range of vision impairments.

In some embodiments, the vision test results 344 are used to generate comprehensive reports on the user's visual performance. For example, the headset device 140D employs a deep learning model that correlates micro-expression data with vision test results 344 to provide holistic assessment of the user's ocular health. In some situations, the vision test results 344 are applied to identify vision conditions of the user and track changes of the vision conditions over time, thereby offering valuable insights to healthcare providers. In various embodiments of this application, eye images are captured and used to determine eye movement information automatically and without user intervention, which is an efficient solution to provide reliable supplemental information that cannot be provided by the user's active responses to visual stimuli.

Example Vision Test System

Figure 11A:
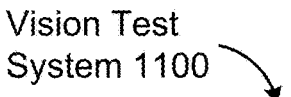

FIG. 11A is a diagram showing an example vision test system 1100, in accordance with some embodiments. The vision test system 1100 is implemented using a computer device (e.g., headset device 140D). The computer device includes one or more processors 1102, memory 1124 storing instructions to be implemented by the processor(s) 1102, a head-mounted display 1104, one or more network or other communications interfaces 1118, and one or more communication buses 1126 for interconnecting these and other optional components. The communication buses 1126 may include circuitry that interconnects and controls communications between system components. The HMD 1104 includes a display 1106 (e.g., one or more high-resolution screens), one or more lenses 1108 (to focus and/or shape display images), cameras and/or sensors 1112 (e.g., outward camera 378, eye-tracking camera 366), and/or a physical structure 1110 (e.g., a structure that holds the components and configured to be worn on a head). The HMD 1104 optionally includes audio devices 1114 and one or more processors 1116 (instead of or in addition to the processors 1102, to implement instructions in the memory 1124). One or more cameras and/or sensors 1128 may be optionally included in some embodiments, instead of or in addition to the cameras and/or sensors 1112 integrated within the HMD 1104. In some embodiments, the computer device also includes one or more input devices 1122 (e.g., controllers and/or hand-tracking sensors). In some embodiments, the computer device also includes a battery 1120 (e.g., for standalone headsets). In some embodiments, the input device/mechanism 1122 includes a keyboard. In some embodiments, the input device/mechanism 1122 includes a "soft" keyboard, which is displayed as needed on the display 1106, for example, to enable a user to "press keys" that appear on the display 1106. In various embodiments, the communication interface(s) 1118 includes Wi-Fi, Bluetooth, and/or wired connections.

In some embodiments, the memory 1124 includes high-speed random-access memory, such as DRAM, SRAM, DDR RAM, and/or other random-access solid state memory devices. In some embodiments, the memory 1124 includes non-volatile memory, such as one or more magnetic disk storage devices, optical disk storage devices, flash memory devices, or other non-volatile solid state storage devices. In some embodiments, the memory 1124 includes one or more storage devices remotely located from the processor(s) 1102. The memory 1124, or alternatively the non-volatile memory device(s) within the memory 1124, comprises a computer readable storage medium. Memory for headsets include, for example, Random-Access Memory (RAM), such as Low Power Double Data Rate RAM (LPDDR), used for running the operating system, applications, and/or handling real-time data processing. Memory 1124 may also include storage memory, such as flash memory, similar to smartphones (e.g., eMMC or UFS), for storing the operating system, applications, and/or user data. Video memory, often integrated with the GPU in mobile chipsets, can be used to handle graphics processing tasks. Cache memory, such as Static RAM (SRAM), can be used for high-speed memory used by the processors 1102 for quick data access.

Referring to FIG. 11B, in some embodiments, the memory 1124, or the computer readable storage medium of the memory 1124, stores the following programs, modules, and data structures, or a subset thereof:

- an operating system 1130, which includes procedures for handling various basic system services and for performing hardware dependent tasks;
- a communications module 1132, which is used for connecting the computing device to other computers and devices via the one or more communication network interfaces 1118 (wired or wireless) and/or via one or more communication networks, such as the Internet, other wide area networks, local area networks, metropolitan area networks, and so on;
- a user interface module 1134 (sometimes referred to as the UI module 1134) for managing user interaction with VR/AR environments 1136 (sometimes referred to as three-dimensional virtual environments, photorealistic environments) and/or having system controls. This can include home environment, allowing users to launch apps, adjust settings, and/or navigate menus using virtual pointers or hand gestures;
- a rendering module 1138 for handling the creation and/or display of 3D graphics in real-time. This can include a rendering pipeline, for example Unity's VR rendering pipeline, for optimizing frame rates and/or reducing latency for smooth VR/AR experiences;
- a simulation module 1140 for creating and/or managing the rules, physics, and/or behaviors within the virtual environment. This can, for example, include PhysX in VR games, simulating realistic object interactions and gravity effects. The simulation module 1140 may include one or more scenarios 1142;
- a tracking module 1144 for processing sensor data to determine the position and orientation of the headset and/or controllers. The tracking module can track eye movements 1146 and/or response times 1148. In some embodiments, the eye movements 1146 includes dynamic focus adjustments;
- an evaluation and/or measurement module 1150 for analyzing user interactions and/or system performance for optimization and/or adaptation and feedback to determine and/or measure, for example, night vision and glare sensitivity 1152, pupil reaction to light changes 1154, and/or visual changes under varying light conditions 1156;
- an input module 1158 for interpreting and/or processing user input from various sources (e.g., controllers, hand tracking, voice commands). This module can include hand tracking software, translating hand and finger movements into VR interactions; and/or
- a calibration module 1160 for alignment of virtual and physical elements, often including initial setup procedures, for calibrating the device and/or experimental setups based on user data, which can include setup, and/or guiding users through the process of defining their viewing and/or test area and/or calibrating controllers.

The UI module 1134 may generate interactive visual elements that allow users to navigate and interact with the highly realistic 3D virtual world. This includes creating menus and buttons that appear to exist within a 3D space, implementing gesture-based controls that feel natural in the virtual world, designing visual feedback that matches the aesthetic of the environment, and/or integrating information displays seamlessly with the surroundings. The UI module 1134 may utilize various implementation methods, such as game engines (e.g., Unity, Unreal Engine) for UI implementation and integration, and/or 3D modeling software for creating UI assets. The processing may include processing on host computers for tethered VR headsets, may include on-device processing for standalone VR/AR headsets, and/ or cloud processing for computationally intensive tasks.

In various embodiments, the UI module 1134 enhances user immersion and presence by, for example, creating UI elements that look and feel like they belong in the photo-realistic environment, implementing holographic displays or interactive physical objects, and/or supporting interaction through VR controllers or hand tracking. In some embodiments, the UI module 1134 adapts the UI to different types of virtual environments, ensuring consistency and usability across various scenarios. In some embodiments, the UI module 1134 also handles user input (e.g., in collaboration with an input module, described below) through multiple modalities, including hand tracking, eye tracking, and controller input, to facilitate seamless interaction with the generated UI.

In some embodiments, the rendering module 1138 integrates the VR user interface elements with the photorealistic environment, ensuring proper depth, occlusion, and lighting interactions. In some embodiments, the rendering module 1138 implements stereo rendering techniques to create a sense of depth and dimensionality for the UI elements when displayed on the HMD. In some embodiments, the rendering module 1138 applies distortion correction and lens-specific optimizations to ensure the UI is properly displayed on the HMD's optics.

In some embodiments, the rendering module 1138 utilizes techniques like foveated rendering to optimize UI rendering performance, particularly for resource-intensive photorealistic environments. In some embodiments, the rendering module 1138 handles dynamic UI updates and animations in real-time, maintaining consistent frame rates crucial for comfortable VR experiences. In some embodiments, the rendering module 1138 implements anti-aliasing and other image quality enhancements specific to HMD displays to ensure crisp, readable UI elements.

In various embodiments, the one or more scenarios and/or test sequences 1142 can include real-world scenarios, dynamic real-world visual experiences, test sequences with progressively finer details, real-world motion and target recognition visual tasks, and/or various visual scenarios (including, for example, scenarios with different lighting conditions). In some embodiments, the simulation module 1140 may be further configured to generate and manage dynamic lighting scenarios within the VR user interface, simulating various real-world lighting conditions and their changes over time. In some embodiments, the simulation module 1140 may be further configured to implement advanced lighting models that accurately simulate the behavior of light, including effects such as global illumination, reflections, and shadows. In some embodiments, the simulation module 1140 may be further configured to create time-of-day lighting simulations, allowing for the representation of changing natural light conditions from dawn to dusk.

In some embodiments, the simulation module 1140 may be further configured to simulate various artificial lighting scenarios, such as indoor lighting with multiple light sources, street lighting, or stage lighting. In some embodiments, the simulation module 1140 may be further configured to incorporate dynamic elements like moving light sources, flickering lights, or sudden changes in illumination to test visual adaptation. In some embodiments, the simulation module 1140 may be further configured to integrate with the rendering module 1138 to ensure accurate representation of these dynamic lighting scenarios on the HMD, maintaining visual fidelity and realism. In some embodiments, the simulation module 1140 may be further configured to allow real-time adjustment and control of lighting parameters, enabling the creation of customized dynamic lighting scenarios for specific testing or training purposes.

For eye testing purposes, some embodiments track eye movements and response times with high frequency and precision. In some embodiments, for eye movements, and specifically for saccades, rapid movements of the eye between fixation points may be tracked at rates of at least 100-500 Hz. This high frequency helps capture the quick and brief nature of these movements accurately. For fixations, periods where the eyes are relatively stationary and focused on a single point are tracked at slightly lower rates, but typically in the range of 50-100 Hz, to ensure precise measurement of duration and stability. For smooth pursuit (e.g., movements where the eyes smoothly follow a moving object), eye movements may be also tracked at high rates (100-200 Hz) to accurately capture the speed and trajectory of the eye movements.

In some embodiments, for response times, specifically for reaction time (e.g., the time it takes for a person to respond to a visual stimulus, such as pressing a button when a light appears), eye movements may be tracked with millisecond accuracy. This typically means using sampling rates of 1000 Hz or higher to ensure precise measurement. For decision time, which may include, for example, the duration between recognizing a visual stimulus and making a decision based on, are tracked using high-frequency tracking, typically around 500-1000 Hz, to accurately capture the cognitive processing speed. High-frequency tracking ensures that no significant movement or response detail is missed, providing a more accurate and reliable assessment of visual function. Real-world visual tasks involve rapid and complex eye movements, and high-frequency tracking allows for a more detailed analysis of how well the eyes can handle such tasks. Subtle abnormalities in eye movements or delays in response times can be early indicators of visual or neurological problems. High-frequency tracking helps in detecting these issues at an early stage.

In some embodiments, for eye testing, continuous tracking of eye movements and response times is performed at high frequencies (e.g., ranging from 50 Hz to 1000 Hz) to ensure precise and comprehensive data collection. While both eye testing and VR games benefit from eye-tracking technology, the former requires much higher precision, frequency, and reliability for clinical and diagnostic purposes. In contrast, VR games prioritize user experience and real-time interaction, allowing for lower precision and frequency in tracking (e.g., 30-120 Hz). In some embodiments, the tracking module 1144 may be further configured to continuously track eye movements and response times in response to visual stimuli presented in the one or more dynamic lighting scenarios. In some embodiments, this tracking is performed using the camera at high frequencies (e.g., 100-500 Hz for saccades, 50-100 Hz for fixations) to capture rapid eye movements in changing light conditions.

In some embodiments, the tracking module 1144 may be further configured to continuously monitor and record pupil data, including pupil dilation and constriction, in response to visual stimuli presented in the one or more dynamic lighting scenarios. This pupil tracking is performed at high frequencies (e.g., 120-250 Hz) to capture subtle and rapid changes in pupil size as lighting conditions change. In some embodiments, the tracking module 1144 may be further configured to specifically track eye movements, including saccades, fixations, and smooth pursuit, in response to visual stimuli presented in the one or more dynamic lighting scenarios.

This tracking captures how the eyes adapt and respond to changing light levels, moving shadows, or shifting light sources within the virtual environment.

In some embodiments, the tracking module 1144 may be further configured to synchronize the eye tracking data with the simulated lighting conditions, allowing for precise analysis of how different lighting scenarios affect eye movements, pupil reactions, and response times. In some embodiments, the tracking module 1144 may be further configured to process and analyze the collected high-frequency eye movement, pupil, and response time data in real-time, providing immediate feedback on visual performance under varying lighting conditions. In some embodiments, the tracking module 1144 may be further configured to integrate with the simulation module 1140 to ensure that eye tracking is precisely coordinated with the dynamic changes in lighting conditions, allowing for accurate assessment of visual adaptation to light changes. These features may enable the system to capture detailed, time-synced data on eye movements, pupil reactions, and/or response times, specifically in relation to changing lighting conditions in the virtual environment, supporting comprehensive analysis of visual function and performance under various lighting scenarios.

In some embodiments, the evaluation and/or measurement module 1150 may be further configured to evaluate user response based on the eye movements and response times specifically for testing night vision and glare sensitivity. This may include, for example, analyzing saccadic eye movements and fixation patterns in low-light conditions to assess night vision capabilities, measuring response times to sudden bright stimuli in dark environments to evaluate glare sensitivity and recovery, and/or quantifying changes in visual acuity and contrast sensitivity under various lighting conditions, from very dim to very bright.

In some embodiments, the evaluation and/or measurement module 1150 may be further configured to measure pupil reaction to light changes based on the pupil data collected by the tracking module 1144. This may include, for example, calculating the speed and amplitude of pupil constriction and dilation in response to varying light intensities, analyzing the latency period between light change and pupil response, assessing the sustainability of pupil size under prolonged exposure to different light conditions, and/or comparing pupil reactions across different age groups or pre-existing visual conditions.

In some embodiments, the evaluation and/or measurement module 1150 may be further configured to evaluate the detection of subtle visual changes based on the eye movements. This may include, for example, analyzing micro-saccades and small fixational eye movements in response to minor changes in visual stimuli, measuring the time taken for the eyes to react to subtle changes in color, contrast, or movement within the visual field, assessing the accuracy of gaze redirection towards areas of subtle change in complex visual scenes, and/or quantifying the minimum detectable change in various visual parameters (e.g., brightness, color, shape) based on eye movement responses.

In some embodiments, the evaluation and/or measurement module 1150 may be further configured to integrate these evaluations with the simulation module 1140 to ensure precise correlation between the visual stimuli presented and the measured eye responses. In some embodiments, the evaluation and/or measurement module 1150 may be further configured to implement advanced signal processing and/or machine learning algorithms to extract meaningful metrics from the high-frequency eye tracking and pupil data, specifically tailored to assess night vision, glare sensitivity, and/or subtle change detection.

In some embodiments, the evaluation and/or measurement module 1150 may be further configured to generate detailed reports and visualizations of the evaluation results, providing quantitative measures of night vision capability, glare sensitivity, pupil reactivity, and subtle change detection thresholds.

Each of the above identified executable modules, applications, or sets of procedures may be stored in one or more of the previously mentioned memory devices, and corresponds to a set of instructions for performing a function described above. The above identified modules or programs (i.e., sets of instructions) need not be implemented as separate software programs, procedures, or modules, and thus various subsets of these modules may be combined or otherwise rearranged in various embodiments. In some embodiments, the memory 1124 stores a subset of the modules and data structures identified above. Furthermore, in some embodiments, the memory 1124 stores additional modules or data structures not described above. Example details and/or operations of the modules, data structures, applications and/or procedures, are further described below, according to some embodiments.

Although FIG. 11A shows a computing device, FIG. 11A is intended more as a functional description of the various features that may be present rather than as a structural schematic of the embodiments described herein. In practice, and as recognized by those of ordinary skill in the art, items shown separately could be combined and some items could be separated.

VR-Based Vision Test for Night Vision ad Glare Sensitivity

According to some embodiments, the vision test system 1100 described above is configured to implement a virtual vision test for evaluating night vision and glare sensitivity. FIGS. 12A-12N show a flow diagram of an example process 1200 for implementing a virtual eye test for evaluating night vision and glare sensitivity, according to some embodiments. The computer device 140 (e.g., the computing device described above in reference to FIGS. 11A and 11B) generates (e.g., in step 1200) (e.g., using the UI module 1134) a virtual reality (VR) user interface (UI) corresponding to a photorealistic virtual environment (e.g., an environment 1136). In some embodiments, game engines (e.g., platforms like Unity or Unreal Engine) are used to implement the UI and integrate it with the virtual environment.

3D modeling software may be used for creating assets that may be part of the UI in the photorealistic environment. In some embodiments, this step is performed on a host computer, whereby the main processing unit (CPU) and graphics card (GPU) of the computer connected to a VR/AR headset handles much of the heavy lifting for generating and rendering the UI. This can be useful for tethered VR headsets that rely on a powerful PC for processing. In some embodiments, this step is performed on the headset itself. Stand-alone VR/AR headsets have onboard processors that can handle some or all of the UI generation and rendering. This on-device processing provides responsive, low-latency interactions. Cloud processing can also be used for some aspects of UI generation. For example, tasks requiring heavy computation might be offloaded to cloud servers and streamed to the headset. A combination of the above, with some elements pre-baked during development, some processed on a host PC, and some handled by the headset itself, can be used in some embodiments.

In some embodiments, the step of generating a VR UI corresponding to a photorealistic environment includes creating interactive visual elements that allow users to navigate and interact with a highly realistic 3D virtual world. Photorealistic virtual environment refers to a 3D digital space that looks and behaves as close to reality as possible. Advanced graphics, lighting, textures, and/or physics simulations can be used to create a highly detailed and lifelike virtual world. VR user interface is the set of visual elements, controls, and/or interaction methods that allow users to navigate, manipulate, and/or engage with the virtual environment. In VR, these interfaces are designed to be intuitive and immersive, often blending seamlessly with the virtual world.

Generating the interface may include generating UI elements that are both functional and visually consistent with the photorealistic environment. In various embodiments, this includes menus and buttons that appear to exist within the 3D space, gesture-based controls that feel natural in the virtual world, visual feedback that matches the aesthetic of the environment, and/or information displays that integrate with the surroundings. The computer device 140 creates an interface that enhances the user's sense of presence and immersion in the virtual world. This often means making UI elements that look and feel like they belong in the photorealistic environment, such as holographic displays or physical objects that the user can interact with using VR controllers or hand tracking.

Eye testing using photorealistic environments offers several advantages compared to traditional methods. Photorealistic environments provide a more accurate and comprehensive assessment of visual function. For example, photorealistic environments provide realistic simulation, mimic real-world conditions much more accurately than traditional eye charts or simple visual tests. This allows for a more accurate assessment of how well a person can see in everyday situations. These environments can change dynamically to simulate different lighting conditions, distances, and angles, providing a more comprehensive test of visual capabilities, including peripheral vision and depth perception. Patients, especially children or those with attention difficulties, may find photorealistic environments more engaging than standard tests, leading to more reliable results as they are more likely to fully participate in the testing process. Traditional eye tests often focus on static images and high-contrast letters. Photorealistic environments, on the other hand, can be used to present complex, real-world visual tasks that can better assess functions like motion detection, contrast sensitivity, and/or color perception.

Furthermore, the photorealistic environment can be customized to the specific needs or conditions of the patient, such as simulating the individual's workplace or home setting, providing a personalized and relevant assessment of their vision. More complex and varied testing scenarios, which photorealistic environments can help simulate, can help in the early detection of visual problems that might not be apparent in traditional tests. This includes issues related to glare, night vision, and visual processing speeds.

Advanced eye-tracking technology, specific examples of which are described herein, can be used in photorealistic environments to provide objective data on eye movements, fixation points, and response times, offering a more detailed analysis of visual function. For patients undergoing vision therapy or rehabilitation, photorealistic environments can provide a controlled yet realistic setting for practicing visual skills, making the training more effective and directly applicable to real-world tasks. Overall, eye testing using photorealistic environments described herein, represents a significant advancement in optometry and vision science, offering a richer, more detailed, and accurate assessment of visual health.

The computer device 140 renders (e.g., in step 1204) (e.g., using the rendering module 1138) the VR user interface on the HMD 1102. In some embodiments, photorealistic environments are displayed by leveraging various techniques and technologies described herein, according to some embodiments. Some embodiments use photogrammetry to create highly detailed 3D models from a set of photographs. By capturing real-world objects or environments from multiple angles, photogrammetry helps reconstruct their geometry and computer textures with a high degree of realism. In some embodiments, these models are then imported into the VR environment (sometimes referred to as the photorealistic environment or three-dimensional virtual environment). Some embodiments provide 360-degree photography and videography. In some embodiments, VR devices display panoramic 360-degree photos and videos, which provide an immersive and photorealistic representation of real-world environments. In some embodiments, these are captured using specialized camera rigs or stitched together from multiple camera feeds.

Some embodiments use real-time ray tracing. Modern graphics hardware and rendering techniques like real-time ray tracing help simulate the behavior of light in a physically accurate manner. By accurately modeling the interaction of light with materials, surfaces, and objects, ray tracing produces highly photorealistic images and environments in real-time.

Some embodiments provide high-resolution textures and models. VR devices leverage high-resolution textures and detailed 3D models to create environments that closely resemble reality. In some embodiments, the environments are created using techniques like photogrammetry, 3D scanning, or manually by artists and designers. Some embodiments use physically based rendering (PBR). PBR includes simulating the behavior of materials and their interactions with light based on real-world physics principles. By accurately modeling materials and their properties, such as roughness, metallic properties, and reflectance, PBR produces highly realistic visuals in VR environments.

Some embodiments use image-based rendering, which includes using real-world photographs or video footage as the basis for rendering virtual environments. In some embodiments, by projecting and blending these images onto 3D geometry, a highly photorealistic environment is created. In some embodiments, VR devices capture real-world lighting information using techniques like light probes or environmental capture. This data can then be used to accurately simulate and recreate realistic lighting conditions within the virtual environment. By combining the techniques described herein and leveraging the latest advancements in graphics hardware and rendering algorithms, VR devices can provide highly immersive and photorealistic virtual experiences that closely resemble real-world environments.

Photorealistic environments used for eye testing can differ significantly from those used in VR games in several aspects, including design, functionality, and application. Photorealistic environments for eye testing are designed for precision, control, and repeatability to assess visual functions accurately, while those for VR games focus on creating immersive, interactive, and enjoyable experiences for entertainment. In contrast to VR games, eye testing requires clinical precision. Accordingly, some embodiments provide highly controlled and repeatable conditions for accurate diagnosis and assessment of visual functions.

In some embodiments, specific scenarios are tailored to simulate real-world conditions that are relevant for visual testing, such as different lighting conditions, contrast levels, and visual tasks like reading or recognizing objects. Environments may be kept consistent across tests to ensure reliable results. This includes controlled variations in visual stimuli to test specific aspects of vision. Eye testing also requires precision tracking. Accordingly, some embodiments utilize high-precision eye-tracking to measure fine details of eye movements, fixations, and/or response times. Some embodiments collect accurate data for clinical analysis, including metrics, such as saccadic latency, fixation stability, and smooth pursuit accuracy. Some embodiments can include standardized visual tests, such as visual acuity tests, contrast sensitivity tests, and visual field tests.

Referring next to FIG. 12B, in some embodiments, the photorealistic virtual environment includes (e.g., in step 1214) a high-fidelity virtual environment that can dynamically adjust light levels, colors, and/or sources. In some embodiments, the high-fidelity virtual environment includes (e.g., in step 1216) dynamic light sources that incorporate movable light sources that can change intensity and position. In some embodiments, the movable light sources include (e.g., in step 1218) one or more light sources selected from the group consisting of: headlights, streetlights and reflections.

For example, a photorealistic environment for eye testing that includes a simulated driving environment can include a controlled simulation of driving conditions at night or in fog, designed to assess visual acuity, peripheral vision, and reaction times. The environment would include standardized visual stimuli, such as road signs, other vehicles, and pedestrians, which appear in predetermined patterns and intervals. For repeatability, each test is consistent, with the same conditions and stimuli presented in the same manner each time. This ensures that results can be reliably compared across different sessions or subjects. As another example, a photorealistic environment for eye testing that includes reading and office tasks can include a photorealistic simulation of an office environment with various reading tasks. This could include reading text on a computer screen, paper documents, and recognizing icons or objects on a cluttered desk. For repeatability, text size, font, contrast, and lighting conditions are kept constant across tests. This allows precise measurement of reading speed, accuracy, and visual fatigue under standardized conditions.

As yet another example, a supermarket simulation can include a virtual supermarket where patients are asked to locate and identify products on shelves. The environment would include standardized lighting, product placement, and visual clutter. For repeatability, the position and appearance of products remain the same in each test, ensuring that any changes in performance are due to the patient's vision and not variations in the environment. Eye testing environments prioritize controlled and repeatable conditions to ensure accurate measurement of visual functions instead of, or in addition to, focusing on creating immersive and interactive experiences that engage and entertain players. Eye testing environments are standardized to eliminate variables that could affect the results. A goal of eye testing environments, such as the ones described herein, is to collect precise data for clinical analysis, more than merely providing enjoyable user experience.

Referring next to FIG. 12C, in some embodiments, the photorealistic virtual environment includes (e.g., in step 1220) one or more configurable parameters to alter environment settings, while simulating the one or more dynamic lighting scenarios. In some embodiments, the environment settings include (e.g., in step 1222) one or more settings selected from the group consisting of: weather conditions, time of day, and urban or rural settings. In some embodiments, the environment settings are (e.g., in step 1224) alterable via user input. In some embodiments, the environment settings are (e.g., in step 1226) alterable automatically depending on a test parameter for testing night vision and glare sensitivity.

In the context of testing night vision and glare sensitivity within a VR-based vision test, the system may make several automatic changes to the environment to test different aspects of night vision and glare sensitivity. Example changes to the environment may include lighting conditions.

The system, for example, may simulate varying levels of ambient light, such as transitioning from dusk to full night, or from a dimly lit room to a bright streetlight-lit environment. This would test the user's ability to see under different levels of darkness. For glare simulation, the system may introduce dynamic light sources, such as oncoming headlights, streetlights, or reflective surfaces, to create glare. This may include sudden, intense flashes of light designed to test the user's glare recovery time and sensitivity.

For weather conditions, simulated weather conditions like fog, rain, or snow may be introduced to create visual obstructions and test the user's ability to perceive objects and light sources under such conditions. For dynamic motion, the environment may include moving elements, such as passing cars or pedestrians, under various lighting conditions, to test the user's ability to track and respond to moving objects in low light or glare-heavy scenarios.

Some embodiments may automatically cycle through settings. For example, for scenario-cased transitions, the system may be programmed to automatically transition between different scenarios. For example, the test may start in a well-lit environment, gradually dim to simulate nightfall, and then introduce random bright light flashes to simulate headlights or streetlights. For randomized environmental changes, to prevent the user from anticipating changes, the system may randomize the sequence and timing of environmental changes.

For example, the direction and intensity of light sources may change unpredictably during the test, and the weather conditions may shift suddenly from clear skies to fog. For adaptive testing, the system may adapt the test parameters in real-time based on the user's performance. If the system detects that the user struggles with glare sensitivity, the system may introduce more frequent or intense glare scenarios to further assess the user's limitations and responses.

Referring back to FIG. 12A, the computer device 140 simulates (e.g., in step 1206) (e.g., using the simulation module 1140) one or more dynamic lighting scenarios (e.g., the scenarios 1142) in the VR user interface. Referring to FIG. 12D, in some embodiments, the one or more dynamic lighting scenarios includes (e.g., in step 1228) randomized lighting scenarios that randomly change intensity from high intensity to low intensity and vice versa, without following real-world lighting scenarios. In some embodiments, the one or more dynamic lighting scenarios includes (e.g., in step 1230) using one or more light mapping techniques to simulate realistic light behavior, including scattering, shadowing, and reflections. In some embodiments, the one or more dynamic lighting scenarios includes (e.g., in step 1232) one or more nighttime scenes in urban streets, country roads, or indoor settings, simulated with varying degrees of ambient light. In some embodiments, the one or more dynamic lighting scenarios includes (e.g., in step 1234) one or more low-light environments selected from the group consisting of: dimly lit parking garages, moonlit landscapes and twilight settings.

Referring next to FIG. 12E, in some embodiments, the one or more dynamic lighting scenarios includes (e.g., in step 1236) one or more nighttime scenes comprising an urban street with variable lighting from cars, streetlights and shop windows. In some embodiments, the one or more dynamic lighting scenarios includes (e.g., in step 1238) one or more low-light level scenarios comprising a twilight park, dimly lit alley, or an interior of a room with dim lighting. In some embodiments, the one or more dynamic lighting scenarios includes (e.g., in step 1240) one or more glare levels for simulating driving towards oncoming traffic, navigating through a brightly lit street with reflective surfaces, or encountering a sudden flash of bright light.

Referring next to FIG. 12F, simulating the one or more dynamic lighting scenarios includes (e.g., in step 1242) simulating one or more scenarios that cause glare, the one or more scenarios selected from the group consisting of: oncoming headlights, street lights, neon signs, and reflective surfaces that cause glare. In some embodiments, simulating the one or more dynamic lighting scenarios includes (e.g., in step 1244) varying direction and intensity of light from one or more light sources hitting an eye. In some embodiments, the light causes a clouding effect leading to a glare.

For example, parameters at high level may include direction and intensity. When light is hitting eye, specifically cornea, scars or cataract may cause clouding effect leading to glare. Semi-circle may be hitting both eyes, along x and y axis, rotations, half of a 3D sphere from all different points. This may be broken into x and y axes. Not every single dot needs to be covered. One eye may be able to see, other occluded. A person may be focusing on optotype in one eye. The system may perform rotation and/or randomization, and/or change position and/or intensity. Size of optotype may change from small to big, and/or intensity and direction of light may be changed in 3D space.

In some embodiments, simulating the one or more dynamic lighting scenarios includes (e.g., in step 1246) simulating one or more scenarios for assessing the ability to distinguish between different shades of gray comprising changing optotype direction, whereby after solid black light, solid black is changed to a level of gray having a different gray level closer to white, including smoothing to lessen pixelation. Changing the direction of the optotype within the VR environment refers to altering the orientation and positioning of the visual stimuli (e.g., letters, symbols, or shapes used in visual acuity tests) to assess a user's ability to recognize and respond to these stimuli under varying conditions. The optotype may be rotated along the X, Y, and Z axes to present it at different angles relative to the user's line of sight.

For example, a letter "E" may be rotated 90 degrees to appear sideways, or 180 degrees to appear upside down. This tests the user's ability to recognize and correctly identify the optotype regardless of its orientation. The optotype may be moved to different locations within the user's field of view. For instance, it could be positioned higher, lower, to the left, or to the right, to assess peripheral vision or the ability to track moving objects. This can also involve the optotype moving dynamically within the environment, requiring the user to follow it with their gaze. Changing the optotype's direction and position helps create a more comprehensive visual assessment, testing not just static visual acuity but also dynamic vision, peripheral vision, and the ability to adapt to varying visual challenges.

Referring next to FIG. 12G, simulating the one or more dynamic lighting scenarios includes (e.g., in step 1248) exposing an eye to the bright light to bleach the eye, by shining the bright light. In some embodiments, simulating the one or more dynamic lighting scenarios includes (e.g., in step 1250) starting with one or more simpler tasks for identifying stationary objects, progressing to more complex tasks including reading moving signs or navigating through a virtual maze, wherein each task lasts between 30 seconds to 2 minutes, with controlled lighting transitions.

In some embodiments, simulating the one or more dynamic lighting scenarios includes (e.g., in step 1252-0) controlling one or more lighting conditions to change predictably and repeatably for each user to maintain consistency in testing across users. In some embodiments, simulating the one or more dynamic lighting scenarios includes (e.g., in step 1252-2) using a library of lighting conditions that categorizes simulations by ambient light levels, dynamic glare sources, and specific environments. In some embodiments, simulating the one or more dynamic lighting scenarios includes (e.g., in step 1252-4) using a library of lighting conditions that allows selection of specific scenarios or includes a preset sequence designed to test various aspects of night vision and glare sensitivity.

Referring next to FIG. 12H, in some embodiments, the computer device 140 further includes, prior to simulating (e.g., in step 1254) the one or more dynamic lighting scenarios in the VR user interface: providing (e.g., in step 1256) a visual stimuli in the VR user interface to measure a user's susceptibility level to motion sickness; and in accordance with a determination that the user's susceptibility to motion sickness is above a predetermined threshold, reducing (e.g., in step 1258) a refresh rate of the VR user interface. Motion sickness, often experienced in VR environments, is a condition characterized by symptoms, such as nausea, dizziness, sweating, and headaches, which result from a mismatch between visual motion cues and the body's sense of balance and movement. In VR, motion sickness may occurs when the visual experience in the headset does not match the physical motion the user feels, leading to sensory conflict.

Examples for measuring susceptibility to motion sickness are described herein, according to some embodiments. Simulator Sickness Questionnaire (SSQ): Before starting the VR test, users may be asked to complete a questionnaire that assesses their susceptibility to motion sickness. The SSQ measures symptoms across different categories (nausea, oculomotor discomfort, disorientation) and assigns a score that helps determine how likely the user is to experience motion sickness in the VR environment. For physiological monitoring, the system may monitor physiological indicators, such as heart rate variability, skin conductance (sweating), and breathing rate, which often change in response to motion sickness. By tracking these indicators, the system may estimate the user's susceptibility to motion sickness.

Optionally, real-time user feedback may be used for measuring susceptibility to motion sickness. For example, during the VR session, the system may periodically prompt the user to report their current comfort level using a simple interface (e.g., pressing a button if they feel discomfort). The frequency and intensity of these reports may help assess their susceptibility to motion sickness.

In some instances, post-exposure symptom check mal be used for measuring susceptibility to motion sickness. After the VR session, users may be asked to rate the severity of any symptoms they experienced during the test. This information may be used to adjust future sessions to reduce the likelihood of motion sickness, such as by lowering the refresh rate or reducing the intensity of visual stimuli. These methods allow for a comprehensive assessment of a user's susceptibility to motion sickness, enabling the VR system to make real-time adjustments to minimize discomfort and maintain an effective testing environment.

Referring back to FIG. 12A, the computer device 140, while simulating (e.g., in step 1208) the one or more real-world scenarios, in real time, continuously tracks (e.g., in step 1210) (e.g., using the tracking module 1144), using the camera, eye movements (e.g., the eye movements 1146) and response times (e.g., the response times 1148) to visual stimuli presented in the one or more real-world scenarios.

Referring to FIG. 12I, in some embodiments, the computer device 140 continuously tracks eye movements and response times by tracking (e.g., in step 1260) eyeball position in relation to light sensitivity while using a light source to cause glare.

Referring back to FIG. 12A, the computer device 140, while simulating the one or more real-world scenarios, in real time, evaluates (e.g., in step 1212) (e.g., using the evaluation/measurement module 1150) user response based on the eye movements and the response times for testing night vision and glare sensitivity (e.g., the night vision and glare sensitivity 1152). Referring to FIG. 12J, in some embodiments, evaluating the user response based on the eye movements and the response times for testing night vision and glare sensitivity includes (e.g., in step 1262) tracking a response time to adapt to changes in lighting conditions as light is decreased. In some embodiments, evaluating the user response based on the eye movements and the response times for testing night vision and glare sensitivity includes (e.g., in step 1264) tracking a focus on a glare as light is decreased.

In some embodiments, evaluating the user response based on the eye movements and the response times for testing night vision and glare sensitivity includes (e.g., in step 1266) measuring visual acuity under varying light conditions using tests comprising dynamic Snellen charts. In some embodiments, evaluating the user response based on the eye movements and the response times for testing night vision and glare sensitivity includes (e.g., in step 1268) assessing an ability to distinguish between different shades of gray in low-light scenarios. In some embodiments, evaluating the user response based on the eye movements and the response times for testing night vision and glare sensitivity includes (e.g., in step 1270) measuring a time taken for a vision to return to baseline or normal vision after exposure to a bright light.

Referring next to FIG. 12K, evaluating the user response based on the eye movements and the response times for testing night vision and glare sensitivity includes (e.g., in step 1272) (i) one or more objective tests based on a response that indicates when a user starts seeing again, and (ii) one or more subjective tests comprising one or more vision acuity tests. In some embodiments, evaluating the user response based on the eye movements and the response times for testing night vision and glare sensitivity includes (e.g., in step 1274) collecting data on reaction times, accuracy of task completion, eye movement patterns, and recovery times from glare. In some embodiments, evaluating the user response based on the eye movements and the response times for testing night vision and glare sensitivity includes (e.g., in step 1276) using one or more metrics for identification accuracy, time to task completion, and time to visual recovery from glare, to assess night vision and glare sensitivity.

Referring next to FIG. 12L, in some embodiments, the computer device 140 further generates (e.g., in step 1278) one or more reports for summarizing a performance across different lighting conditions. In some embodiments, the computer device 140 further generates (e.g., in step 1280) one or more charts for showing visual clarity in low-light scenarios. In some embodiments, the computer device 140 further generates (e.g., in step 1282) one or more graphs indicating recovery times from different levels of glare exposure. In some embodiments, the computer device 140 further displays (e.g., in step 1284) results from various contrast levels tested. In some embodiments, the computer device 140 further displays (e.g., in step 1286) one or more suggestions for further evaluation or corrective measures if deficiencies are identified.

Based on the results of the VR-based vision tests, if deficiencies or issues are identified, the system may suggest several corrective measures, examples of which are described herein. Referral to a specialist: If the test results indicate a significant issue, such as severe night blindness or pronounced glare sensitivity, the system may recommend that the user consult an ophthalmologist or optometrist for further evaluation and treatment. Prescription of specialized lenses: The system may suggest the use of specialized lenses, such as anti-glare coatings or lenses designed to enhance contrast, to mitigate the effects of glare sensitivity or night vision deficiencies. Vision therapy exercises: For users with issues related to dynamic visual acuity or slow adaptation to changing light conditions, the system may recommend specific vision therapy exercises. These exercises, which could be performed within the VR environment or in a clinical setting, help improve the user's visual processing speed and accuracy.

Optional environmental modifications may include the following. If the user struggles with visual tasks in specific lighting conditions, the system may suggest modifications to their living or working environment.

For example, increasing ambient lighting, using soft, diffused light sources, or minimizing reflective surfaces in areas where the user spends significant time. Regular monitoring: For users with conditions that are likely to progress over time, such as retinitis pigmentosa or early-stage cataracts, the system may suggest regular monitoring and retesting at set intervals to track changes in vision and adjust corrective measures as needed. These recommendations help guide the user toward appropriate interventions that can improve their visual performance and comfort in daily life.

Referring next to FIG. 12M, in some embodiments, the resolution of the HMD includes (e.g., in step 1288) at least 1080 by 1200 pixels per eye. In some embodiments, precision level for the eye tracking includes (e.g., in step 1290) at least 0.5 degrees of visual angle. In some embodiments, infrared sensors for eye tracking sample (e.g., in step 1292) at the rate of at least 120 Hz to capture rapid eye movements accurately.

Referring next to FIG. 12N, in some embodiments, the computer device 140 further calibrates (e.g., in step 1294) (e.g., using the calibration module 1160) the one or more dynamic lighting scenarios using a control group including individuals with known conditions including retinitis pigmentosa (night blindness), normal vision, and those with a history of glare sensitivity. In some embodiments, the computer device 140 further calibrates (e.g., in step 1296) the one or more dynamic lighting scenarios using baseline metrics including average reaction times, standard recovery times from glare, and typical contrast sensitivity scores for each profile. In some embodiments, the computer device 140 further validates (e.g., in step 1298-0) results of testing by comparing results from the VR tests with conventional clinical tests to ensure accuracy.

In some embodiments, the computer device 140 further uses (e.g., in step 1298-2) statistical methods to validate consistency and reliability of the VR-based assessments. Statistical methods may be used ensuring the consistency and reliability of VR-based vision assessments. Example method includes test-retest reliability, which involves administering the same VR-based vision test to the same group of users on multiple occasions under identical conditions. Statistical measures, such as the intraclass correlation coefficient (ICC), are then calculated to assess the consistency of the test results across different sessions. A high ICC indicates that the test produces reliable and stable results over time.

Cronbach's Alpha is a statistical measure that may be used to assess the internal consistency of the test, particularly when the test involves multiple items or scenarios (e.g., different lighting conditions or types of glare). Cronbach's Alpha provides a measure of how closely related a set of items are as a group, indicating the reliability of the overall test. A higher alpha value suggests greater reliability. Bland-Altman analysis may be used to assess the agreement between the VR-based test results and those from conventional clinical tests. By plotting the differences between the two sets of results against their averages, the analysis helps determine if the VR-based test is a reliable alternative to traditional methods. Consistent agreement within predefined limits may be used to validate the VR-based test's reliability.

T-Tests and ANOVA are statistical tests that may be used to compare the results from different groups (e.g., individuals with normal vision versus those with known conditions like night blindness). T-tests can determine if there is a significant difference between the means of two groups, while ANOVA may be used when comparing three or more groups. Significant differences may be used to indicate the test's ability to distinguish between different visual conditions, validating its accuracy. Regression analysis may be used to model the relationship between the test results and various predictor variables (e.g., age, baseline visual acuity, lighting conditions). Regression analysis may be used for understanding how different factors affect the test outcomes, which can be used for validating the test's consistency and for making adjustments to improve accuracy. These statistical methods may help ensure that the VR-based assessments are both consistent across different uses and reliable when compared to established clinical standards.

VR-Based Application to Measure Pupil Reaction to Light Changes and Visual Imperfections in Virtual Environments According to some embodiments, the vision test system 1100 described above is configured to implement a virtual eye test for measuring pupil reaction to light changes and visual imperfections. FIGS. 13A-13G show a flow diagram of an example process 1300 for implementing a virtual vision test for measuring pupil reaction to light changes and visual imperfections, according to some embodiments.

The computer device 140 (e.g., the computing device described above in reference to FIGS. 11A and 11B) generates (e.g., in step 1302) (e.g., using the UI module 1134) a VR user interface corresponding to a photorealistic virtual environment.

The computer device 140 also renders (e.g., in step 1304) (e.g., using the rendering module 1138) the VR user interface on the HMD 312A. Example details of the virtual environment and rendering the VR user interface are described above in reference to FIG. 12B, according to some embodiments.

The computer device 140 also simulates (e.g., in step 1306) (e.g., using the simulation module 1140) one or more dynamic lighting scenarios (e.g., the scenarios 1142) in the VR user interface 1204. Referring next to FIG. 13B, in some embodiments, the one or more dynamic lighting scenarios includes (e.g., in step 1314) sudden flashes of light that last between 100 to 500 milliseconds. In some embodiments, time between the sudden flashes of light range (e.g., in step 1316) from 1 to 5 seconds. In some embodiments, the one or more dynamic lighting scenarios includes (e.g., in step 1318) flashes with varying light intensities, from dim (10 $cd/m^2$) to very bright (1000 $cd/m^2$). In some embodiments, the one or more dynamic lighting scenarios includes (e.g., in step 1320) scenarios with gradual changes in brightness with transitions over periods of 5 to 30 seconds. In some embodiments, the one or more dynamic lighting scenarios includes (e.g., in step 1322) one or more scenarios selected from the group consisting of: sunrise, sunset and moving from a dimly lit room to a brightly lit outdoor environment. In some embodiments, the one or more dynamic lighting scenarios includes (e.g., in step 1324) a series of 10 flashes, each 100 milliseconds long, with 2-second intervals. In some embodiments, the one or more dynamic lighting scenarios includes gradual increase in brightness over 30 seconds.

Referring next to FIG. 13C, in some embodiments, the one or more dynamic lighting scenarios includes (e.g., in step 1326) a plurality of flashes with a 3.5 second interval between a first flash and a second flash and a 4.5 second interval between the second flash and a third flash. In some embodiments, the one or more dynamic lighting scenarios includes (e.g., in step 1328) a plurality of flashes with at least a 3 second interval and lesser than a 10 second interval between two flashes. In some embodiments, simulating the one or more dynamic lighting scenarios includes (e.g., in step 1330) driving lighting scenarios using a lighting scenarios library that categorizes abrupt changes for sudden flashes having subcategories for low, medium and high intensities, and gradual changes to brightness having subcategories for slow, medium and fast transitions. In some embodiments, the sudden flashes include (e.g., in step 1332) 100 ms flashes at 100 $cd/m^2$ and 500 ms flashes at 500 $cd/m^2$. In some embodiments, the gradual brightness adjustment includes (e.g., in step 1334) 10-second transition from 100 $cd/m^2$ to 500 $cd/m^2$, and 30-second transition from 10 $cd/m^2$ to 1,000 $cd/m^2$.

Referring back to FIG. 13A, the computer device 140, while simulating (e.g., in step 1308) the one or more dynamic lighting scenarios, continuously tracks (e.g., in step 1310) (e.g., using the tracking module 1144) pupil data (e.g., the eye movements 1146) in response to visual stimuli presented in the one or more dynamic lighting scenarios. Referring next to FIG. 13D, in some embodiments, tracking the pupil data incudes using (e.g., in step 1336) infrared light to monitor pupil size and movements without visible light interference, and tracking and recording pupil responses. In some embodiments, tracking the pupil data incudes using (e.g., in step 1338) one or more pupilometers of the electronic device to measure pupil response to light changes accurately.

In some embodiments, tracking the pupil data incudes using (e.g., in step 1340) high-resolution infrared eye-tracking cameras capable of capturing detailed pupil size and movement that sample at least at 120 Hz. In some embodiments, tracking the pupil data incudes using (e.g., in step 1342) at least 0.1 mm precision for measuring pupil size. In some embodiments, tracking the pupil data is performed (e.g., in step 1344) at the rate of 5 milliseconds to ensure real-time tracking. In some embodiments, tracking the pupil data uses (e.g., in step 1346) high-resolution sensors for capturing detailed images of the pupil.

Figure 13E:
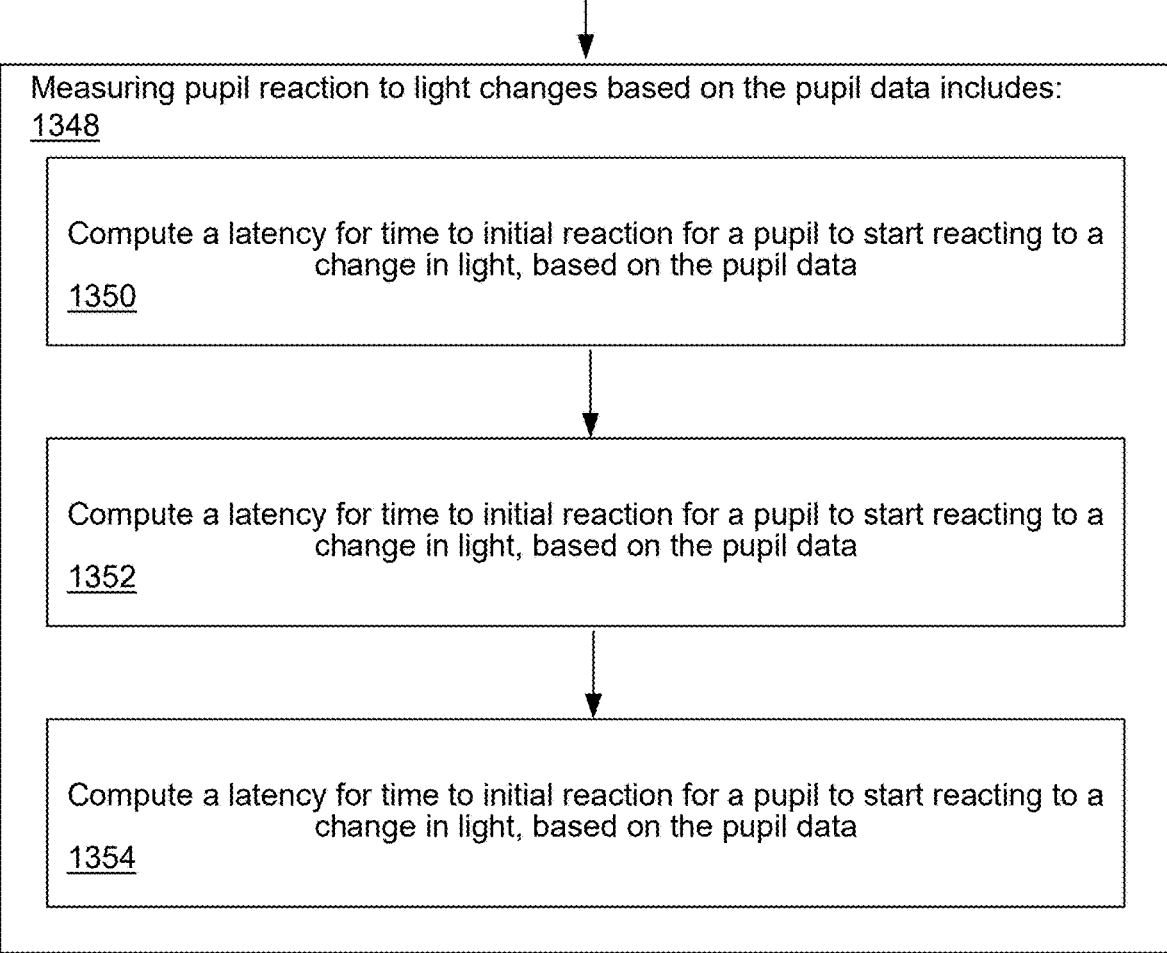

Referring next to FIG. 13E, measuring pupil reaction to light changes based on the pupil data includes (e.g., in step 1348): computing (e.g., in step 1350) a latency for time to initial reaction for a pupil to start reacting to a change in light, based on the pupil data; computing (e.g., in step 1352) an amplitude based on maximum pupil constriction and a baseline pupil size before the change in light, for the pupil data; and calculating (e.g., in step 1354) a speed of constriction and dilation of the pupil in response to the change in light, based on the pupil data.

Referring next to FIG. 13F, in some embodiments, the computer device 140 further maps (e.g., in step 1356) abnormalities including anisocoria, optic neuropathy, and visual pathway disorder, based on measuring the pupil reaction to light changes. In some embodiments, the computer device 140 further maps (e.g., in step 1358) abnormalities to anisocoria comprises comparing responses of both eyes to identify differences in pupil size, based on the pupil data. In some embodiments, the computer device 140 further maps (e.g., in step 1360) abnormalities to optic neuropathy comprises analyzing consistency and speed of pupil responses to thereby detect potential nerve damage.

In some embodiments, the computer device 140 further maps (e.g., in step 1362) abnormalities to visual pathway disorder comprises using one or more machine learning algorithms to compare responses to baseline data from individuals with known conditions. Some embodiments use supervised learning with neural Networks, which is a machine learning approach for mapping abnormalities to visual pathway disorders involves using supervised learning with neural networks. The algorithm may be trained on a labeled dataset where the input data (e.g., pupil responses to light changes) is paired with known outcomes (e.g., diagnosed visual pathway disorders). The neural network learns patterns and correlations in the data enable the algorithm to predict the likelihood of a disorder when presented with new, unlabeled data.

Some embodiments use random forest classifier, which involves using a Random Forest classifier, which is an ensemble learning method that operates by constructing multiple decision trees during training. The Random Forest may then output the mode of the classes (for classification) or the mean prediction (for regression) of the individual trees. This method may be used for handling complex, non-linear relationships between the input variables (e.g., latency, amplitude, and speed of pupil reaction) and the outcome (e.g., type of visual disorder). Support Vector Machines (SVMs) may be used to find the hyperplane that best separates different classes of visual pathway disorders based on the input features. The algorithm tries to maximize the margin between the different classes, making it effective for binary classification tasks, such as distinguishing between normal and abnormal pupil responses.

Machine learning may be used for handling complex data. The relationship between pupil reaction data and specific visual pathway disorders, for example, can be complex and non-linear. Machine learning algorithms are adept at identifying subtle patterns and interactions in large datasets that may not be apparent through traditional statistical methods. Machine learning help improve diagnostic accuracy. By training on a large dataset with known outcomes, machine learning models learn to accurately predict the presence of visual disorders based on new data. This can improve diagnostic accuracy, particularly in cases where the differences between normal and abnormal responses are subtle. Machine learning allows for the personalization of diagnostics. By continuously learning from new data, the algorithm can adapt and refine its predictions based on individual user profiles, leading to more tailored and accurate assessments. Machine learning models can process and analyze large volumes of data much faster than traditional methods, providing real-time insights and recommendations during the VR-based vision test. In this way, machine learning can be used for enhancing the precision, accuracy, and/or efficiency of VR-based vision assessments, making them more reliable and personalized.

Referring next to FIG. 13G, in some embodiments, the computer device 140 (e.g., the calibration module 1160) further calibrates (e.g., in step 1364) the one or more dynamic lighting scenarios based on a control group comprising individuals with normal vision, individuals with anisocoria, and individuals with optic neuropathy. In some embodiments, the computer device 140 further calibrates (e.g., in step 1366) the one or more dynamic lighting scenarios using baseline responses for individuals with no known visual impairments, baseline for individuals with unequal pupil sizes, and baseline for individuals with optic nerve damage. In some embodiments, the computer device 140 (e.g., the calibration module 1160) further calibrates (e.g., in step 1368) the one or more dynamic lighting scenarios using baseline pupillary responses comprising average latency of 150 ms, average constriction of 2.5 mm, and average constriction speed of 0.5 mm/s. In some embodiments, the computer device 140 further validates (e.g., in step 1370) the measured pupil reaction to light changes by comparing a test group's responses to a control group's baseline metrics. In some embodiments, the computer device 140 further validates (e.g., in step 1372) the measured pupil reaction to light changes using statistical methods including t-tests to validate the accuracy and consistency of measurement algorithms.

VR Technique for Evaluating Response Time in Detecting Subtle Visual Changes Under Varying Light Conditions According to some embodiments, the vision test system 1100 described above is configured to implement a virtual eye test for evaluating response time in detecting subtle visual changes under varying light conditions. FIGS. 14A-14G show a flow diagram of an example process 1400 for implementing a virtual eye test for evaluating response time in detecting subtle visual changes under varying light conditions.

The computer device 140 (e.g., the computing device described above in reference to FIGS. 11A and 11B) generates (e.g., in step 1402) (e.g., using the UI module 1134) a VR user interface corresponding to a photorealistic virtual environment (e.g., the environment 1136).

The computer device 140 also renders (e.g., in step 1404) (e.g., using the rendering module 1138) the VR user interface on the HMD 312A. Example details of the three-dimensional virtual environment and rendering the VR user interface are described above in reference to FIG. 12B, according to some embodiments.

The computer device 140 also simulates (e.g., in step 1406) (e.g., using the simulation module 1140) one or more dynamic lighting scenarios (e.g., the scenario 1142) in the VR user interface. Referring to FIG. 14B, in some embodiments, simulating the one or more dynamic lighting scenarios includes simulating (e.g., in step 1414) the one or more dynamic visual scenarios includes generating and controlling subtle changes in visual field, including slight alterations in color, shape or movement. In some embodiments, the one or more dynamic visual scenarios includes (e.g., in step 1416) one or more scenarios for identifying slight changes in color hue or brightness in a specific part of a visual field, including using color gradients that change slowly and subtly, requiring a user to respond when they detect the change. In some embodiments, the one or more dynamic visual scenarios includes (e.g., in step 1418) one or more scenarios for detecting minor alterations in the shape of objects including slight deformation of a geometric figure, including displaying objects that gradually morph in shape, prompting users to identify the change. In some embodiments, the one or more dynamic visual scenarios includes (e.g., in step 1420) one or more scenarios for identifying subtle movements within a stationary visual scene, including a slight shift in the position of an object, including implementing background scenes where certain elements move minimally, requiring users to pinpoint these movements.

Referring next to FIG. 14C, in some embodiments, the one or more dynamic visual scenarios include (e.g., in step 1422) lighting environments with (i) dim lighting that simulate low-light environments with brightness levels around 10 cd/m$^2$. In some embodiments, the one or more dynamic visual scenarios include (e.g., in step 1424) lighting environments with bright lighting that simulate environments with high brightness around 1000 cd/m$^2$. In some embodiments, the one or more dynamic visual scenarios include (e.g., in step 1426) lighting environments with fluctuating light levels including dynamic changes in lighting, transitioning between dim and bright environments over 5 to 30 seconds.

In some embodiments, the one or more dynamic lighting scenarios include (e.g., in step 1428) subtle visual changes including color changes for gradual shifts in hue or saturation, requiring quick detection, shape changes for minor alterations in geometric chapes or object outlines, and slight, almost imperceptible movements within a scene. In some embodiments, simulating the one or more dynamic lighting scenarios includes (e.g., in step 1430) using a library of lighting conditions that categorizes scenarios by (i) a type of visual change including color, shape and movement, and (ii) lighting environment including dim, bright and fluctuating. In some embodiments, the library of lighting conditions further categorizes (e.g., in step 1432) each scenario by a level of difficulty based on subtlety of changes and speed required for detecting subtle changes in color gradients for color detection, minor deformations of geometric figures for shape alterations, and slight shifts in object positions for movement detection.

Referring back to FIG. 14A, the computer device 140 also, while simulating the one or more dynamic lighting scenarios in real-time (e.g., in step 1408), continuously tracks (e.g., in step 1410) (e.g., using the tracking module 1144) eye movements (e.g., the eye movements 1146) in response to visual stimuli presented in the one or more dynamic lighting scenarios. Referring next to FIG. 14D, in some embodiments, tracking the eye movements includes (e.g., in step 1434) using eye-tracking sensors with accuracy of 0.5 degrees of visual angle or better, at a sampling rate of at least 120 Hz to accurately capture quick eye movements and response times. In some embodiments, tracking the eye movements includes (e.g., in step 1436) using infrared eye-tracking sensors to capture detailed eye movements, including fixations, saccades, and blinks. In some embodiments, tracking the eye movements includes (e.g., in step 1438) using at least 0.1 mm precision for measuring eye movements. In some embodiments, tracking the eye movements is performed (e.g., in step 1440) with a latency below 5 milliseconds to ensure real-time tracking. In some embodiments, tracking the eye movements includes (e.g., in step 1442) using high-resolution sensors for capturing detailed images of the pupil and eye movement data.

Referring back to FIG. 14A, the computer device 140 also evaluates (e.g., in step 1412) (e.g., using the evaluation/measurement module 1150) detection of subtle visual changes based on the eye movements. Referring next to FIG. 14E, in some embodiments, evaluating the response times includes mapping (e.g., in step 1444) the response times to specific visual stimuli presented in the photorealistic virtual environment, correlating eye movement data with the appearance of visual changes. In some embodiments, evaluating the response times includes mapping (e.g., in step 1446) the eye movements to visual perception and cognitive processing speed. In some embodiments, evaluating the response times includes measuring (e.g., in step 1448) latency including calculating time taken from the presentation of a visual change to the user's detection as indicated by an eye movement or a press of a button. In some embodiments, evaluating the eye movements includes collecting (e.g., in step 1450) baseline data from a control group with known visual and cognitive health status, and comparing response times and accuracy against the baseline data to identify deviations indicative of potential impairments.

Referring next to FIG. 14F, in some embodiments, the electronic device includes (e.g., in step 1452) a high-resolution headset offering at least 1080 times 1200 pixels per eye, at least 90 Hz refresh rate to ensure smooth visual presentation and reduce motion sickness, and a wide field of view (FOV) of at least 110 degrees to provide an immersive experience. In some embodiments, the computer device 140 further provides (e.g., in step 1454) insights into visual and cognitive processing abilities based on analysis of speed and accuracy of responses based on the eye movements. In some embodiments, the computer device 140 further provides (e.g., in step 1456) an analysis of performance under each lighting condition, including reaction times and detection accuracy. In some embodiments, the computer device 140 further provides (e.g., in step 1458) a diagnostic including highlighting areas of concern that suggest conditions including macular degeneration, glaucoma, or cognitive decline.

Referring next to FIG. 14G, in some embodiments, the computer device 140 further calibrates (e.g., in step 1460) (e.g., using the calibration module 1160) the one or more dynamic lighting scenarios using known visual and cognitive health profiles of a control group comprising individuals with normal vision, age-related macular degeneration, glaucoma, early cognitive decline, and other relevant conditions. In some embodiments, the computer device 140 further calibrates (e.g., in step 1462) the one or more dynamic lighting scenarios using baseline metrics including average reaction times, detection accuracy, and other relevant metrics. In some embodiments, the computer device 140 further uses (e.g., in step 1462) statistical methods including t-tests and ANOVA to validate consistency and reliability of the VR-based assessments by comparing test results against baseline metrics. In some embodiments, the computer device 140 further validates (e.g., in step 1464) results of testing by comparing results from the VR tests across different users and sessions.

Example Vision Test Process

Figure 15:
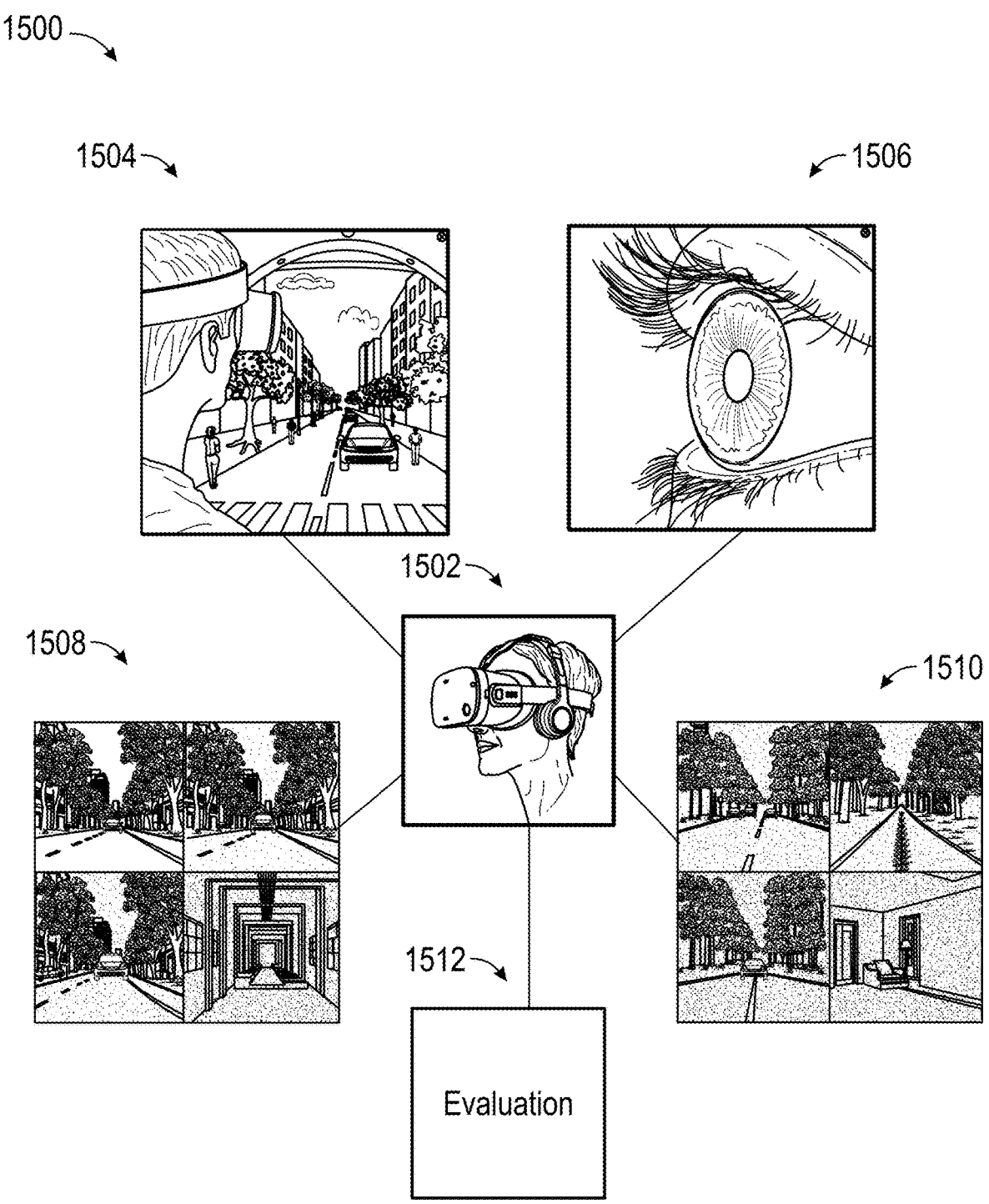
FIG. 15 is a schematic diagram showing an example vision test, in accordance with some embodiments.

FIG. 15 is a schematic diagram showing an example vision test 1500, in accordance with some embodiments. The illustration 1502 shows a person wearing a VR headset (HMD). The VR headset may include eye-tracking cameras. As shown in the illustration 1504, the user's view through the HMD may show a photorealistic virtual environment. The illustration 1506 shows a close-up of an eye that may be tracked by the eye-tracking cameras, which may track eye movements, such as saccades, fixations, and smooth pursuit. The illustrations 1508 and 1510 show example scenarios that may be displayed in the HMD for evaluation response. Based on responses, the system may perform various evaluations (e.g., in step 1512).

Example VR Night Vision and Glare Sensitivity Test

Figures 16A, 16B, 16C:
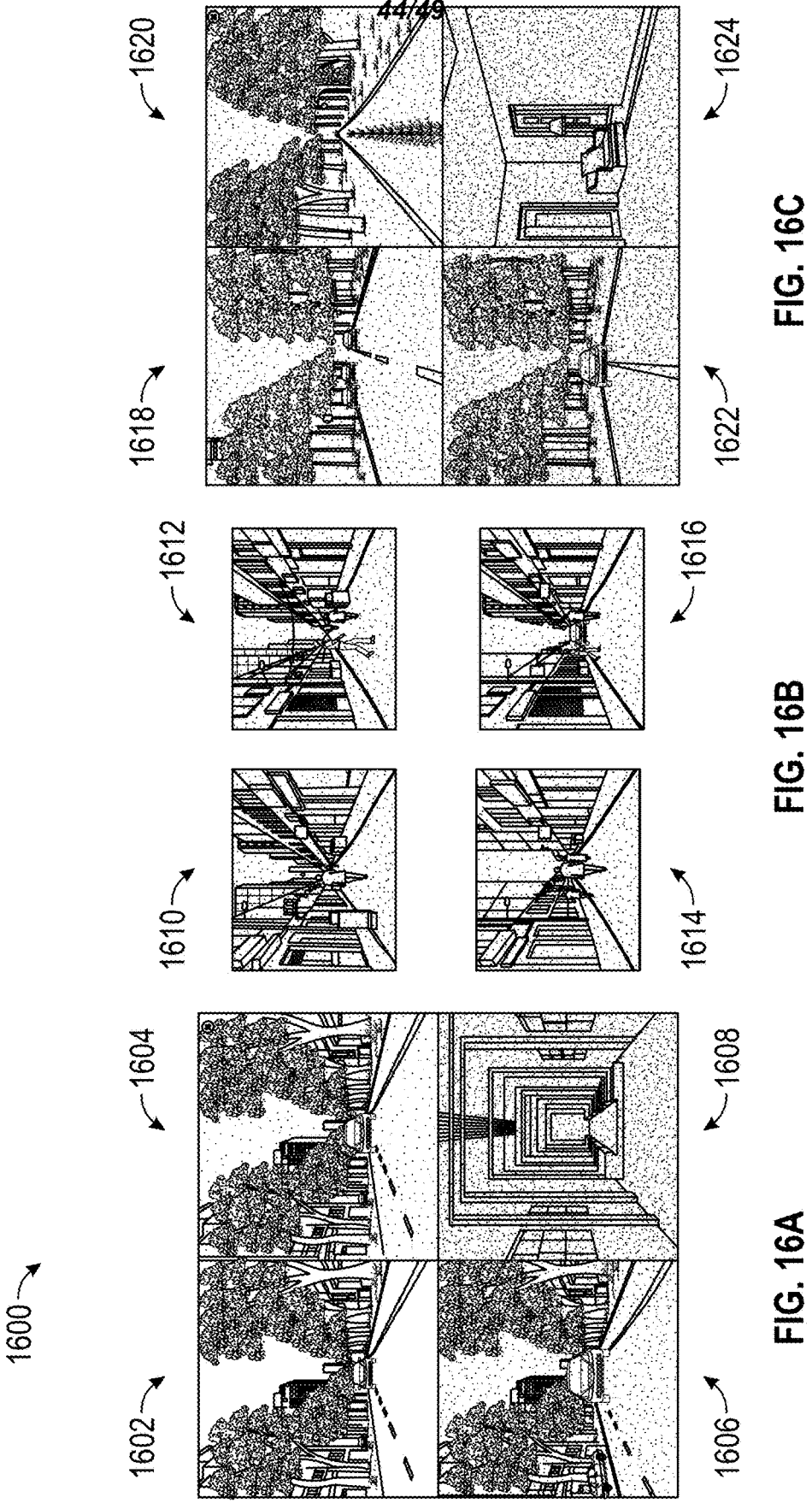
FIGS. 16A-16C are illustrations of example scenarios for VR night vision and glare sensitivity test, according to some embodiments.

FIGS. 16A-16C are illustrations of example scenarios 1600 for VR night vision and glare sensitivity test, according to some embodiments. FIG. 16C shows four example scenarios. Illustration 1618 shows a well-lit street scene, illustration 1620 shows a twilight park scene, illustration 1622 shows a nighttime driving scenario with oncoming headlights, and illustration 1624 shows a dimly lit interior room. Illustrations 1602, 1604, 1606, and 1608 (FIG. 16A), and illustrations 1610, 1612, 1614, and 1616 (FIG. 16B) show further example visual scenarios. Various scenarios may require identifying stationary objects in low light (e.g., in the scenario shown in 1610), reading moving signs in varying light conditions (e.g., in the scenarios shown in 1602 or 1604), navigating through a virtual maze in near-darkness (e.g., the scenario shown in 1608), reacting to a sudden glare sources (e.g., an oncoming car shown in 1622). Visual stimuli, such as objects to identify or navigate around, may incorporate glare sources. A user may respond with eye movements, a readout of response times to various visual stimuli, and/or biometric data feedback (e.g., pupil dilation, retinal response), which may be retrieved and/or recorded.

FIG. 16D is a block diagram of example components 1626 for VR night vision and glare sensitivity test, according to some embodiments. Some embodiments can include real-time manipulation of light levels and/or environmental settings 1626, which may include, for example, sliders for controlling ambient light, glare intensity, and/or weather conditions, and/or buttons to switch between urban and rural settings 1630.

Some embodiments generate and/or display performance graph(s) 1632, which may include, for example, an X-axis showing decreasing light levels and increasing glare, a Y-axis showing visual performance metrics (acuity, response time), and/or a line graph demonstrating changes in visual performance across conditions 1634. Some embodiments can include an AI interface 1638, which may include, for example, real-time analysis of user performance, and/or suggestions for adapting the test difficulty based on individual results 1638. Some embodiments generate and/or display a results summary 1640, which may include, for example, an overall night vision and glare sensitivity assessment, a breakdown of performance in different lighting conditions, graphs of recovery times from glare exposure, and/or recommendations for further evaluation or corrective measures 1642.

Example VR Pupil Reaction to Light Changes Test

Figure 17A:
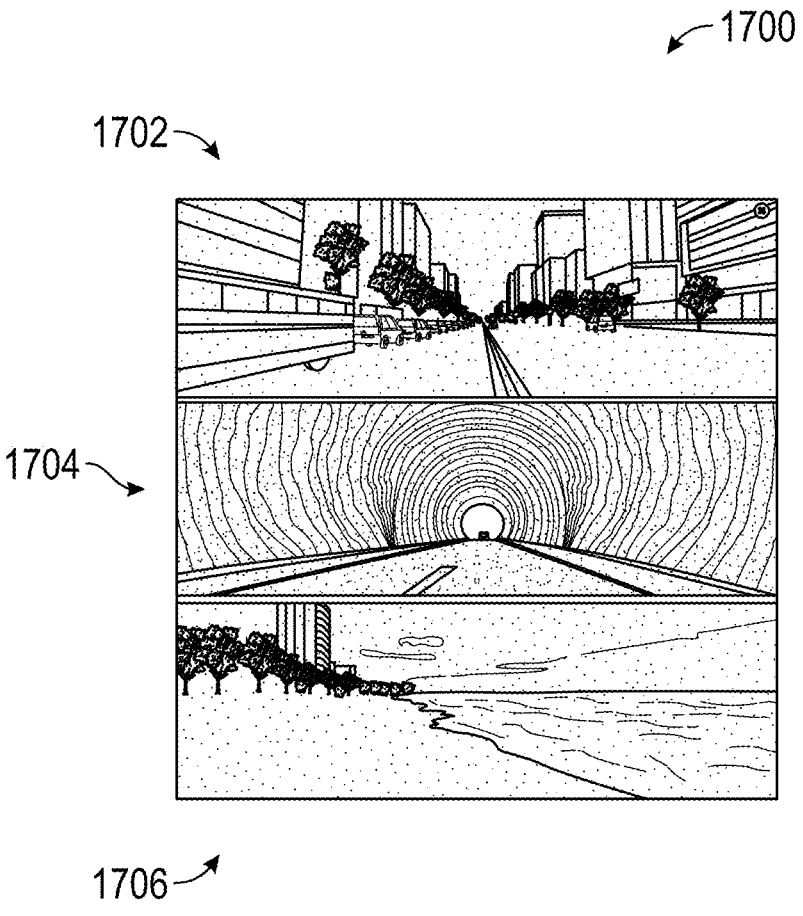
FIG. 17A are illustrations of example lighting scenarios for VR pupil reaction to light changes test, according to some embodiments.

FIG. 17A are illustrations of example lighting scenarios 1700 for VR pupil reaction to light changes test, according to some embodiments. A person may view the scenarios through the display of a VR headset (HMD) (e.g., a HMD that includes infrared eye-tracking cameras).

The scenarios may correspond to, for example, sudden bright flashes of different intensities and durations (e.g., the illustration 1702), gradual transitions from dim to bright environments (e.g., while exiting a tunnel as shown in illustration 1704), or simulated sunrise and sunset scenes (e.g., the illustration 1706). Pupil dilation and/or constriction may be tracked, and a real-time readout of pupil size measurements may be obtained. High-speed capture of pupillary response may be used.

FIG. 17B is a block diagram of example components 1708 for VR pupil reaction to light changes test, according to some embodiments. Some embodiments can include progression of a test 1720, which may include, for example, a baseline pupil size obtained in neutral lighting, response to sudden flash (e.g., 100 ms at 100 cd/m$^2$), adaptation during gradual brightness, and/or recovery after exposure to bright light.

Some embodiments generate and/or display a pupil response graph 1714, which may include, for example, an X-axis showing time, a Y-axis showing pupil size, and/or multiple lines depicting pupil reaction to different light stimuli 1716. Some embodiments can include lighting scenario controls 1718, which may include, for example, buttons for triggering different flash sequences, and/or sliders for adjusting the speed of gradual light changes 1720.

Some embodiments can include an abnormality mapping 1722, which may include, for example, a visual representation of pupillary response patterns, indicators for potential issues (e.g., anisocoria, optic neuropathy), and/or a comparison to baseline data from control groups 1724. Some embodiments can include results analysis 1726, which may include, for example, computed metrics (e.g., latency, amplitude, constriction/dilation speed), comparison to normative data, and/or flagged areas of concern or abnormal responses 1728.

Example VR Subtle Visual Changes Detection Test

Figures 18A, 18B, 18C:
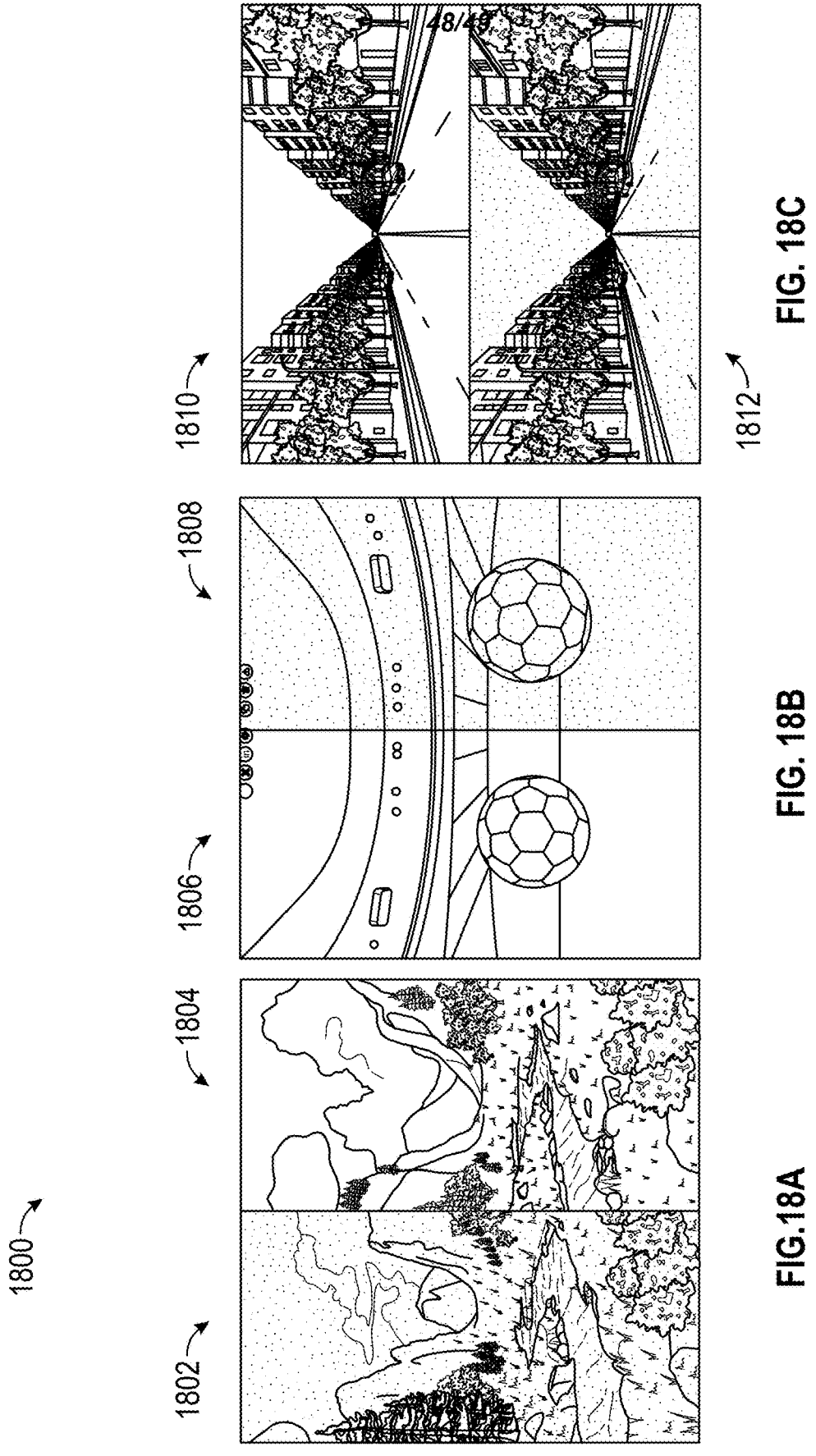
FIGS. 18A-18C are illustrations of example scenarios for VR subtle visual changes detection test, according to some embodiments.

FIGS. 18A-18C are illustrations of example scenarios 1800 for VR subtle visual changes detection test, according to some embodiments. The scenarios illustrate different types of subtle changes. Illustrations 1802 and 1804 (FIG. 18A) show color changes (e.g., gradual shifts in hue or saturation), illustrations 1806 and 1808 (FIG. 18B) show shape changes (e.g., minor alterations in geometric shapes), and illustrations 1810 and 1812 show movement changes (e.g., slight shifts in object positions). User responses to stimuli (e.g., eye movements) may be captured, and/or a readout of response times to various visual stimuli may be obtained. Some embodiments provide fixation and/or saccade patterns visualizations.

FIG. 18D shows a block diagram of example components 1814 for VR subtle visual changes detection test, according to some embodiments. Some embodiments can include a progression of test difficulty 1816, which may include, for example, easily noticeable changes, moderately subtle changes, and/or extremely subtle changes requiring keen perception 1818.

Some embodiments can include lighting condition controls 1820, which may include, for example, a slider for adjusting ambient light levels (e.g., 10 cd/m$^2$ to 1000 cd/m$^2$), and/or a toggle for activating fluctuating light conditions 1822. Some embodiments can include a response time graph 1824, which may include, for example, an X-axis showing progression of test (e.g., increasing subtlety), a Y-axis showing response time, and/or multiple lines representing different types of changes (e.g., color, shape, movement) 1826. Some embodiments can include an AI interface 1828, which may include, for example, real-time analysis of detection accuracy and speed, a comparison of performance to baseline data, and/or suggestions for adjusting test parameters 1830.

Some embodiments can include a performance summary 1832, which may include, for example, an overall assessment of subtle change detection ability, breakdown of performance in different lighting conditions, insights into visual and cognitive processing speeds, and/or potential areas of concern or suggested further testing 1834.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A method of implementing a virtual vision test for night vision and glare sensitivity, comprising: at an electronic device including a head-mounted display and a camera: generating a virtual reality (VR) user interface corresponding to a photorealistic virtual environment; rendering the VR user interface on the HMD; simulating one or more dynamic lighting scenarios in the VR user interface; and while simulating the one or more dynamic lighting scenarios, in real time: continuously tracking, using the camera, eye movements and response times in response to visual stimuli presented in the one or more dynamic lighting scenarios; and evaluating user response based on the eye movements and the response times for testing night vision and glare sensitivity.

Clause 2. The method of Clause 1, wherein the photorealistic virtual environment comprises a high-fidelity virtual environment that can dynamically adjust light levels, colors, and/or sources.

Clause 3. The method of Clause 2, wherein the high-fidelity virtual environment comprises dynamic light sources that incorporate movable light sources that can change intensity and position.

Clause 4. The method of Clause 3, wherein the movable light sources comprises one or more light sources selected from the group consisting of: headlights, streetlights and reflections.

Clause 5. The method of any of Clauses 1-4, wherein the photorealistic virtual environment includes one or more configurable parameters to alter environment settings, while simulating the one or more dynamic lighting scenarios.

Clause 6. The method of Clause 5, wherein the environment settings include one or more settings selected from the group consisting of: weather conditions, time of day, and urban or rural settings.

Clause 7. The method of Clause 5, wherein the environment settings are alterable via user input.

Clause 8. The method of Clause 5, wherein the environment settings are alterable automatically depending on a test parameter for testing night vision and glare sensitivity.

Clause 9. The method of any of Clauses 1-8, wherein the one or more dynamic lighting scenarios comprises randomized lighting scenarios that randomly change intensity from high intensity to low intensity and vice versa, without following real-world lighting scenarios.

Clause 10. The method of any of Clauses 1-9, wherein the one or more dynamic lighting scenarios comprises using one or more light mapping techniques to simulate realistic light behavior, including scattering, shadowing, and reflections.

Clause 11. The method of any of Clauses 1-10, wherein the one or more dynamic lighting scenarios comprises one or more nighttime scenes in urban streets, country roads, or indoor settings, simulated with varying degrees of ambient light.

Clause 12. The method of any of Clauses 1-11, wherein the one or more dynamic lighting scenarios comprises one or more low-light environments selected from the group consisting of: dimly lit parking garages, moonlit landscapes and twilight settings.

Clause 13. The method of any of Clauses 1-12, wherein the one or more dynamic lighting scenarios comprises one or more nighttime scenes comprising an urban street with variable lighting from cars, streetlights and shop windows.

Clause 14. The method of any of Clauses 1-13, wherein the one or more dynamic lighting scenarios comprises one or more low-light level scenarios comprising a twilight park, dimly lit alley, or an interior of a room with dim lighting.

Clause 15. The method of any of Clauses 1-14, wherein the one or more dynamic lighting scenarios comprises one or more glare levels for simulating driving towards oncoming traffic, navigating through a brightly lit street with reflective surfaces, or encountering a sudden flash of bright light.

Clause 16. The method of any of Clauses 1-15, wherein simulating the one or more dynamic lighting scenarios comprises simulating one or more scenarios that cause glare, the one or more scenarios selected from the group consisting of: oncoming headlights, street lights, neon signs, and reflective surfaces that cause glare.

Clause 17. The method of any of Clauses 1-16, wherein simulating the one or more dynamic lighting scenarios comprises varying direction and intensity of light from one or more light sources hitting an eye, wherein the light causes a clouding effect leading to a glare.

Clause 18. The method of any of Clauses 1-17, wherein simulating the one or more dynamic lighting scenarios comprises simulating one or more scenarios for assessing the ability to distinguish between different shades of gray comprising changing optotype direction, whereby after solid black light, solid black is changed to a level of gray having a different gray level closer to white, including smoothing to lessen pixelation.

Clause 19. The method of Clause 18, wherein simulating the one or more dynamic lighting scenarios comprises exposing an eye to the bright light to bleach the eye, by shining the bright light.

Clause 20. The method of any of Clauses 1-19, wherein simulating the one or more dynamic lighting scenarios comprises starting with one or more simpler tasks for identifying stationary objects, progressing to more complex tasks including reading moving signs or navigating through a virtual maze, wherein each task lasts between 30 seconds to 2 minutes, with controlled lighting transitions.

Clause 21. The method of any of Clauses 1-20, wherein simulating the one or more dynamic lighting scenarios comprises controlling one or more lighting conditions to change predictably and repeatably for each user to maintain consistency in testing across users.

Clause 22. The method of any of Clauses 1-21, wherein simulating the one or more dynamic lighting scenarios comprises using a library of lighting conditions that categorizes simulations by ambient light levels, dynamic glare sources, and specific environments.

Clause 23. The method of any of Clauses 1-22, wherein simulating the one or more dynamic lighting scenarios comprises using a library of lighting conditions that allows selection of specific scenarios or includes a preset sequence designed to test various aspects of night vision and glare sensitivity.

Clause 24. The method of any of Clauses 1-23, further comprising, prior to simulating the one or more dynamic lighting scenarios in the VR user interface: providing a visual stimuli in the VR user interface to measure a user's susceptibility level to motion sickness; and in accordance with a determination that the user's susceptibility to motion sickness is above a predetermined threshold, reducing a refresh rate of the VR user interface.

Clause 25. The method of any of Clauses 1-24, wherein tracking the eye movements and response times comprises tracking eyeball position in relation to light sensitivity while using a light source to cause glare.

Clause 26. The method of any of Clauses 1-25, wherein evaluating the user response based on the eye movements and the response times for testing night vision and glare sensitivity comprises tracking a response time to adapt to changes in lighting conditions as light is decreased.

Clause 27. The method of any of Clauses 1-26, wherein evaluating the user response based on the eye movements and the response times for testing night vision and glare sensitivity comprises tracking a focus on a glare as light is decreased.

Clause 28. The method of any of Clauses 1-27, wherein evaluating the user response based on the eye movements and the response times for testing night vision and glare sensitivity comprises measuring visual acuity under varying light conditions using tests comprising dynamic Snellen charts.

Clause 29. The method of any of Clauses 1-29, wherein evaluating the user response based on the eye movements and the response times for testing night vision and glare sensitivity comprises assessing an ability to distinguish between different shades of gray in low-light scenarios.

Clause 30. The method of any of Clauses 1-29, wherein evaluating the user response based on the eye movements and the response times for testing night vision and glare sensitivity comprises measuring a time taken for a vision to return to baseline or normal vision after exposure to a bright light.

Clause 31. The method of Clause 30, wherein evaluating the user response based on the eye movements and the response times for testing night vision and glare sensitivity comprises (i) one or more objective tests based on a response that indicates when a user starts seeing again, and (ii) one or more subjective tests comprising one or more vision acuity tests.

Clause 32. The method of any of Clauses 1-31, wherein evaluating the user response based on the eye movements and the response times for testing night vision and glare sensitivity comprises collecting data on reaction times, accuracy of task completion, eye movement patterns, and recovery times from glare.

Clause 33. The method of any of Clauses 1-32, wherein evaluating the user response based on the eye movements and the response times for testing night vision and glare sensitivity comprises using one or more metrics for identification accuracy, time to task completion, and time to visual recovery from glare, to assess night vision and glare sensitivity.

Clause 34. The method of any of Clauses 1-33, further comprising generating one or more reports for summarizing a performance across different lighting conditions.

Clause 35. The method of any of Clauses 1-34, further comprising generating one or more charts for showing visual clarity in low-light scenarios.

Clause 36. The method of any of Clauses 1-35, further comprising generating one or more graphs indicating recovery times from different levels of glare exposure.

Clause 37. The method of any of Clauses 1-26, further comprising displaying results from various contrast levels tested.

Clause 38. The method of any of Clauses 1-37, further comprising displaying one or more suggestions for further evaluation or corrective measures if deficiencies are identified.

Clause 39. The method of any of Clauses 1-38, wherein the resolution of the HMD comprises at least 1080 by 1200 pixels per eye.

Clause 40. The method of any of Clauses 1-39, wherein precision level for the eye tracking comprises at least 0.5 degrees of visual angle.

Clause 41. The method of any of Clauses 1-40, wherein infrared sensors for eye tracking sample at the rate of at least 120 Hz to capture rapid eye movements accurately.

Clause 42. The method any of Clauses 1-41, further comprising calibrating the one or more dynamic lighting scenarios using a control group comprising individuals with known conditions including retinitis pigmentosa (night blindness), normal vision, and those with a history of glare sensitivity.

Clause 43. The method any of Clauses 1-42, further comprising calibrating the one or more dynamic lighting scenarios using baseline metrics including average reaction times, standard recovery times from glare, and typical contrast sensitivity scores for each profile.

Clause 44. The method any of Clauses 1-43, further comprising validating results of testing by comparing results from the VR tests with conventional clinical tests to ensure accuracy.

Clause 45. The method any of Clauses 1-44, further comprising using statistical methods to validate consistency and reliability of the VR-based assessments.

Clause 46. A method of implementing a virtual vision test for measuring pupil reaction to light changes and visual imperfections, comprising: at an electronic device including a head-mounted display and a camera: generating a virtual reality (VR) user interface corresponding to a photorealistic virtual environment; rendering the VR user interface on the HMD; simulating one or more dynamic lighting scenarios in the VR user interface; and while simulating the one or more dynamic lighting scenarios, in real time: continuously tracking, using the camera, pupil data in response to visual stimuli presented in the one or more dynamic lighting scenarios; and measuring pupil reaction to light changes based on the pupil data.

Clause 47. The method of Clause 46, wherein the one or more dynamic lighting scenarios comprises sudden flashes of light that last between 100 to 500 milliseconds.

Clause 48. The method of Clause 47, wherein time between the sudden flashes of light range from 1 to 5 seconds.

Clause 49. The method of any of Clauses 46-48, wherein the one or more dynamic lighting scenarios comprises flashes with varying light intensities, from dim ($10 \text{ cd/m}^2$) to very bright ($1000 \text{ cd/m}^2$).

Clause 50. The method of any of Clauses 46-49, wherein the one or more dynamic lighting scenarios comprises scenarios with gradual changes in brightness with transitions over periods of 5 to 30 seconds.

Clause 51. The method of any of Clauses 46-50, wherein the one or more dynamic lighting scenarios comprises one or more scenarios selected from the group consisting of: sunrise, sunset and moving from a dimly lit room to a brightly lit outdoor environment.

Clause 52. The method of any of Clauses 46-51, wherein the one or more dynamic lighting scenarios comprises gradual increase in brightness over 30 seconds.

Clause 53. The method of any of Clauses 46-52, wherein the one or more dynamic lighting scenarios comprises a series of 10 flashes, each 100 milliseconds long, with 2-second intervals.

Clause 54. The method of any of Clauses 46-53, wherein the one or more dynamic lighting scenarios comprises a plurality of flashes with a 3.5 second interval between a first flash and a second flash and a 4.5 second interval between the second flash and a third flash.

Clause 55. The method of any of Clauses 46-54, wherein the one or more dynamic lighting scenarios comprises a plurality of flashes with at least a 3 second interval and lesser than a 10 second interval between two flashes.

Clause 56. The method of any of Clauses 46-55, wherein simulating the one or more dynamic lighting scenarios comprises driving lighting scenarios using a lighting scenarios library that categorizes abrupt changes for sudden flashes having subcategories for low, medium and high intensities, and gradual changes to brightness having subcategories for slow, medium and fast transitions.

Clause 57. The method of Clause 56, wherein the sudden flashes comprise 100 ms flashes at 100 cd/m2 and 500 ms flashes at 500 cd/m2.

Clause 58. The method of Clause 56, wherein the gradual brightness adjustment comprises 10-second transition from 100 cd/m2 to 500 cd/m2, and 30-second transition from 10 cd/m2 to 1,000 cd/m2.

Clause 59. The method of any of Clauses 46-58, wherein tracking the pupil data comprises using infrared light to monitor pupil size and movements without visible light interference, and tracking and recording pupil responses.

Clause 60. The method of any of Clauses 46-59, wherein tracking the pupil data comprises using one or more pupilometers of the electronic device to measure pupil response to light changes accurately.

Clause 61. The method of any of Clauses 46-60, wherein tracking the pupil data comprises using high-resolution infrared eye-tracking cameras capable of capturing detailed pupil size and movement that sample at least at 120 Hz.

Clause 62. The method of any of Clauses 46-61, wherein measuring pupil reaction to light changes based on the pupil data comprises: computing a latency for time to initial reaction for a pupil to start reacting to a change in light, based on the pupil data; computing an amplitude based on maximum pupil constriction and a baseline pupil size before the change in light, for the pupil data; and calculating a speed of constriction and dilation of the pupil in response to the change in light, based on the pupil data.

Clause 63. The method of any of Clauses 46-62, further comprising mapping abnormalities including anisocoria, optic neuropathy, and visual pathway disorder, based on measuring the pupil reaction to light changes.

Clause 64. The method of Clause 63, wherein mapping abnormalities to anisocoria comprises comparing responses of both eyes to identify differences in pupil size, based on the pupil data.

Clause 65. The method of Clause 63, wherein mapping abnormalities to optic neuropathy comprises analyzing consistency and speed of pupil responses to thereby detect potential nerve damage.

Clause 66. The method of Clause 63, wherein mapping abnormalities to visual pathway disorder comprises using one or more machine learning algorithms to compare responses to baseline data from individuals with known conditions.

Clause 67. The method of any of Clauses 46-66, wherein tracking pupil data comprises using at least 0.1 mm precision for measuring pupil size.

Clause 68. The method of any of Clauses 46-67, wherein tracking pupil data is performed at the rate of 5 milliseconds to ensure real-time tracking.

Clause 69. The method of any of Clauses 46-68, wherein tracking pupil data comprises using high-resolution sensors for capturing detailed images of the pupil.

Clause 70. The method any of Clauses 46-69, further comprising calibrating the one or more dynamic lighting scenarios based on a control group comprising individuals with normal vision, individuals with anisocoria, and individuals with optic neuropathy.

Clause 71. The method of any of Clauses 46-70, further comprising calibrating the one or more dynamic lighting scenarios using baseline responses for individuals with no known visual impairments, baseline for individuals with unequal pupil sizes, and baseline for individuals with optic nerve damage.

Clause 72. The method of any of Clauses 46-71, further comprising calibrating the one or more dynamic lighting scenarios using baseline pupillary responses comprising average latency of 150 ms, average constriction of 2.5 mm, and average constriction speed of 0.5 mm/s.

Clause 73. The method of any of Clauses 46-72, further comprising validating the measured pupil reaction to light changes by comparing a test group's responses to a control group's baseline metrics.

Clause 74. The method of any of Clauses 46-73, further comprising validating the measured pupil reaction to light changes using statistical methods including t-tests to validate the accuracy and consistency of measurement algorithms.

Clause 75. A method of implementing a virtual vision test for evaluating response time in detecting subtle visual changes under varying light conditions, comprising: at an electronic device including a head-mounted display and a camera: generating a virtual reality (VR) user interface corresponding to a photorealistic virtual environment; rendering the VR user interface on the HMD; simulating one or more dynamic lighting scenarios in the VR user interface; and while simulating the one or more dynamic lighting scenarios, in real time: continuously tracking, using the camera, eye movements in response to visual stimuli presented in the one or more dynamic lighting scenarios; and evaluating detection of subtle visual changes based on the eye movements.

Clause 76. The method of Clause 75, wherein simulating the one or more dynamic visual scenarios comprises generating and controlling subtle changes in visual field, including slight alterations in color, shape or movement.

Clause 77. The method of any of Clauses 75 or 76, wherein the one or more dynamic visual scenarios comprises one or more scenarios for identifying slight changes in color hue or brightness in a specific part of a visual field, including using color gradients that change slowly and subtly, requiring a user to respond when they detect the change.

Clause 78. The method of any of Clauses 75-77, wherein the one or more dynamic visual scenarios comprises one or more scenarios for detecting minor alterations in the shape of objects including slight deformation of a geometric figure, including displaying objects that gradually morph in shape, prompting users to identify the change.

Clause 79. The method of any of Clauses 75-78, wherein the one or more dynamic visual scenarios comprises one or more scenarios for identifying subtle movements within a stationary visual scene, including a slight shift in the position of an object, including implementing background scenes where certain elements move minimally, requiring users to pinpoint these movements.

Clause 80. The method of any of Clauses 75-79, wherein the one or more dynamic visual scenarios comprises lighting environments with (i) dim lighting that simulate low-light environments with brightness levels around 10 cd/m2.

Clause 81. The method of any of Clauses 75-80, wherein the one or more dynamic visual scenarios comprises lighting environments with bright lighting that simulate environments with high brightness around 1000 cd/m2.

Clause 82. The method of any of Clauses 75-81, wherein the one or more dynamic visual scenarios comprises lighting environments with fluctuating light levels including dynamic changes in lighting, transitioning between dim and bright environments over 5 to 30 seconds.

Clause 83. The method of any of Clauses 75-82, wherein the one or more dynamic lighting scenarios comprise subtle visual changes including color changes for gradual shifts in hue or saturation, requiring quick detection, shape changes for minor alterations in geometric chapes or object outlines, and slight, almost imperceptible movements within a scene.

Clause 84. The method of any of Clauses 75-83, wherein simulating the one or more dynamic lighting scenarios comprises using a library of lighting conditions that categorizes scenarios by (i) a type of visual change including color, shape and movement, and (ii) lighting environment including dim, bright and fluctuating.

Clause 85. The method of any of Clauses 75-84, wherein the library of lighting conditions further categorizes each scenario by a level of difficulty based on subtlety of changes and speed required for detecting subtle changes in color gradients for color detection, minor deformations of geometric figures for shape alterations, and slight shifts in object positions for movement detection.

Clause 86. The method of any of Clauses 75-85, wherein tracking the eye movements comprises using eye-tracking sensors with accuracy of 0.5 degrees of visual angle or better, at a sampling rate of at least 120 Hz to accurately capture quick eye movements and response times.

Clause 87. The method of any of Clauses 75-86, wherein tracking the eye movements comprises using infrared eye-tracking sensors to capture detailed eye movements, including fixations, saccades, and blinks.

Clause 88. The method of any of Clauses 75-87, wherein tracking eye movements comprises using at least 0.1 mm precision for measuring eye movements.

Clause 89. The method of any of Clauses 75-88, wherein tracking eye movements is performed with a latency below 5 milliseconds to ensure real-time tracking.

Clause 90. The method of any of Clauses 75-89, wherein tracking eye movements comprises using high-resolution sensors for capturing detailed images of the pupil and eye movement data.

Clause 91. The method of any of Clauses 75-90, wherein evaluating response times comprises mapping the response times to specific visual stimuli presented in the photorealistic virtual environment, correlating eye movement data with the appearance of visual changes.

Clause 92. The method of any of Clauses 75-91, wherein evaluating response times comprises mapping the eye movements to visual perception and cognitive processing speed.

Clause 93. The method of any of Clauses 75-92, wherein evaluating response times comprises measuring latency including calculating time taken from the presentation of a visual change to the user's detection as indicated by an eye movement or a press of a button.

Clause 94. The method of any of Clauses 75-93, wherein evaluating the eye movements comprises collecting baseline data from a control group with known visual and cognitive health status, and comparing response times and accuracy against the baseline data to identify deviations indicative of potential impairments.

Clause 95. The method of any of Clauses 75-94, wherein the electronic device comprises a high-resolution headset offering at least 1080 times 1200 pixels per eye, at least 90 Hz refresh rate to ensure smooth visual presentation and reduce motion sickness, and a wide field of view (FOV) of at least 110 degrees to provide an immersive experience.

Clause 96. The method of any of Clauses 75-95, further comprising providing insights into visual and cognitive processing abilities based on analysis of speed and accuracy of responses based on the eye movements.

Clause 97. The method of any of Clauses 75-96, further comprising providing an analysis of performance under each lighting condition, including reaction times and detection accuracy.

Clause 98. The method of any of Clauses 75-97, further comprising providing a diagnostic report including highlighting areas of concern that suggest conditions including macular degeneration, glaucoma, or cognitive decline.

Clause 99. The method of any of Clauses 75-98, further comprising calibrating the one or more dynamic lighting scenarios using known visual and cognitive health profiles of a control group comprising individuals with normal vision, age-related macular degeneration, glaucoma, early cognitive decline, and other relevant conditions.

Clause 100. The method of any of Clauses 75-99, further comprising calibrating the one or more dynamic lighting scenarios using baseline metrics including average reaction times, detection accuracy, and other relevant metrics.

Clause 101. The method of any of Clauses 75-100, further comprising using statistical methods including t-tests and ANOVA to validate consistency and reliability of the VR-based assessments by comparing test results against baseline metrics.

Clause 102. The method any of Clauses 75-101, further comprising validating results of testing by comparing results from the VR tests across different users and sessions.

Clause 103. A system for implementing a virtual vision test, comprising: a head-mounted display including a display, and one or more cameras; one or more processors; and memory storing one or more programs configured to be executed by the one or more processors, the one or more programs including instructions for: a user interface module configured to generate a virtual reality (VR) user interface corresponding to a three-dimensional virtual environment; a rendering module configured to render the VR user interface on the HMD, integrating VR user interface elements with the three-dimensional virtual environment; a simulation module configured to simulate one or more dynamic lighting scenarios in the VR user interface, including generating and managing various real-world lighting conditions and their changes over time; a tracking module configured to, continuously track, using at least one of the one or more cameras, eye movements and response times in response to visual stimuli presented in the one or more dynamic lighting scenarios, and continuously monitor and record pupil data, including pupil dilation and constriction, in response to visual stimuli presented in the one or more dynamic lighting scenarios; and an evaluation module configured to: evaluate user response based on the eye movements and the response times for testing night vision and glare sensitivity, measure pupil reaction to light changes based on the pupil data, and evaluate detection of subtle visual changes based on the eye movements.

Clause 104. A system for implementing a virtual vision test, comprising: a head-mounted display including a display, and one or more cameras; one or more processors; and memory storing one or more programs configured to be executed by the one or more processors, the one or more programs including instructions for performing the method of any of Clauses 1-102.

In some embodiments, any of the above clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.
Further Considerations As used herein, the word "module" refers to logic embodied in hardware or firmware, or to a collection of software instructions, possibly having entry and exit points, written in a programming language, such as, for example C++. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware.

It is contemplated that the modules may be integrated into a fewer number of modules. One module may also be separated into multiple modules. The described modules may be implemented as hardware, software, firmware or any combination thereof. Additionally, the described modules may reside at different locations connected through a wired or wireless network, or the Internet.

In general, it will be appreciated that the processors can include, by way of example, computers, program logic, or other substrate configurations representing data and instructions, which operate as described herein. In other embodiments, the processors can include controller circuitry, processor circuitry, processors, general purpose single-chip or multi-chip microprocessors, digital signal processors, embedded microprocessors, microcontrollers and the like.

Furthermore, it will be appreciated that in one embodiment, the program logic may advantageously be implemented as one or more components. The components may advantageously be configured to execute on one or more processors. The components include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

As used herein, the term "about" is relative to the actual value stated, as will be appreciated by those of skill in the art, and allows for approximations, inaccuracies and limits of measurement under the relevant circumstances. In one or more aspects, the terms "about," "substantially," and "approximately" may provide an industry-accepted tolerance for their corresponding terms and/or relativity between items.

As used herein, the term "comprising" indicates the presence of the specified integer(s), but allows for the possibility of other integers, unspecified. This term does not imply any particular proportion of the specified integers. Variations of the word "comprising," such as "comprise" and "comprises," have correspondingly similar meanings.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope. In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A method of implementing a virtual vision test for night vision and glare sensitivity, comprising:

at an electronic device including a head-mounted display (HMD) and a camera:

generating a virtual reality (VR) user interface corresponding to a photorealistic virtual environment;

rendering the VR user interface on the HMD;

simulating one or more dynamic lighting scenarios in the VR user interface by using one or more light mapping techniques to simulate realistic light behavior, including scattering, shadowing, and reflections; and while simulating the one or more dynamic lighting scenarios, in real time:

continuously tracking, using the camera, eye movements and response times in response to visual stimuli presented in the one or more dynamic lighting scenarios; and evaluating user response based on the eye movements and the response times for testing night vision and glare sensitivity.

2. The method of claim 1, wherein the photorealistic virtual environment comprises a high-fidelity virtual environment that can dynamically adjust light levels, colors, and/or sources.

3. The method of claim 2, wherein the high-fidelity virtual environment comprises dynamic light sources that incorporate movable light sources that can change intensity and position.

4. The method of claim 1, wherein the photorealistic virtual environment includes one or more configurable parameters to alter environment settings, while simulating the one or more dynamic lighting scenarios.

5. The method of claim 1, wherein the one or more dynamic lighting scenarios comprises randomized lighting scenarios that randomly change intensity from high intensity to low intensity and vice versa, without following real-world lighting scenarios.

6. The method of claim 1, wherein the one or more dynamic lighting scenarios comprises one or more nighttime scenes in urban streets, country roads, or indoor settings, simulated with varying degrees of ambient light.

7. The method of claim 1, wherein the one or more dynamic lighting scenarios comprises one or more low-light environments selected from the group consisting of: dimly lit parking garages, moonlit landscapes and twilight settings.

8. The method of claim 1, wherein simulating the one or more dynamic lighting scenarios comprises varying direction and intensity of light from one or more light sources hitting an eye, wherein the light causes a clouding effect leading to a glare.

9. The method of claim 1, wherein simulating the one or more dynamic lighting scenarios comprises simulating one or more scenarios for assessing the ability to distinguish between different shades of gray comprising changing optotype direction, whereby after solid black light, solid black is changed to a level of gray having a different gray level closer to white, including smoothing to lessen pixelation.

10. The method of claim 1, further comprising, prior to simulating the one or more dynamic lighting scenarios in the VR user interface:

providing a visual stimulus in the VR user interface to measure a user's susceptibility level to motion sickness; and in accordance with a determination that the user's susceptibility to motion sickness is above a predetermined threshold, reducing a refresh rate of the VR user interface.

11. The method of claim 1, wherein tracking the eye movements and response times comprises tracking eyeball position in relation to light sensitivity while using a light source to cause glare.

12. The method of claim 1, wherein evaluating the user response based on the eye movements and the response times for testing night vision and glare sensitivity comprises tracking a response time to adapt to changes in lighting conditions as light is decreased.

13. The method of claim 1, wherein evaluating the user response based on the eye movements and the response times for testing night vision and glare sensitivity comprises tracking a focus on a glare as light is decreased.

14. The method of claim 1, wherein evaluating the user response based on the eye movements and the response times for testing night vision and glare sensitivity comprises measuring visual acuity under varying light conditions using tests comprising dynamic Snellen charts.

15. The method of claim 1, wherein evaluating the user response based on the eye movements and the response times for testing night vision and glare sensitivity comprises assessing an ability to distinguish between different shades of gray in low-light scenarios.

16. The method of claim 1, wherein evaluating the user response based on the eye movements and the response times for testing night vision and glare sensitivity comprises measuring a time taken for a vision to return to baseline or normal vision after exposure to a bright light.

17. The method of claim 1, wherein evaluating the user response based on the eye movements and the response times for testing night vision and glare sensitivity comprises collecting data on reaction times, accuracy of task completion, eye movement patterns, and recovery times from glare.

18. An electronic device, comprising:

an HMD and a camera;

one or more processors; and memory for storing one or more programs for execution by the one or more processors, the one or more programs including instructions for, at an electronic device including a head-mounted display (HMD) and a camera:

generating a virtual reality (VR) user interface corresponding to a photorealistic virtual environment;

rendering the VR user interface on the HMD;

simulating one or more dynamic lighting scenarios in the VR user interface, the one or more dynamic lighting scenarios comprises one or more nighttime scenes in urban streets, country roads, or indoor settings, simulated with varying degrees of ambient light; and while simulating the one or more dynamic lighting scenarios, in real time:

continuously tracking, using the camera, eye movements and response times in response to visual stimuli presented in the one or more dynamic lighting scenarios; and evaluating user response based on the eye movements and the response times for testing night vision and glare sensitivity.

19. A method of implementing a virtual vision test for night vision and glare sensitivity, comprising:

at an electronic device including a head-mounted display (HMD) and a camera:

generating a virtual reality (VR) user interface corresponding to a photorealistic virtual environment;

rendering the VR user interface on the HMD;

simulating one or more dynamic lighting scenarios in the VR user interface;

while simulating the one or more dynamic lighting scenarios, in real time:

continuously tracking, using the camera, eye movements and response times in response to visual stimuli presented in the one or more dynamic lighting scenarios; and evaluating user response based on the eye movements and the response times for testing night vision and glare sensitivity; and prior to simulating the one or more dynamic lighting scenarios in the VR user interface, (i) providing a visual stimulus in the VR user interface to measure a user's susceptibility level to motion sickness and (ii) in accordance with a determination that the user's susceptibility to motion sickness is above a predetermined threshold, reducing a refresh rate of the VR user interface.

20. A method of implementing a virtual vision test for night vision and glare sensitivity, comprising:

at an electronic device including a head-mounted display (HMD) and a camera:

generating a virtual reality (VR) user interface corresponding to a photorealistic virtual environment;

rendering the VR user interface on the HMD;

simulating one or more dynamic lighting scenarios in the VR user interface; and while simulating the one or more dynamic lighting scenarios, in real time:

continuously tracking, using the camera, eye movements and response times in response to visual stimuli presented in the one or more dynamic lighting scenarios; and evaluating user response based on the eye movements and the response times for testing night vision and glare sensitivity by collecting data on reaction times, accuracy of task completion, eye movement patterns, and recovery times from glare.

* * * * *